US011358973B2

(12) United States Patent
Wang et al.

(10) Patent No.: US 11,358,973 B2
(45) Date of Patent: Jun. 14, 2022

(54) DI(HETERO)ARYL MACROCYCLIC COMPOUND FOR INHIBITING PROTEIN KINASE ACTIVITY

(71) Applicant: Shenzhen TargetRx, Inc., Guangdong (CN)

(72) Inventors: Yihan Wang, Guangdong (CN); Jiuyang Zhao, Guangdong (CN); Yixin Ai, Guangdong (CN)

(73) Assignee: Shenzhen TargetRx, Inc., Guangdong (CN)

( * ) Notice: Subject to any disclaimer, the term of this patent is extended or adjusted under 35 U.S.C. 154(b) by 5 days.

(21) Appl. No.: 17/047,877

(22) PCT Filed: Apr. 10, 2019

(86) PCT No.: PCT/CN2019/082051
§ 371 (c)(1),
(2) Date: Oct. 15, 2020

(87) PCT Pub. No.: WO2019/201131
PCT Pub. Date: Oct. 24, 2019

(65) Prior Publication Data

US 2021/0171542 A1 Jun. 10, 2021

(30) Foreign Application Priority Data

Apr. 16, 2018 (CN) ......................... 201810337944.6
Apr. 16, 2018 (CN) ......................... 201810338480.0

(51) Int. Cl.

| | |
|---|---|
| ***C07D 471/22*** | (2006.01) |
| ***C07D 487/04*** | (2006.01) |
| ***C07D 487/22*** | (2006.01) |
| ***C07D 498/22*** | (2006.01) |
| ***A61K 31/04*** | (2006.01) |
| ***A61K 31/519*** | (2006.01) |
| ***A61P 29/00*** | (2006.01) |
| ***A61P 25/04*** | (2006.01) |
| ***A61P 25/28*** | (2006.01) |
| ***A61P 35/00*** | (2006.01) |
| ***C07D 487/18*** | (2006.01) |
| ***C07D 498/18*** | (2006.01) |

(52) U.S. Cl.
CPC ............ *C07D 498/22* (2013.01); *A61P 35/00* (2018.01); *C07D 471/22* (2013.01); *C07D 487/18* (2013.01); *C07D 487/22* (2013.01); *C07D 498/18* (2013.01)

(58) Field of Classification Search
CPC .. C07D 471/22; C07D 487/04; C07D 487/22; C07D 498/22; A61K 31/04; A61K 31/519; A61P 29/00; A61P 25/04; A61P 25/28; A61P 35/00
See application file for complete search history.

(56) References Cited

U.S. PATENT DOCUMENTS

2020/0385386 A1* 12/2020 Wu ...................... C07D 471/22

FOREIGN PATENT DOCUMENTS

| | | | |
|---|---|---|---|
| CN | 102971322 | A | 3/2013 |
| CN | 106170289 | A | 11/2016 |
| CN | 110156813 | A | 8/2019 |
| CN | 110627812 | A | 12/2019 |
| CN | 111343987 | A | 6/2020 |
| CN | 111511749 | A | 8/2020 |
| WO | WO 2019/037761 | A1 | 2/2019 |
| WO | WO 2019/157879 | A1 | 8/2019 |

OTHER PUBLICATIONS

Chinese Office Action for Application No. 201910285027.2, dated Mar. 16, 2020.
Chinese Office Action for Application No. 201910285027.2, dated Oct. 26, 2020.

* cited by examiner

*Primary Examiner* — Bruck Kifle
(74) *Attorney, Agent, or Firm* — Wolf, Greenfield & Sacks, P.C.

(57) ABSTRACT

A di(hetero)aryl macrocyclic compound having an inhibitory effect on protein kinase activity, preparation and the use thereof. Specifically, disclosed are a di(hetero)aryl macrocyclic compound represented by formula (I), or a pharmaceutically acceptable salt, an enantiomer, a diastereomer, a racemate, a solvate, a hydrate, a polymorph, a prodrug or an active metabolite thereof, a pharmaceutical composition comprising said compound and the derivative thereof, and methods of using the same, including methods of treating cancers, pain, neurological diseases, autoimmune diseases and inflammation.

(I)

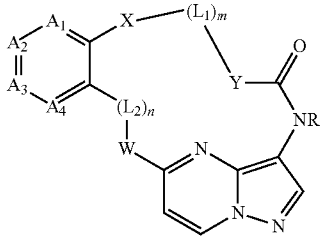

12 Claims, No Drawings

DI(HETERO)ARYL MACROCYCLIC COMPOUND FOR INHIBITING PROTEIN KINASE ACTIVITY

CROSS REFERENCE TO RELATED APPLICATIONS

The present application is a national application of PCT/CN2019/082051 filed on Apr. 10, 2019, which claims the priority of the Chinese Patent Application No. 201810338480.0 filed on Apr. 16, 2018, and the Chinese Patent Application No. 201810337944.6 filed on Apr. 16, 2018. The Chinese Patent Applications No. 201810338480.0 and No. 201810337944.6 are incorporated herein by reference as part of the disclosure of the present application.

TECHNICAL FIELD

The present disclosure belongs to the technical field of medicine, and particularly relates to specific di(hetero)aryl macrocyclic compounds, pharmaceutical compositions containing them, and preparation methods thereof and use thereof for the treatment of cancers, pain, neurological diseases, autoimmune diseases and inflammation.

BACKGROUND OF THE INVENTION

Protein kinases are key regulators of cell growth, proliferation and survival. Genetic and epigenetic changes accumulate in cancer cells, leading to abnormal activation of signal transduction pathways that drive malignant processes. The inhibition of these signal transduction pathways represents a promising intervention opportunity for targeted cancer therapies.

ALK belongs to the insulin receptor (IR) superfamily of tyrosine receptor kinases. Due to the important role of ALK in hematogenesis, solid and stromal tumors, it is considered to be an attractive molecular target for therapeutic intervention of cancers.

Tropomyosin-related tyrosine receptor kinase (TRK) is a high-affinity receptor for neurotrophin (NT). Members of the TRK family are highly expressed in neural original cells. Since TRK plays an important role in the transduction of pain perception and tumor cell growth and survival signals, inhibitors of TRK receptor kinases can provide benefits as therapeutic agents for pain and cancers.

ROS1 kinase is a tyrosine receptor kinase with an unknown ligand. It has been reported that ROS1 kinase undergoes gene rearrangement to produce constitutively active fusion proteins in many human cancers, including glioblastoma, non-small cell lung cancer (NSCLC), bile duct carcinoma, ovarian cancer, gastric adenocarcinoma, colorectal cancer, inflammatory myofibroblastic tumor, angiosarcoma and epithelioid hemangioendothelioma.

There is still a need in the art for small molecule inhibitors targeting these multiple proteins or tyrosine kinase with desired medical properties to solve the changing mutation resistance of kinase inhibitors. The di(hetero)aryl macrocyclic compounds of the present disclosure can effectively bind to the ATP binding sites of ALK, ROS1, and TRK kinases, and exhibit inhibitory effect on these proteins. More importantly, the compounds can bind to mutant types of these proteins, such as ALK G1202R, ALK L1196M, ROS1 G2032R or TRKA G595R and the like. More importantly, it can bind to mutants of these proteins. The compounds of the present disclosure are inhibitors of wild and mutant ALK ROS1, TRK, etc. and will be used to treat subjects with abnormal signaling of one or more of ALK, ROS1 or TRK.

SUMMARY OF THE INVENTION

In view of the above technical problems, the present disclosure provides a new di(hetero)aryl macrocyclic compound and a composition containing the compound and use thereof, which has better inhibitory activity against wild and mutant ALK, ROS1, TRK and other kinases, with lower side effects and/or better pharmacodynamics/pharmacokinetic properties, and can be used in the treatment of diseases mediated by one or more of ALK, ROS1 or TRK.

In this regard, the present disclosure adopts the following technical solutions:

In one aspect, the present disclosure provides compounds of formula (I):

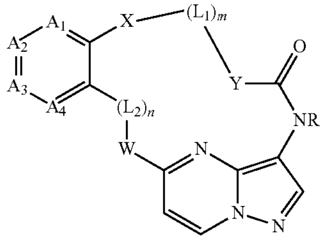

(I)

wherein, $A_1$ is selected from $CR_1$ or N;

$A_2$ is selected from $CR_2$ or N;

$A_3$ is selected from $CR_3$ or N;

$A_4$ is selected from $CR_4$ or N;

wherein $R_1$, $R_2$, $R_3$ and $R_4$ are independently selected from H, D, halogen, —CN, —$NO_2$, —$OR_a$, —$SR_a$, —$NR_bR_c$, —C(O)$R_a$, —C(O)O$R_a$, —C(O)$NR_bR_c$, —OC(O)$R_a$, —$NR_b$C(O)$R_a$, —S(O)$R_a$, —$S(O)_2R_a$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the above groups are optionally substituted by one or more D atoms until completely deuterated;

wherein $R_a$, $R_b$ and $R_c$ are each independently selected from H, D, $C_{1-6}$alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the above groups are optionally substituted by one or more D atoms until completely deuterated;

$L_1$ is selected from $C(R_{1a})(R_{2a})$, O, S, $N(R_{1a})$, C(O), S(O) or $S(O)_2$;

$L_2$ is selected from $C(R_{1b})(R_{2b})$, O, S, $N(R_{1b})$, C(O), S(O) or $S(O)_2$;

X is selected from O, S, $N(R_{1c})$ or $C(R_{1c})(R_{2c})$;

Y is selected from O, S, $N(R_{1d})$ or $C(R_{1d})(R_{2d})$;

W is selected from O, S, $N(R_{1e})$ or $C(R_{1e})(R_{2e})$;

R is selected from H, D, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the above groups are optionally substituted by one or more D atoms until completely deuterated;

m is selected from 1, 2, 3, 4 or 5;

n is selected from 1, 2 or 3;

wherein, $R_{1a}$ and $R_{2a}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C (O)$R_a$, —$C_{0-6}$ alkylene-C(O)O$R_a$, —$C_{0-6}$ alkylene-C(O)N$R_b$$R_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1a}$, $R_{2a}$ together with the atom to which they are attached form a $C_{3-7}$ cycloalkyl or 3- to 7-membered heterocyclyl; wherein the above groups are optionally substituted by one or more D atoms until completely deuterated;

$R_{1b}$ and $R_{2b}$ are each independently selected from H, D, halogen, —$C_{0-6}$ alkylene-CN, —$C_{0-6}$ alkylene-O$R_a$, —$C_{0-6}$ alkylene-S$R_a$, —$C_{0-6}$ alkylene-N$R_b$$R_c$, —$C_{0-6}$ alkylene-C(O)$R_a$, —$C_{0-6}$ alkylene-C(O)O$R_a$, —$C_{0-6}$ alkylene-C(O)N$R_b$$R_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1b}$, $R_{2b}$ together with the atom to which they are attached form a $C_{3-7}$ cycloalkyl or 3- to 7-membered heterocyclyl; wherein the above groups are optionally substituted by one or more D atoms until completely deuterated;

$R_{1c}$ and $R_{2c}$ are each independently selected from H, D, halogen, —$C_{0-6}$ alkylene-CN, —$C_{0-6}$ alkylene-O$R_a$, —$C_{0-6}$ alkylene-S$R_a$, —$C_{0-6}$ alkylene-N$R_b$$R_c$, —$C_{0-6}$ alkylene-C(O)$R_a$, —$C_{0-6}$ alkylene-C(O)O$R_a$, —$C_{0-6}$ alkylene-C(O)N$R_b$$R_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1c}$, $R_{2c}$ together with the atom to which they are attached form a $C_{3-7}$ cycloalkyl or 3- to 7-membered heterocyclyl; wherein the above groups are optionally substituted by one or more D atoms until completely deuterated;

$R_{1d}$ and $R_{2d}$ are each independently selected from H, D, halogen, —$C_{0-6}$ alkylene-CN, —$C_{0-6}$ alkylene-O$R_a$, —$C_{0-6}$ alkylene-S$R_a$, —$C_{0-6}$ alkylene-N$R_b$$R_c$, —$C_{0-6}$ alkylene-C(O)$R_a$, —$C_{0-6}$ alkylene-C(O)O$R_a$, —$C_{0-6}$ alkylene-C(O)N$R_b$$R_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1d}$, $R_{2d}$ together with the atom to which they are attached form a $C_{3-7}$ cycloalkyl or 3- to 7-membered heterocyclyl; wherein the above groups are optionally substituted by one or more D atoms until completely deuterated;

$R_{1e}$ and $R_{2e}$ are each independently selected from H, D, halogen, —$C_{0-6}$ alkylene-CN, —$C_{0-6}$ alkylene-O$R_a$, —$C_{0-6}$ alkylene-S$R_a$, —$C_{0-4}$ alkylene-N$R_b$$R_c$, —$C_{0-4}$ alkylene-C(O)$R_a$, —$C_4$ alkylene-C(O)O$R_a$, —$C_{0-6}$ alkylene-C(O)N$R_b$$R_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1e}$, $R_{2e}$ together with the atom to which they are attached form a $C_{3-7}$ cycloalkyl or 3- to 7-membered heterocyclyl; wherein the above groups are optionally substituted by one or more D atoms until completely deuterated;

substituents on different atoms in —X-$(L_1)_m$-Y— can be connected to form $C_{3-10}$ cycloalkyl, 3- to 10-membered heterocyclyl, $C_{6-14}$ aryl or 3- to 10-membered heteroaryl; wherein the above groups are optionally substituted by one or more D atoms until completely deuterated;

substituents on different atoms in -$(L_2)_n$-W— can be connected to form $C_{3-10}$ cycloalkyl, 3- to 10-membered heterocyclyl, $C_{6-14}$ aryl or 3- to 10-membered heteroaryl; wherein the above groups are optionally substituted by one or more D atoms until completely deuterated;

or pharmaceutically acceptable salts, enantiomers, diastereomers, racemates, solvates, hydrates, polymorphs, prodrugs or active metabolites thereof.

In another aspect, the present disclosure provides a pharmaceutical composition comprising a compound of the present disclosure or the pharmaceutically acceptable salt, enantiomer, diastereomer, racemate, solvate, hydrate, polymorph, prodrug or active metabolite thereof and pharmaceutically acceptable excipient(s). In a specific embodiment, the compound of the present disclosure is provided in the pharmaceutical composition in an effective amount. In a specific embodiment, the compound of the present disclosure is provided in a therapeutically effective amount. In a specific embodiment, the compound of the present disclosure is provided in a prophylactically effective amount.

In another aspect, the present disclosure provides a pharmaceutical composition comprising a compound of the present disclosure and pharmaceutically acceptable excipient(s), which also contains other therapeutic agent(s).

In another aspect, the present disclosure provides a kit comprising a compound of the present disclosure or the pharmaceutically acceptable salt, enantiomer, diastereomer, racemate, solvate, hydrate, polymorph, prodrug or active metabolite thereof, optionally other therapeutic agent(s) and pharmaceutically acceptable carrier(s), adjuvant(s) or vehicle(s).

In another aspect, the present disclosure provides a method for preparing a pharmaceutical composition as described above, including the following steps: mixing pharmaceutically acceptable excipient(s) with the compound of the present disclosure or the pharmaceutically acceptable salt, enantiomer, diastereomer, racemate, solvate, hydrate, polymorph, prodrug or active metabolite thereof to form a pharmaceutical composition.

In another aspect, the present disclosure provides a method for treating cancers, pain, neurological diseases, autoimmune diseases and inflammation in a subject in need thereof, the method includes administering to the subject an effective amount of the compound of the present disclosure or the pharmaceutically acceptable salt, enantiomer, diastereomer, racemate, solvate, hydrate, polymorph, prodrug or active metabolite thereof or the pharmaceutical composition of the present disclosure. In a specific embodiment, the compound is administered orally, subcutaneously, intravenously or intramuscularly. In a specific embodiment, the compound is administered chronically.

In another aspect, the present disclosure relates to a method for inhibiting proteins or tyrosine kinases (including one or more of ALK, ROS1, and TRK), which comprises contacting one or more of the kinases with an effective amount of at least one of the compound of formula (I) or the pharmaceutically acceptable salt, enantiomer, diastereomer, racemate, solvate, hydrate, polymorph, prodrug or active metabolite thereof and/or contacting with at least one pharmaceutical composition of the present disclosure, wherein the said contact is occurs ex vivo, in vitro or in vivo.

From the following specific embodiments, examples and claims, other objects and advantages of the present disclosure will be obvious to those skilled in the art.

Definitions

Chemical Definitions

Definitions of specific functional groups and chemical terms are described in more detail below.

When a range of values is listed, it is intended to encompass each value and sub-range within the range. For example "$C_{1-6}$ alkyl" is intended to encompass, $C_1$, $C_2$, $C_3$, $C_4$, $C_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$ and $C_{5-6}$ alkyl.

"$C_{1-6}$ alkyl" refers to a radical of a straight-chain or branched saturated hydrocarbon group having from 1 to 6 carbon atoms, and it is also referred to herein as "lower alkyl". In some embodiments, $C_{1-4}$ alkyl is particularly preferred. Examples of alkyl groups include, but are not limited to, methyl ($C_1$), ethyl ($C_2$) n-propyl ($C_3$), isopropyl ($C_3$), n-butyl ($C_4$) tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Regardless of whether the alkyl group is modified with "substituted", each instance of an alkyl group is independently optionally substituted, e.g. for instance with from 1 to 5 substituents, 1 to 3 substituents, or 1 substituent. Appropriate substituents are defined below.

"$C_{2-6}$alkenyl" refers to a radical of a straight-chain or branched hydrocarbon group having from 2 to 6 carbon atoms, one or more carbon-carbon double bonds (e.g., 1, 2, or 3 carbon-carbon double bonds). The one or more carbon-carbon double bonds may be internal (such as in 2-butenyl) or terminal (such as in 1-butenyl). In some embodiments, $C_{2-4}$ alkenyl is particularly preferred. Examples of alkenyl groups include, but are not limited to, ethenyl ($C_2$), 1-propenyl ($C_3$), 2-propenyl ($C_3$), 1-butenyl ($C_4$), 2-butenyl ($C_4$), butadienyl ($C_4$), pentenyl ($C_5$), pentadienyl ($C_5$), hexenyl ($C_6$), and the like. Regardless of whether the alkenyl group is modified with "substituted", each instance of an alkenyl group is independently optionally substituted, e.g. for instance with from 1 to 5 substituents, 1 to 3 substituents, or 1 substituent. Appropriate substituents are defined below.

"$C_{2-6}$ alkynyl" refers to a radical of a straight-chain or branched hydrocarbon group having from 2 to 6 carbon atoms, one or more carbon-carbon triple bonds (e.g., 1, 2, or 3 carbon-carbon triple bonds), and optionally one or more carbon-carbon double bonds (e.g., 1, 2, or 3 carbon-carbon double bonds). In some embodiments, $C_{2-4}$ alkynyl is particularly preferred. In some embodiments, alkynyl does not contain any double bonds. The one or more carbon-carbon triple bonds may be internal (such as in 2-butynyl) or terminal (such as in 1-butynyl). Examples of the alkynyl groups include, but are not limited to, ethynyl ($C_2$), 1-propynyl ($C_3$), 2-propynyl ($C_3$), 1-butynyl ($C_4$), 2-butynyl ($C_4$), pentynyl ($C_5$), hexynyl ($C_6$), and the like. Regardless of whether the alkynyl group is modified with "substituted", each instance of an alkynyl group is independently optionally substituted, e.g. for instance with from 1 to 5 substituents, 1 to 3 substituents, or 1 substituent. Appropriate substituents are defined below.

"$C_{2-6}$ alkylene" refers to a divalent group formed by removing another hydrogen of the $C_{1-6}$ alkyl, and can be a substituted or unsubstituted alkylene. In some embodiments, $C_{1-4}$ alkylene is particularly preferred. The unsubstituted alkylene groups include, but are not limited to, methylene ($—CH_2—$), ethylene ($—CH_2CH_2—$), propylene ($—CH_2CH_2CH_2—$), butylene ($—CH_2CH_2CH_2CH_2—$), pentylene ($—CH_2CH_2CH_2CH_2CH_2—$), hexylene ($—CH_2CH_2CH_2CH_2CH_2CH_2—$), etc. Examples of substituted alkylene groups, such as those substituted with one or more alkyl (methyl) groups, include, but are not limited to, substituted methylene ($—CH(CH_3)—$, $—C(CH_3)_2—$), substituted ethylene ($—CH(CH_3)CH_2—$, $—CH_2CH(CH)—$, $—C(CH_3)_2CH_2—$, $—CH_2C(CH_3)_2—$), substituted propylene ($—CH(CH_3)CH_2CH_2—$, $—CH_2CH(CH_3)CH_2—$, $—CH_2CH_2CH(CH_3)—$, $—C(CH_3)_2CH_2CH_2—$, $—CH_2C(CH_3)_2CH_2—$, $—CH_2CH_2C(CH_3)_2—$), etc.

"$C_{0-6}$ alkylene" includes the chemical bond and $C_{1-6}$ alkylene groups as defined above.

"$C_{1-6}$ alkoxy" refers to the group —OR wherein R is a substituted or unsubstituted $C_{1-6}$ alkyl group. In some embodiments, $C_{1-4}$ alkoxy group is particularly preferred. Specific alkoxy groups include, but are not limited to, methoxy, ethoxy, n-propoxy, isopropoxy, n-butoxy, tert-butoxy, sec-butoxy, n-pentyloxy, n-hexyloxy and 1,2-dimethylbutoxy.

"Halo" or "halogen" means fluorine (F), chlorine (Cl), bromine (Br) and iodine (I). In some embodiments, the halo group is F, —Cl or Br. In some embodiments, the halogen group is F or $C_{1-6}$ In some embodiments, the halogen group is F.

Thus, "$C_{1-6}$ haloalkyl" and "$C_{1-6}$ haloalkoxy" refer to the above "$C_{1-6}$ alkyl" and "$C_{1-6}$ alkoxy", which are substituted by one or more halo groups. In some embodiments, $C_{1-4}$ haloalkyl group is particularly preferred, and more preferably $C_{1-2}$ haloalkyl group. In some embodiments, $C_{1-4}$ haloalkoxy group is particularly preferred, and more preferably $C_{1-2}$ haloalkoxy group. Exemplary haloalkyl groups include, but are not limited to, $—CF_3$, $—CH_2F$, $—CHF_2$, $—CHFCH_2F$, $—CH_2CHF_2$, $—CF_2CF_3$, $—CCl_3$, $—CH_2C_1$, $—CHCl_2$, 2,2,2-trifluoro-1,1-dimethyl-ethyl, and the like. Exemplary haloalkoxy groups include, but are not limited to: $—OCH_2F$, $—OCHF_2$, $—OCF_3$, and the like.

"$C_{3-10}$ cycloalkyl" refers to a radical of a non-aromatic cyclic hydrocarbon group having from 3 to 10 ring carbon atoms and zero heteroatoms. In some embodiments, $C_{3-7}$ cycloalkyl is preferred, $C_{3-6}$ cycloalkyl is particularly preferred, and $C_{5-6}$ cycloalkyl is more preferred. Cycloalkyl also includes ring systems wherein the cycloalkyl ring, as defined above, is fused with one or more aryl or heteroaryl groups wherein the point of attachment is on the cycloalkyl ring, and in such instances, the number of carbons continue to designate the number of carbons in the cycloalkyl ring system. Exemplary cycloalkyl groups include, but is not limited to, cyclopropyl ($C_3$), cyclopropenyl ($C_3$), cyclobutyl ($C_4$), cyclobutenyl ($C_4$), cyclopentyl ($C_5$), cyclopentenyl ($C_5$), cyclohexyl ($C_6$), cyclohexenyl ($C_6$), cyclohexadienyl ($C_6$), cycloheptyl ($C_7$), cycloheptenyl ($C_7$), cycloheptadienyl ($C_7$), cycloheptatrienyl ($C_7$), cyclooctyl ($C_8$), cyclooctenyl ($C_8$), bicyclo[2.2.1]heptanyl ($C_7$), bicyclo[2.2.2]octanyl ($C_8$), cyclononyl ($C_9$), cyclononenyl ($C_9$), cyclodecyl ($C_{10}$), cyclodecenyl ($C_{10}$), octahydro-1H-indenyl ($C_9$), decahydronaphthyl ($C_{10}$), spiro[4.5]decyl ($C_{10}$) and the like. Regardless of whether the cycloalkyl group is modified with "substituted", each instance of a cycloalkyl group is independently optionally substituted, e.g., for instance with from 1 to 5 substituents, 1 to 3 substituents, or 1 substituent. Appropriate substituents are defined below.

"3- to 10-membered heterocyclyl" refers to a radical of a 3- to 10-membered non-aromatic ring system having ring carbon atoms and 1 to 4 ring heteroatoms, wherein each heteroatom is independently selected from nitrogen, oxygen, sulfur, boron, phosphorus, and silicon. In heterocyclyl groups that contain one or more nitrogen atoms, the point of attachment may be a carbon or nitrogen atom, as valency permits. In some embodiments, 3- to 7-membered heterocyclyl is preferred, which is a radical of a 3- to 7-membered non-aromatic ring system having ring carbon atoms and 1 to 3 ring heteroatoms; in some embodiments, 3- to 6-membered heterocyclyl is particularly preferred, which is a radical of a 3- to 6-membered non-aromatic ring system having ring carbon atoms and 1 to 3 ring heteroatoms; 5- to 6-membered heterocyclyl is more preferred, which is a radical of a 5- to 6-membered non-aromatic ring system having ring carbon atoms and 1 to 3 ring heteroatoms. Heterocyclyl also includes ring systems wherein the heterocyclyl ring, as defined above, is fused with one or more aryl or heteroaryl groups, wherein the point of attachment is on the heterocyclyl ring; and in such instances, the number of ring members continue to designate the number of ring members in the heterocyclyl ring system. Regardless of whether the heterocyclyl group is modified with "substituted", each instance of an heterocyclyl group is independently optionally substituted, e.g., for instance with from 1 to 5 substituents, 1 to 3 substituents, or 1 substituent. Appropriate substituents are defined below.

Exemplary 3-membered heterocyclyl groups containing one heteroatom include, but are not limited to, azirdinyl, oxiranyl, thiorenyl. Exemplary 4-membered heterocyclyl groups containing one heteroatom include, but are not limited to, azetidinyl, oxetanyl and thietanyl. Exemplary 5-membered heterocyclyl groups containing one heteroatom include, but are not limited to, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5-membered heterocyclyl groups containing two heteroatoms include, but are not limited to, dioxolanyl, oxasulfuranyl, disulfuranyl and oxazolidin-2-one. Exemplary 5-membered heterocyclyl groups containing three heteroatoms include, but are not limited to, triazolinyl, oxadiazolinyl, and thiadiazolinyl. Exemplary 6-membered heterocyclyl groups containing one heteroatom include, but are not limited to, piperidinyl, tetrahydropyranyl, dihydropyridinyl and thianyl. Exemplary 6-membered heterocyclyl groups containing two heteroatoms include, but are not limited to, piperazinyl, morpholinyl, dithianyl, dioxanyl. Exemplary 6-membered heterocyclyl groups containing three heteroatoms include, but are not limited to, triazinanyl. Exemplary 7-membered heterocyclyl groups containing one heteroatom include, but are not limited to, azepanyl, oxepanyl and thiepanyl. Exemplary 8-membered heterocyclyl groups containing one heteroatom include, but are not limited to, azocanyl, oxecanyl and thiocanyl. Exemplary 5-membered heterocyclyl groups fused to a $C_6$ aryl ring (also referred to herein as a 5,6-bicyclic heterocyclic ring) include, but are not limited to, indolinyl, isoindolinyl, dihydrobenzofuranyl, dihydrobenzothienyl, benzoxazolinonyl, and the like. Exemplary 6-membered heterocyclyl groups fused to an $C_6$ aryl ring (also referred to herein as a 6,6-bicyclic heterocyclic ring) include, but are not limited to, tetrahydroquinolinyl, tetrahydroisoquinolinyl, and the like.

"$C_{6-14}$ aryl" refers to a radical of a monocyclic or polycyclic (e.g., bicyclic or tricyclic) 4n+2 aromatic ring system (e.g., having 6, 10, or 14π electrons shared in a cyclic array) having 6-14 ring carbon atoms and zero heteroatoms. In some embodiments, an aryl group has six ring carbon atoms ("$C_6$ aryl"; e.g., phenyl). In some embodiments, an aryl group has ten ring carbon atoms ("$C_{10}$ aryl"; e.g., naphthyl such as 1-naphthyl and 2-naphthyl). In some embodiments, an aryl group has fourteen ring carbon atoms ("$C_{14}$ aryl"; e.g., anthracyl). In some embodiments. $C_{6-10}$ aryl is particularly preferred, and $C_6$ aryl is more preferred. Aryl also includes ring systems wherein the aryl ring, as defined above, is fused with one or more cycloalkyl or heterocyclyl groups and the radical or point of attachment is on the aryl ring, and in such instances, the number of carbon atoms continue to designate the number of carbon atoms in the aryl ring system. Regardless of whether the aryl group is modified with "substituted", each instance of an aryl group is independently optionally substituted, e.g., for instance with from 1 to 5 substituents, 1 to 3 substituents, or 1 substituent. Appropriate substituents are defined below.

"5- to 10-membered heteroaryl" refers to a radical of a 5-10 membered monocyclic or bicyclic 4n+2 aromatic ring system (e.g., having 6 or 10π electrons shared in a cyclic array) having ring carbon atoms and 1-4 ring heteroatoms, wherein each heteroatom is independently selected from nitrogen, oxygen and sulfur. In heteroaryl groups that contain one or more nitrogen atoms, the point of attachment may be a carbon or nitrogen atom, as valency permits. Heteroaryl bicyclic ring systems can include one or more heteroatoms in one or both rings. Heteroaryl includes ring systems wherein the heteroaryl ring, as defined above, is fused with one or more cycloalkyl or heterocyclyl groups wherein the point of attachment is on the heteroaryl ring, and in such instances, the number of ring members continue to designate the number of ring members in the heteroaryl ring system. In some embodiments, 5- to 6-membered heteroaryl group is particularly preferred, which is a 5-6 membered monocyclic or bicyclic 4n+2 aromatic ring system having ring carbon atoms and 1-4 ring heteroatoms. Regardless of whether the heteroaryl group is modified with "substituted", each instance of an heteroaryl group is independently optionally substituted, e.g., for instance with from 1 to 5 substituents, 1 to 3 substituents, or 1 substituent. Appropriate substituents are defined below.

Exemplary 5-membered heteroaryl groups containing one heteroatom include, but are not limited to, pyrrolyl, furanyl and thiophenyl. Exemplary 5-membered heteroaryl groups containing two heteroatoms include, but are not limited to, imidazolyl, pyrazolyl, oxazolyl, isoxazolyl, thiazolyl, and isothiazolyl. Exemplary 5-membered heteroaryl groups containing three heteroatoms include, but are not limited to, triazolyl, oxadiazolyl, and thiadiazolyl. Exemplary 5-membered heteroaryl groups containing four heteroatoms include, but are not limited to, tetrazolyl. Exemplary 6-membered heteroaryl groups containing one heteroatom include, but are not limited to, pyridinyl. Exemplary 6-membered heteroaryl groups containing two heteroatoms include, but are not limited to, pyridazinyl, pyrimidinyl, and pyrazinyl. Exemplary 6-membered heteroaryl groups containing three or four heteroatoms include, but are not limited to, triazinyl and tetrazinyl, respectively. Exemplary 7-membered heteroaryl groups containing one heteroatom include, but are not limited to, azepinyl, oxepinyl, and thiepinyl. Exemplary 5,6-bicyclic heteroaryl groups include, but are not limited to, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, but are not limited to naphthyridinyl, pteridinyl, quinolinyl, isoquinolinyl, cinnolinyl, quinoxalinyl, phthalazinyl, and quinazolinyl.

Exemplary carbon atom substituents include, but are not limited to, halogen, —CN, —$NO_2$, —$N_3$, —$SO_2H$, —$SO_3H$, —OH, —$OR^{aa}$, —$ON(R^{bb})_2$, —$N(R^{bb})_2$, —$N(R^{bb})_3{}^+X^-$, —$N(OR^{cc})R^{bb}$, —SH, —$SR^{aa}$, —$SSR^{cc}$, —$C(=O)R^{aa}$, —$CO_2H$, —CHO, —$C(OR^{cc})_2$, —$CO_2R^{aa}$, —$OC(=O)R^{aa}$, —$OCO_2R^{aa}$, —$C(=O)N(R^{bb})_2$, —$OC(=O)N(R^{bb})_2$, —$NRIC(=O)R^{aa}$, —$NR^{bb}CO_2R^{aa}$, —$NR^{bb}C(=O)N(R^{bb})_2$, —$C(=NR^{bb})R^{aa}$, —$C(=NR^{bb})OR^{aa}$, —$OC(=NR^{bb})R^{aa}$, —$OC(=NR^{bb})OR^{aa}$, —$C(=NR^{bb})N(R^{bb})_2$, —$OC(=NR^{aa})N(R^{aa})_2$, —$NR_bC(=NR^{bb})N(R^{bb})_2$, —$C(=O)NR^{bb}SO_2R^{aa}$, —$NR*SO_2R^{aa}$, —$SO_2N(R^{bb})_2$, —$SO_2R^{aa}$, —$SO_2OR^{aa}$, —$OSO_2R^{aa}$, —S(═O)$R^{aa}$, —OS(═O)$R^{aa}$, —Si$(R^{aa})_3$, —OSi$(R^{aa})_3$, —C(═S)N$(R^{bb})_2$, —C(═O)S$R^{aa}$, —C(═S)S$R^{aa}$, —SC(═S)S$R^{aa}$, —SC(═O)S$R^{aa}$, —OC(═O)S$R^{aa}$, —SC(═O)O$R^{aa}$, —SC(═O)$R^{aa}$, —P(═O)$_2R^{aa}$, —OP(═O)$_2R^{aa}$, —P(═O)(R')$_2$, —OP(═O)$(R^{aa})_2$, —OP(═O)(O$R^{cc}$), —P(═O)$_2$N$(R^{bb})_2$, —OP(═O)$_2$N$(R^{bb})_2$, —P(═O)(N$R^{bb}$)$_2$, —OP(═O)(NR*)$_2$, —N$R^{bb}$P(═O)(O$R^{cc}$)$_2$. —N$R^{bb}$P(═O)(N$R^{bb}$)$_2$, —P$(R^{cc})_2$, —P$(R^{cc})_3$, —OP$(R^{aa})_2$, —OP($R^{cc}$), —B$(R^{cc})_2$, —B(O$R^{cc}$)$_2$, —B$R^{aa}$(O$R^{cc}$), alkyl, perhaloalkyl, alkenyl, alkynyl, carbocyclyl, heterocyclyl, aryl, and heteroaryl, wherein each alkyl, alkenyl, alkynyl, carbocyclyl, heterocyclyl, aryl, and heteroaryl is independently substituted by 0, 1, 2, 3, 4, or 5 $R^{dd}$ groups;

or two geminal hydrogens on a carbon atom are replaced with the group ═O, ═S, ═NN$(R^{bb})_2$, ═NN$R^{bb}$C(═O)$R^{aa}$, ═NN$R^{bb}$C(═O)O$R^{aa}$, ═NN$R^{bb}$S(═O)$_2R^{aa}$, ═N$R^{bb}$, or ═NO$R^{cc}$;

each instance of $R^{aa}$ is independently selected from alkyl, perhaloalkyl, alkenyl, alkynyl, carbocyclyl, heterocyclyl, aryl, and heteroaryl, or two $R^a$ groups are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 $R^{dd}$ groups;

each instance of $R^{bb}$ is independently selected from hydrogen, —OH, —O$R^{aa}$, —N$(R^{cc})_2$, —CN, —C(═O)$R^{aa}$, —C(═O)N$(R_c)_2$, —C$O_2R^{aa}$, —S$O_2R^{aa}$, —C(═N$R^{cc}$)O$R^{aa}$, —C(═N$R^{cc}$)N$(R^{cc})_2$, —S$O_2$N$(R^{cc})_2$, —S$O_2R^{cc}$, —S$O_2$O$R^{cc}$, —SO$R^{aa}$, —C(═S)N$(R^{cc})_2$, —C(═O)S$R^{cc}$, —C(═S)S$R^{cc}$, —P(═O)$_2R^{aa}$, —P(═O)$(R^{aa})_2$, —P(═O)$_2$N$(R^{cc})_2$, —P(═O)(N$R^{cc}$)$_2$, alkyl, perhaloalkyl, alkenyl, alkynyl, carbocyclyl, heterocyclyl, aryl, and heteroaryl, or two $R^b$ groups are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 $R^d$ groups;

each instance of $R^{dd}$ is independently selected from hydrogen, alkyl, perhaloalkyl, alkenyl, alkynyl, carbocyclyl, heterocyclyl, aryl, and heteroaryl, or two $R^{cc}$ groups are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 $R^d$ groups;

each instance of $R^{dd}$ is independently selected from halogen, —CN, —N$O_2$, —$N_3$, —S$O_2$H, —S$O_3$H, —OH, —O$R^{ee}$, —ON$(R^{ff})_2$, —N$(R^{ff})_2$, —N$(R^{ff})_3{}^+X^-$, —N(O$R^{ee}$)$R^{ff}$, —SH, —S$R^{ee}$, —SS$R^{ee}$, —C(═O)$R^{cc}$, —C$O_2$H, —C$O_2R^{cc}$, —OC(═O)$R^{cc}$, —OC$O_2R^{cc}$, —C(═O)N$(R^{ff})_2$, —OC(═O)N$(R^{ff})_2$, —N$R^{ff}$C(═O)$R^{aa}$, —N$R^{ff}$C$O_2R^{ee}$, —N$R^{ff}$C(═O)N$(R^{ff})_2$, —C(═N$R^{ff}$)O$R^{ee}$, —OC(═N$R^{ff}$)$R^{ee}$, —OC(═N$R^{ff}$)O$R^{ee}$, —C(═N$R^{ff}$)N$(R^{ff})_2$, —OC(═N$R^{ff}$)N$(R^{ff})_2$, —N$R^{ff}$C(═N$R^{ff}$)N$(R^{ff})_2$, —N$R^{ff}$S$O_2R^{ee}$, —S$O_2$N$(R^{ff})_2$, —S$O_2R^{ee}$, —S$O_2$O$R^{ee}$, —OS$O_2R^{ee}$, —S(═O)$R^{ee}$, —Si$(R^{ee})_3$, —OSi$(R^{ee})_3$, —C(═S)N$(R^{ff})_2$, —C(═O)S$R^{ee}$, —C(═S)S$R^{ee}$, —SC(═S)S$R^{ee}$, —P(═O)$_2R^{ee}$, —P(═O)$(R^{ee})_2$, —OP(═O)$(R^{ee})_2$, —OP(═O)(O$R^{ee}$)$_2$, alkyl, perhaloalkyl, alkenyl, alkynyl, carbocyclyl, heterocyclyl, aryl, heteroaryl wherein each alkyl, alkenyl, alkynyl, carbocyclyl, heterocyclyl, aryl, and heteroaryl is independently substituted by 0, 1, 2, 3, 4, or 5 $R^{gg}$ groups, or two geminal $R^{dd}$ substituents may be joined to form ═O or ═S;

each instance of $R^{ee}$ is independently selected from alkyl, perhaloalkyl, alkenyl, 3 alkynyl, carbocyclyl, aryl, heterocyclyl, and heteroaryl, wherein each alkyl, alkenyl, alkynyl, carbocyclyl, heterocyclyl, aryl, and heteroaryl is independently substituted by 0, 1, 2, 3, 4, or 5 $R^{gg}$ groups;

each instance of $R^f$ is independently selected from hydrogen, alkyl, perhaloalkyl, alkenyl, alkynyl, carbocyclyl, heterocyclyl, aryl and heteroaryl, or two $R^{ff}$ groups are joined to form a heterocyclyl or heteroaryl ring, wherein each alkyl, alkenyl, alkyl, carbocyclyl, heterocyclyl, aryl, and heteroaryl is independently substituted by 0, 1, 2, 3, 4, or 5 $R^{gg}$ groups; and each instance of $R^{gg}$ is independently halogen, —CN, —N$O_2$, —$N_3$, —S$O_2$H, —S$O_3$H, —OH, —O$C_{1-6}$ alkyl, —ON($C_{1-6}$ alkyl)$_2$, —N($C_{1-6}$ alkyl)$_2$, —N($C_{1-6}$ alkyl)$_3{}^+X^-$, —NH($C_{1-6}$ alkyl)$_2{}^+X^-$, —N$H_2$($C_{1-6}$ alkyl)$^+X^-$, —N$H_3{}^+X^-$, —N(O$C_{1-6}$ alkyl)($C_{1-6}$ alkyl), —N(OH)($C_{1-6}$ alkyl), —NH(OH), —SH, —S$C_{1-6}$ alkyl, —SS($C_{1-6}$ alkyl), —C(═O)($C_{1-6}$ alkyl), —C$O_2$H, —C$O_2$($C_{1-6}$ alkyl), —OC(═O)($C_{1-6}$ alkyl), —OC$O_2$($C_{1-6}$ alkyl), —C(═O)N$H_2$, —C(═O)N($C_{1-6}$ alkyl)$_2$, —OC(═O)NH($C_{1-6}$ alkyl), —NHC(═O)($C_{0-6}$ alkyl), —N($C_{1-6}$ alkyl)C(═O)($C_{1-6}$ alkyl), —NHC$O_2$($C_{1-6}$ alkyl), —NHC(═O)N($C_{1-6}$ alkyl)$_2$, —NHC(═O)NH($C_{1-6}$ alkyl), —NHC(═O)N$H_2$, —C(═NH)O($C_{1-6}$ alkyl), —OC(═NH)($C_{1-6}$ alkyl), —OC(═NH)O$C_{1-6}$ alkyl, —C(═NH)N($C_{1-6}$ alkyl)$_2$, —C(═NH)NH($C_{1-6}$ alkyl), —C(═NH)N$H_2$, —OC(═NH)N($C_{1-6}$ alkyl)$_2$, —OC(NH)NH($C_{1-6}$ alkyl), —OC(NH)N$H_2$, —NHC(NH)N($C_{1-6}$ alkyl)$_2$, —NHC(═NH)N$H_2$, —NHS$O_2$($C_{1-6}$ alkyl), —S$O_2$N($C_{1-6}$ alkyl)$_2$, —S$O_2$NH($C_{1-6}$ alkyl), —S$O_2$N$H_2$, —S$O_2C_{1-6}$ alkyl, —S$O_2$O$C_{1-6}$ alkyl, —OS$O_2C_{1-6}$ alkyl, —SO$C_{1-6}$ alkyl, —Si($C_{1-6}$ alkyl)$_3$, —OSi($C_{1-6}$ alkyl)$_3$-C(═S)N($C_{1-6}$ alkyl)$_2$, C(═S)NH($C_{1-6}$ alkyl), C(═S)N$H_2$, —C(═O)S($C_{1-6}$ alkyl), —C(═S)S$C_{1-4}$ alkyl, —SC(═S)S$C_{1-6}$ alkyl, —P(═O)$_2$($C_{1-6}$ alkyl), —P(═O)($C_{1-6}$ alkyl)$_2$, —OP(═O)($C_{1-6}$ alkyl)$_2$, —OP(═O)(O$C_{1-6}$ alkyl)$_2$. $C_{1-6}$ alkyl, $C_{1-6}$ haloalkyl, $C_2$-$C_6$ alkenyl. $C_2$-$C_6$ alkynyl, $C_3$-$C_7$ carbocyclyl, $C_6$-$C_{10}$ aryl, $C_3$-$C_7$ heterocyclyl, $C_5$-$C_{10}$ heteroaryl; or two geminal $R^{gg}$ substituents may be joined to form ═O or ═S; wherein $X^-$ is a counterion.

Exemplary nitrogen atom substituents include, but are not limited to, hydrogen, —OH, —O$R^{aa}$, —N$(R^{cc})_2$, —CN, —C(═O)$R^{aa}$, —C(═O)N$(R^{aa})_2$, —C$O_2R^{aa}$, —S$O_2R^{aa}$, —C(═N$R^{bb}$)$R^{aa}$, —C(═N$R^{cc}$)O$R_a$, —C(═N$R^{cc}$)N$(R^{cc})_2$, —S$O_2$N$(R^{cc})_2$, —S$O_2R^{cc}$, —S$O_2$O$R^{cc}$, —SO$R^{aa}$, —C(═S)N$(R^{cc})_2$, —C(═O)S$R^{cc}$, —C(═S)S$R^{cc}$, —P(═O)$_2R^{cc}$, —P(═O)$(R^{aa})_2$, —P(═O)$_2$N$(R^{cc})_2$, —P(═O)(N$R^{cc}$)$_2$, alkyl, perhaloalkyl, alkenyl, alkynyl, carbocyclyl, heterocyclyl, aryl, and heteroaryl, or two $R^{ee}$ groups attached to a nitrogen atom are joined to form a heterocyclyl or heteroaryl ring, wherein each alkyl, alkenyl, alkynyl, carbocyclyl, heterocyclyl, aryl, and heteroaryl is independently substituted by 0, 1, 2, 3, 4, or 5 $R^{dd}$ groups, and wherein $R^{aa}$, $R^{bb}$, $R^{cc}$ and $R^{dd}$ are as defined above.

"Deuterated" or "D" refers to that one or more hydrogens in a compound or group are replaced by deuterium; deuteration can be mono-substitution, di-substitution, multi-substitution or per-substitution. The terms "one or more deuterated" and "deuterated one or more times" are used interchangeably.

"Non-deuterated compound" refers to a compound wherein the content of the deuterium atom is not higher than the natural content of the deuterium isotope (0.015%).

The isotope content of deuterium at the deuterated position is at least greater than the natural isotope content of deuterium (0.015%), preferably greater than 30%, alternatively greater than 50%, alternatively greater than 75%, alternatively greater than 95%, and alternatively greater than 99%.

The term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, Berge et al., describes pharmaceutically acceptable salts in detail in J. Pharmaceutical Sciences (1977) 66: 1-19. Pharmaceutically acceptable salts of the compounds of the present disclosure include those derived from suitable inorganic and organic acids and inorganic and organic bases. Examples of pharmaceutically acceptable, nontoxic acid addition salts are salts formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid. Salts formed by using regular methods used in the art such as ion exchange are also included. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Other pharmaceutically acceptable salts include, when appropriate, nontoxic ammonium, quaternary ammonium, and amine cations formed with counterions such as halide, hydroxide, carboxylate, sulfate, phosphate, nitrate, lower alkyl sulfonate, and aryl sulfonate.

"Active metabolite" refers to the pharmacologically active product produced by the in vivo metabolization of the compound of formula (I) or salt thereof. The prodrugs and active metabolites of compounds can be determined using conventional techniques known or available in the art.

A "subject" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or a non-human animal, e.g., a mammal such as primates (e.g., cynomolgus monkeys, rhesus monkeys), cattle, pigs, horses, sheep, goats, rodents, cats, and/or dogs. In certain embodiments, the subject is a human. In certain embodiments, the subject is a non-human animal. The terms "human", "patient" and "subject" are used interchangeably herein.

Disease, disorder, and condition are used interchangeably herein.

As used herein, and unless otherwise specified, the terms "treat", "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

"Combination" and related terms mean the simultaneous or sequential administration of a therapeutic agent of the present disclosure. For example, a compound disclosed herein may be administered simultaneously or sequentially with another therapeutic agent in separate unit dosage forms, or together with another therapeutic agent in a single unit dosage form.

Specific Embodiments

Compound

Herein, "the compound of the present disclosure" refers to the compound of formula (I) to the compound of formula (VI) and the compound of formula (I') to the compound of formula (V') (including the subsets of each formula, such as the compound of formula (III-1)), or pharmaceutically acceptable salts, enantiomers, diastereomers, racemates, solvates, hydrates, polymorphs, prodrugs or active metabolites thereof.

In one embodiment, the present disclosure relates to the compound of formula (I):

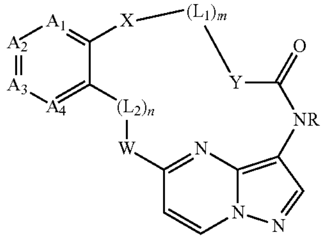

(I)

wherein, $A_1$ is selected from $CR_1$ or N;

$A_2$ is selected from $CR_2$ or N;

$A_3$ is selected from $CR_3$ or N;

$A_4$ is selected from $CR_4$ or N;

wherein $R_1$, $R_2$, $R_3$ and $R_4$ are independently selected from H, D, halogen, —CN, —$NO_2$, —$OR_a$, —$SR_a$, —$NR_bR_c$, —$C(O)R_a$, —$C(O)OR_a$, —$C(O)NR_bR_c$, —$OC(O)R_a$, —$NR_bC(O)R_a$, —$S(O)R_a$, —$S(O)_2R_a$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the above groups are optionally substituted by one or more D atoms until completely deuterated;

wherein $R_a$, $R_b$ and $R_c$ are each independently selected from H, D, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the above groups are optionally substituted by one or more D atoms until completely deuterated;

$L_1$ is selected from $C(R_{1a})(R_{2a})$, O, S, $N(R_{1a})$, C(O), S(O) or $S(O)_2$;

$L_2$ is selected from $C(R_{1b})(R_{2b})$, O, S, $N(R_{1b})$, C(O), S(O) or $S(O)_2$;

X is selected from O, S, $N(R_{1c})$ or $C(R_{1c})R_{2c})$;

Y is selected from O, S, $N(R_{1d})$ or $C(R_{1d})(R_{2d})$;

W is selected from O, S, $N(R_{1e})$ or $C(R_{1e})(R_{2e})$;

R is selected from H, D, $C_{0-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the above groups are optionally substituted by one or more D atoms until completely deuterated;

m is selected from 1, 2, 3, 4 or 5;

n is selected from 1, 2 or 3;

wherein, $R_{1a}$ and $R_{2a}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-4}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1a}$, $R_{2a}$ together with the atom to which they are attached form a $C_{3-7}$ cycloalkyl or 3- to 7-membered heterocyclyl; wherein the above groups are optionally substituted by one or more D atoms until completely deuterated;

$R_{1b}$ and $R_{2b}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-4}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1b}$. $R_{2b}$ together with the atom to which they are attached form a $C_{3-7}$ cycloalkyl or 3- to 7-membered heterocyclyl; wherein the above groups are optionally substituted by one or more D atoms until completely deuterated;

$R_{1c}$ and $R_{2c}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{1-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1c}$, $R_{2c}$ together with the atom to which they are attached form a $C_{3-7}$ cycloalkyl or 3- to 7-membered heterocyclyl; wherein the above groups are optionally substituted by one or more D atoms until completely deuterated;

$R_{1d}$ and $R_{2d}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1d}$, $R_{2d}$ together with the atom to which they are attached form a $C_{3-7}$ cycloalkyl or 3- to 7-membered heterocyclyl; wherein the above groups are optionally substituted by one or more D atoms until completely deuterated;

$R_{1e}$ and $R_{2e}$ are each independently selected from H, D halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1e}$, $R_{2e}$ together with the atom to which they are attached form a $C_{1-7}$ cycloalkyl or 3- to 7-membered heterocyclyl; wherein the above groups are optionally substituted by one or more D atoms until completely deuterated;

substituents on different atoms in —X-$(L_1)_m$-Y— can be connected to form $C_{3-10}$ cycloalkyl, 3- to 10-membered heterocyclyl, $C_{6-4}$ aryl or 3- to 10-membered heteroaryl; wherein the above groups are optionally substituted by one or more D atoms until completely deuterated;

substituents on different atoms in -$(L_2)_n$-W— can be connected to form $C_{3-10}$ cycloalkyl, 3- to 10-membered heterocyclyl, $C_{6-10}$ aryl or 3- to 10-membered heteroaryl; wherein the above groups are optionally substituted by one or more D atoms until completely deuterated;

or pharmaceutically acceptable salts, enantiomers, diastereomers, racemates, solvates, hydrates, polymorphs, prodrugs or active metabolites thereof.

In another embodiment, the present disclosure relates to the aforementioned compound, which is of formula (II):

(II)

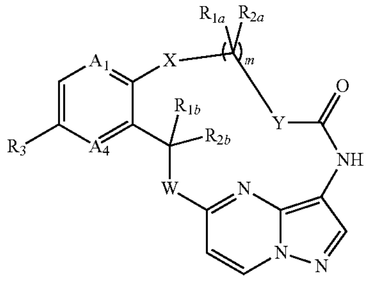

wherein, $A_1$ is selected from $CR_1$ or N;

$A_4$ is selected from $CR_4$ or N;

wherein $R_1$, $R_3$ and $R_4$ are independently selected from H, D, halogen, —CN, —$NO_2$, —$OR_a$, —$SR_a$, —$NR_bR_c$, —C(O)$R_a$, —C(O)$OR_a$, —C(O)$NR_bR_c$, —OC(O)$R_a$, —$NR_b$C(O)$R_a$, —S(O)$R_a$, —$S(O)_2R_a$. $C_{1-6}$alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the above groups are optionally substituted by one or more D atoms until completely deuterated;

wherein $R_a$, $R_b$ and $R_c$ are each independently selected from H, D, $C_{1-6}$ alkyl $C_{1-6}$ haloalkyl, $C_{3-7}$ cycloalkyl, 3- to 7-membered heterocyclyl, $C_{6-10}$ aryl or 5- to 10-membered heteroaryl; wherein the above groups are optionally substituted by one or more D atoms until completely deuterated;

X is selected from O or $C(R_{1c})(R_{2c})$;

Y is selected from $N(R_{1d})$ or $C(R_{1d})(R_{2d})$;

W is selected from O or NH;

m is selected from 1, 2, 3, 4 or 5;

$R_{1a}$ and $R_{2a}$ are each independently selected from H, D halogen, —$C_{0-6}$alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1a}$, $R_{2a}$ together with the atom to which they are attached form a $C_{3-7}$ cycloalkyl or 3- to 7-membered heterocyclyl; wherein the above groups are optionally substituted by one or more D atoms until completely deuterated;

$R_{1b}$ and $R_{2b}$ are each independently selected from H, D, halogen, —$C_{0-6}$ alkylene-CN, —$C_{0-6}$alkylene-$OR_a$, —$C_{0-6}$ alkylene-$SR_a$, —$C_{0-6}$ alkylene-$NR_bR_c$, —$C_{0-4}$ alkylene-C(O)$R_a$, —$C_{0-6}$ alkylene-C(O)$OR_a$, —$C_{0-6}$alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1b}$, $R_{2b}$ together with the atom to which they are attached form a $C_{3-7}$ cycloalkyl or 3- to 7-membered heterocyclyl; wherein the above groups are optionally substituted by one or more D atoms until completely deuterated;

wherein, $R_{1c}$ and $R_{2c}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)O$R_a$, —$C_{0-6}$ alkylene-C(O)N$R_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1c}$, $R_{2c}$ together with the atom to which they are attached form a $C_{3-7}$ cycloalkyl or 3- to 7-membered heterocyclyl; wherein the above groups are optionally substituted by one or more D atoms until completely deuterated;

$R_{1d}$ and $R_{2d}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-4}$ alkylene-$NR_bR_c$, —$C_{0-4}$ alkylene-C(O)$R_a$, —$C_{0-6}$ alkylene-C(O)O$R_a$, —$C_{0-6}$ alkylene-C(O)N$R_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1d}$. $R_{1d}$ together with the atom to which they are attached form a $C_{3-7}$ cycloalkyl or 3- to 7-membered heterocyclyl; wherein the above groups are optionally substituted by one or more D atoms until completely deuterated;

substituents on different atoms in —X—(C($R_{1a}$)($R_{2a}$))$_m$—Y— can be connected to form $C_{3-10}$ cycloalkyl, 3- to 10-membered heterocyclyl, $C_{6-14}$ aryl or 3- to 10-membered heteroaryl; wherein the above groups are optionally substituted by one or more D atoms until completely deuterated;

or pharmaceutically acceptable salts, enantiomers, diastereomers, racemates, solvates, hydrates, polymorphs, prodrugs or active metabolites thereof.

In another embodiment, the present disclosure relates to the aforementioned compound, which is of formula (III-1) or (III-2):

(III-1)

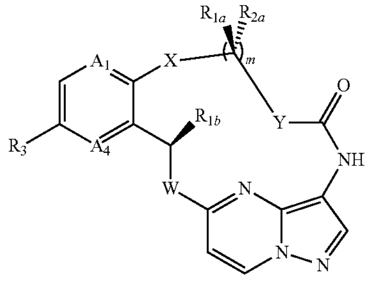

or (III-2)

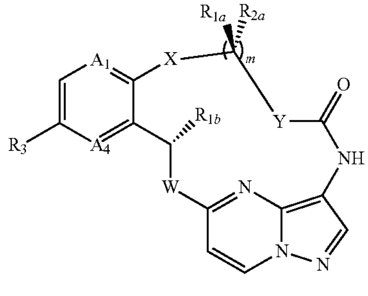

wherein, $A_1$ is selected from $CR_1$ or N;

$A_4$ is selected from $CR_4$ or N;

wherein $R_1$, $R_3$ and $R_4$ are independently selected from H, D, halogen, —CN, —$NO_2$, —$OR_a$, —$SR_a$, —$NR_bR_c$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the above groups are optionally substituted by one or more D atoms until completely deuterated;

wherein $R_a$, $R_b$ and $R_c$ are each independently selected from H, D, $C_{1-6}$ alkyl or $C_{1-6}$ haloalkyl; wherein the above groups are optionally substituted by one or more D atoms until completely deuterated;

X is selected from O or C($R_{1c}$)($R_{2c}$);

Y is selected from N($R_{1d}$) or C($R_{1d}$)($R_{2d}$);

W is selected from O or NH;

m is selected from 1, 2 or 3;

$R_{1a}$ and $R_{2a}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)O$R_a$, —$C_{0-6}$ alkylene-C(O)N$R_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1a}$, $R_{2a}$ together with the atom to which they are attached form a $C_{3-7}$ cycloalkyl or 3- to 7-membered heterocyclyl wherein the above groups are optionally substituted by one or more D atoms until completely deuterated;

$R_{1b}$ is selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)O$R_a$, —$C_{0-6}$ alkylene-C(O)N$R_bR_c$, $C_{1-6}$ alkyl, $C_{0-6}$ haloalkyl, $C_{2-6}$ alkenyl, $C_2$_alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; wherein the above groups are optionally substituted by one or more D atoms until completely deuterated;

wherein, $R_{1c}$ and $R_{2e}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)O$R_a$, —$C_{0-6}$ alkylene-C(O)N$R_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1c}$, $R_{2c}$ together with the atom to which they are attached form a $C_{3-7}$ cycloalkyl or 3- to 7-membered heterocyclyl wherein the above groups are optionally substituted by one or more D atoms until completely deuterated;

$R_{1d}$ and $R_{2d}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{1-6}$ alkylene-C(O)O$R_a$, —$C_{0-6}$ alkylene-C(O)N$R_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1d}$, $R_{2d}$ together with the atom to which they are attached form a $C_{3-7}$ cycloalkyl or 3- to 7-membered heterocyclyl; wherein the above groups are optionally substituted by one or more D atoms until completely deuterated;

substituents on different atoms in —X—(C($R_{1a}$)($R_{2a}$))$_m$—Y— can be connected to form $C_{3-10}$ cycloalkyl, 3- to 10-membered heterocyclyl, $C_{1-14}$ aryl or 3- to 10-membered heteroaryl; wherein the above groups are optionally substituted by one or more D atoms until completely deuterated;

or pharmaceutically acceptable salts, enantiomers, diastereomers, racemates, solvates, hydrates, polymorphs, prodrugs or active metabolites thereof.

In another embodiment, the present disclosure relates to the aforementioned compound, which is of formula (IV-1) or (IV-2):

(IV-1)

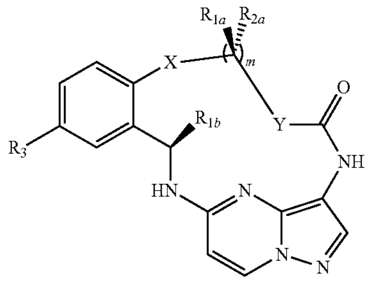

or (IV-2)

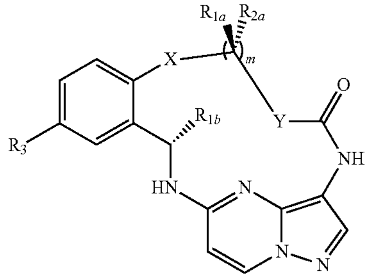

wherein, $R_3$ is selected from H, D halogen, —CN, —$NO_2$, —$OR_a$, —$SR_a$ or —$NR_bR_c$;

wherein $R_a$, $R_b$ and $R_c$ are each independently selected from H, D, $C_{1-6}$ alkyl or $C_{0-6}$ haloalkyl; wherein the above groups are optionally substituted by one or more D atoms until completely deuterated;

X is selected from O or $C(R_{1c})(R_{2c})$;

Y is selected from NH, $CH_2$ or C(Me)(Me); wherein the above groups are optionally substituted by one or more D atoms until completely deuterated;

m is selected from 1, 2 or 3;

$R_{1a}$ and $R_{2a}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1a}$, $R_{2a}$ together with the atom to which they are attached form a $C_{3-7}$ cycloalkyl or 3- to 7-membered heterocyclyl; wherein the above groups are optionally substituted by one or more D atoms until completely deuterated;

$R_{1b}$ is selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —C alkylene-$C_3$, cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; wherein the above groups are optionally substituted by one or more D atoms until completely deuterated;

wherein, $R_{1c}$ and $R_{2c}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1c}$, $R_{2c}$ together with the atom to which they are attached form a $C_{3-7}$ cycloalkyl or 3- to 7-membered heterocyclyl; wherein the above groups are optionally substituted by one or more D atoms until completely deuterated;

alternatively, $R_3$ is selected from H, D, halogen, —CN or —$NO_2$;

X is O;

Y is selected from NH, $CH_2$ or C(Me)(Me); wherein the above groups are optionally substituted by one or more D atoms until completely deuterated;

m is selected from 1, 2 or 3;

$R_{1a}$ and $R_{2a}$ are independently selected from H, D, $C_{1-6}$ alkyl or $C_{1-6}$ haloalkyl; wherein the above groups are optionally substituted by one or more D atoms until completely deuterated;

$R_{1b}$ is selected from $C_{1-6}$ alkyl or $C_{1-6}$ haloalkyl; wherein the above groups are optionally substituted by one or more D atoms until completely deuterated;

alternatively, $R_3$ is selected from H, D, halogen, —CN or —$NO_2$;

X is O;

Y is selected from $CH_2$ or C(Me)(Me); wherein the above groups are optionally substituted by one or more D atoms until completely deuterated;

m is selected from 1, 2 or 3;

$R_{1a}$ and $R_{2a}$ are independently selected from H, D, $C_{1-6}$ alkyl or $C_1$ haloalkyl; wherein the above groups are optionally substituted by one or more D atoms until completely deuterated;

$R_{1b}$ is selected from $C_{1-6}$ alkyl or $C_{1-6}$ haloalkyl; wherein the above groups are optionally substituted by one or more D atoms until completely deuterated;

or pharmaceutically acceptable salts, enantiomers, diastereomers, racemates, solvates, hydrates, polymorphs, prodrugs or active metabolites thereof.

In another embodiment, the present disclosure relates to the aforementioned compound, which is of formula (V-1) or (V-2):

(V-1)

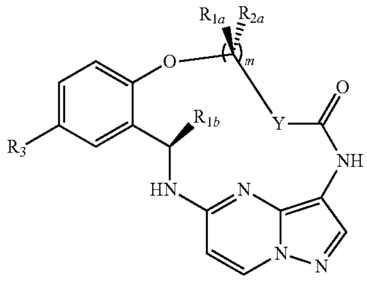

or (V-2)

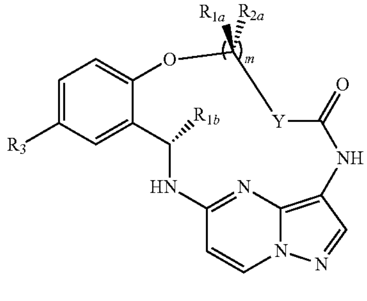

wherein, $R_3$ is selected from H, D, halogen, —CN or —$NO_2$;

Y is selected from NH, $CH_2$, CHD or $CD_2$;

m is selected from 1, 2 or 3;

$R_{1a}$ and $R_{2a}$ are each independently selected from H, D, $C_{1-6}$ alkyl or $C_{1-6}$ haloalkyl; wherein the above groups are optionally substituted by one or more D atoms until completely deuterated;

$R_{1b}$ is selected from H, D, $C_{1-6}$ alkyl or $C_{1-6}$ haloalkyl; wherein the above groups are optionally substituted by one or more D atoms until completely deuterated;

or pharmaceutically acceptable salts, enantiomers, diastereomers, racemates, solvates, hydrates, polymorphs, prodrugs or active metabolites thereof.

In another embodiment, the present disclosure relates to the aforementioned compound, which is of formula (VI-1) or (VI-2):

(VI-1)

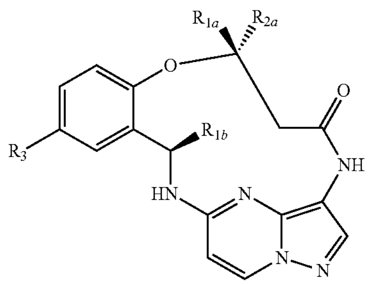

or (VI-2)

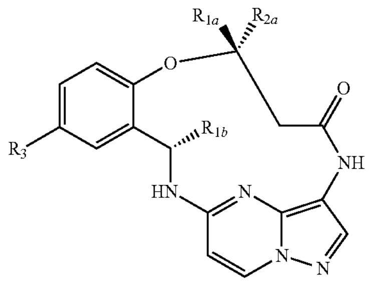

wherein, $R_3$ is selected from H, D, halogen, —CN or —$NO_2$;

$R_{1a}$ and $R_{2a}$ are independently selected from H, D, $C_{1-6}$ alkyl or $C_{1-6}$ haloalkyl; wherein the above groups are optionally substituted by one or more D atoms until completely deuterated;

$R_{1b}$ is selected from H, D, $C_{1-6}$ alkyl or $C_{1-6}$ haloalkyl; wherein the above groups are optionally substituted by one or more D atoms until completely deuterated;

or pharmaceutically acceptable salts, enantiomers, diastereomers, racemates, solvates, hydrates, polymorphs, prodrugs or active metabolites thereof.

In another embodiment, the present disclosure relates to the aforementioned compound, which is the compound of formula (I'):

(I')

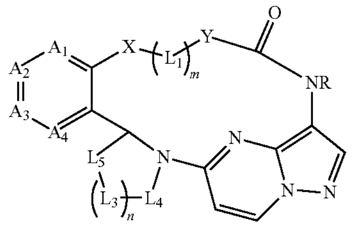

wherein, $A_1$ is selected from $CR_1$ or N;

$A_2$ is selected from $CR_2$ or N;

$A_3$ is selected from $CR_3$ or N;

$A_4$ is selected from $CR_4$ or N;

wherein $R_1$, $R_2$, $R_3$ and $R_4$ are independently selected from H, D, halogen, —CN, —$NO_2$, —$OR_a$, —$SR_a$, —$NR_bR_c$, —C(O)$R_a$, —C(O)$OR_a$, —C(O)$NR_bR_c$, —OC(O)$R_a$, —$NR_b$C(O)$R_a$, —S(O)$R_a$, —S(O)$_2R_a$, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the above groups are optionally substituted by one or more D atoms until completely deuterated;

wherein $R_a$, $R_b$ and $R_c$ are each independently selected from H, D, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the above groups are optionally substituted by one or more D atoms until completely deuterated;

$L_1$ is selected from C($R_{1a}$)($R_{2a}$), O, S, N($R_{1a}$), C(O), S(O) or S(O)$_2$;

X is selected from O, S, N($R_{1c}$) or C($R_{1c}$)($R_{2c}$);

Y is selected from O, S, N($R_{1d}$) or C($R_{1d}$)($R_{2d}$);

$L_3$ is selected from C($R_{1f}$)($R_{2f}$), O, S, N($R_{1f}$), C(O), S(O) or S(O)$_2$;

$L_4$ is selected from C($R_{1g}$)($R_{2g}$), O, S, N($R_{1g}$), C(O), S(O) or S(O)$_2$;

$L_5$ is selected from C($R_{1h}$)($R_{2h}$), O, S, N($R_{1h}$), C(O), S(O) or S(O)$_2$;

R is selected from H, D, $C_{1-6}$ alkyl, $C_{1-6}$ haloalkyl, $C_{3-7}$ cycloalkyl, 3- to 7-membered heterocyclyl, $C_{6-10}$ aryl or 5- to 10-membered heteroaryl; wherein the above groups are optionally substituted by one or more D atoms until completely deuterated;

m is selected from 1, 2, 3, 4 or 5;

n is selected from 1, 2 or 3;

wherein, $R_{1a}$ and $R_{2a}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-4}$ alkylene-$NR_bR_c$, —$C_{0-4}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{0-6}$ haloalkyl, $C_{2-6}$alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1a}$, $R_{2a}$ together with the atom to which they are attached form a $C_{3-7}$ cycloalkyl or 3- to 7-membered heterocyclyl; wherein the above groups are optionally substituted by one or more D atoms until completely deuterated;

$R_1$ and $R_{2e}$ are each independently selected from H, D, halogen, —$C_{0-4}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1c}$, $R_{2c}$ together with the atom to which they are attached form a $C_{3-7}$ cycloalkyl or 3- to 7-membered heterocyclyl; wherein the above groups are optionally substituted by one or more D atoms until completely deuterated;

$R_{1d}$ and $R_{2d}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1d}$, $R_{2d}$ together with the atom to which they are attached form a $C_{3-7}$ cycloalkyl or 3- to 7-membered heterocyclyl; wherein the above groups are optionally substituted by one or more D atoms until completely deuterated;

$R_{1f}$ and $R_{2f}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_aR_b$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-4}$ alkylene-$C_{6-10}$ aryl or —$C_{0-6}$ alkylene-5- to 10-membered heteroaryl; or $R_{1f}$, $R_{2f}$ together with the atom to which they are attached form a $C_3$, cycloalkyl or 3- to 7-membered heterocyclyl; wherein the above groups are optionally substituted by one or more D atoms until completely deuterated;

$R_{1g}$ and $R_{2g}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1g}$, $R_{2g}$ together with the atom to which they are attached form a $C_{3-7}$ cycloalkyl or 3- to 7-membered heterocyclyl; wherein the above groups are optionally substituted by one or more D atoms until completely deuterated;

$R_{1h}$ and $R_{2h}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1h}$, $R_{2h}$ together with the atom to which they are attached form a $C_{3-7}$ cycloalkyl or 3- to 7-membered heterocyclyl; wherein the above groups are optionally substituted by one or more D atoms until completely deuterated;

substituents on different atoms in —X-$(L_1)_m$-Y— can be connected to form $C_{3-10}$ cycloalkyl, 3- to 10-membered heterocyclyl, $C_{6-4}$ aryl or 3- to 10-membered heteroaryl; wherein the above groups are optionally substituted by one or more D atoms until completely deuterated;

or pharmaceutically acceptable salts, enantiomers, diastereomers, racemates, solvates, hydrates, polymorphs, prodrugs or active metabolites thereof.

In another embodiment, the present disclosure relates to the aforementioned compound, which is of formula (II'):

(II')

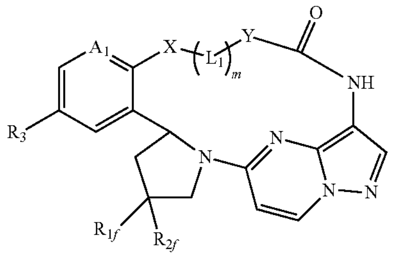

wherein, $A_1$ is selected from $CR_1$ or N;

wherein $R_1$ and $R_3$ are each independently selected from H, D, halogen, —CN, —$NO_2$, —$OR_a$, —$SR_a$, —$NR_bR_c$, $C_{1-6}$ alky, $C_{1-6}$ haloalkyl. $C_{3-7}$ cycloalkyl, 3- to 7-membered heterocyclyl, $C_{6-10}$ aryl or 5- to 10-membered heteroaryl; wherein the above groups are optionally substituted by one or more D atoms until completely deuterated;

wherein $R_a$, $R_b$ and $R_c$ are each independently selected from H, D, $C_{1-6}$ alkyl or $C_{1-6}$ haloalkyl; wherein the above groups are optionally substituted by one or more D atoms until completely deuterated;

$L_1$ is selected from C($R_{1a}$)($R_{2a}$), O, S, N($R_{1a}$), C(O), S(O) or $S(O)_2$;

X is selected from O or C($R_{1c}$)($R_{2c}$);

Y is selected from $CH_2$, CHD, $CD_2$, CH($R_{1d}$), CD($R_{1d}$) or C($R_{1d}$)($R_2$);

$R_{1a}$ and $R_{2a}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$; alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1a}$, $R_{2a}$ together with the atom to which they are attached form a $C_{3-7}$ cycloalkyl or 3- to 7-membered heterocyclyl; wherein the above groups are optionally substituted by one or more D atoms until completely deuterated;

$R_{1c}$ and $R_{2c}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1c}$, $R_{2c}$ together with the atom to which they are attached form a $C_{3-7}$ cycloalkyl or 3- to 7-membered heterocyclyl; wherein the above groups are optionally substituted by one or more D atoms until completely deuterated;

$R_{1d}$ and $R_{2d}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1d}$, $R_{2d}$ together with the atom to which they are attached form a $C_{3-7}$ cycloalkyl or 3- to 7-membered heterocyclyl; wherein the above groups are optionally substituted by one or more D atoms until completely deuterated;

$R_{1f}$ and $R_{2f}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1f}$, $R_{2f}$ together with the atom to which they are attached form a $C_{3-7}$ cycloalkyl or 3- to 7-membered heterocyclyl; wherein the above groups are optionally substituted by one or more D atoms until completely deuterated;

m is selected from 1, 2 or 3;

substituents on different atoms in —X-$(L_1)_m$-Y— can be connected to form $C_{3-10}$ cycloalkyl, 3- to 10-membered heterocyclyl, $C_{6-14}$ aryl or 3- to 10-membered heteroaryl; wherein the above groups are optionally substituted by one or more D atoms until completely deuterated;

or pharmaceutically acceptable salts, enantiomers, diastereomers, racemates, solvates, hydrates, polymorphs, prodrugs or active metabolites thereof.

In another embodiment, the present disclosure relates to the aforementioned compound, which is of formula (III'-1) or (III'-2):

(III'-1)

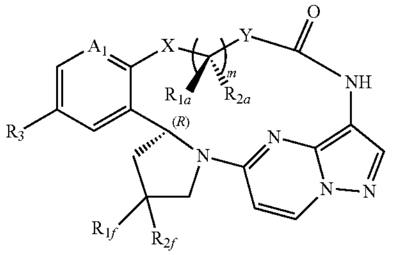

or (III'-2)

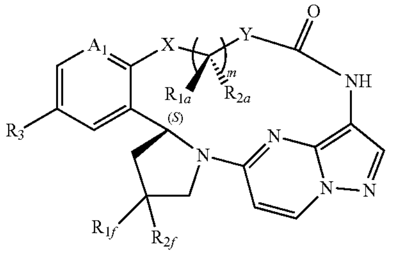

wherein,

A is selected from $CR_1$ or N;

wherein $R_1$ and $R_3$ are each independently selected from H, D, halogen, —CN, —$NO_2$, —$OR_a$, —$SR_a$, —$NR_bR_c$, $C_{0-6}$ alkyl, $C_{1-6}$ haloalkyl, $C_{3-6}$ cycloalkyl, 3- to 7-membered heterocyclyl, $C_{6-10}$ aryl or 5- to 10-membered heteroaryl; wherein the above groups are optionally substituted by one or more D atoms until completely deuterated;

wherein $R_a$, $R_b$ and Re are each independently selected from H, D, $C_{1-6}$ alkyl or $C_{1-6}$ haloalkyl; wherein the above groups are optionally substituted by one or more D atoms until completely deuterated;

X is selected from O or $C(R_c)(R_2)$;

Y is selected from $CH_2$, CHD, $CD_2$, $CH(R_{1d})$, $CD(R_{1a})$ or $C(R_a)(R_{2a})$;

$R_{1a}$ and $R_{2a}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_1$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1a}$, $R_{2a}$ together with the atom to which they are attached form a $C_{3-7}$ cycloalkyl or 3- to 7-membered heterocyclyl; wherein the above groups are optionally substituted by one or more D atoms until completely deuterated;

$R_1$ and $R_{2e}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-4}$ alkylene-$NR_bR_c$, —$C_{0-4}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1c}$, $R_{2c}$ together with the atom to which they are attached form a $C_{3-7}$ cycloalkyl or 3- to 7-membered heterocyclyl; wherein the above groups are optionally substituted by one or more D atoms until completely deuterated;

$R_{1d}$ and $R_{2d}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-4}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$ alkylene-$C_{6-10}$ aryl or —$C_{0-6}$ alkylene-5- to 10-membered heteroaryl; or $R_{1d}$. $R_{2d}$ together with the atom to which they are attached form a $C_{3-6}$ cycloalkyl or 3- to 7-membered heterocyclyl; wherein the above groups are optionally substituted by one or more D atoms until completely deuterated;

$R_1$ and $R_{2f}$ are each independently selected from H, D, halogen, —$C_{0-6}$ alkylene-CN, —$C_{0-6}$ alkylene-$OR_a$, —$C_{0-6}$ alkylene-$SR_a$, —$C_{0-6}$ alkylene-$NR_bR_c$, —$C_{0-6}$ alkylene-C(O)$R_a$, —$C_{0-6}$ alkylene-C(O)$OR_a$, —$C_{0-6}$ alkylene-C(O)$NR_bR_c$, $C_{1-6}$ alkyl, $C_{1-6}$ haloalkyl, $C_{2-6}$ alkenyl, $C_{2-6}$ alkynyl, —$C_{0-6}$ alkylene-$C_{3-6}$ cycloalkyl, —$C_{0-6}$ alkylene-3- to 7-membered heterocyclyl, —$C_{0-6}$alkylene-$C_{6-10}$ aryl or —$C_{0-6}$ alkylene-5- to 10-membered heteroaryl; or $R_{1f}$, $R_{2f}$ together with the atom to which they are attached form a $C_3$, cycloalkyl or 3- to 7-membered heterocyclyl; wherein the above groups are optionally substituted by one or more D atoms until completely deuterated;

m is selected from 1, 2 or 3;

substituents on different atoms in —X—$(C(R_{1a})(R_{2a}))_m$—Y— can be connected to form $C_{3-10}$ cycloalkyl, 3- to 10-membered heterocyclyl, $C_{6-14}$ aryl or 3- to 10-membered heteroaryl; wherein the above groups are optionally substituted by one or more D atoms until completely deuterated;

or pharmaceutically acceptable salts, enantiomers, diastereomers, racemates, solvates, hydrates, polymorphs, prodrugs or active metabolites thereof.

In another embodiment, the present disclosure relates to the aforementioned compound, which is of formula (IV'-1) or (IV'-2):

(IV'-1)

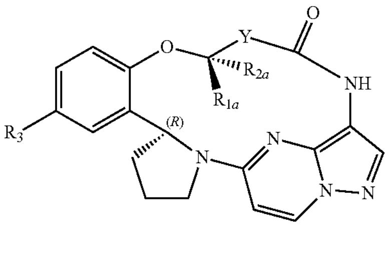

or

-continued (IV'-2)

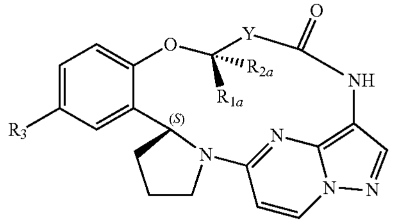

wherein, $R_3$ is selected from H, D, halogen, —CN or —$NO_2$;

$R_{1a}$ and $R_{2a}$ are each independently selected from H, D, $C_{0-6}$ alkyl or $C_{1-6}$ haloalkyl; wherein the above groups are optionally substituted by one or more D atoms until completely deuterated;

Y is selected from $CH_2$ or C(Me)(Me); wherein the above groups are optionally substituted by one or more D atoms until completely deuterated;

or pharmaceutically acceptable salts, enantiomers, diastereomers, racemates, solvates, hydrates, polymorphs, prodrugs or active metabolites thereof.

In another embodiment, the present disclosure relates to the aforementioned compound, which is of formula (V'-1 or (V'-2):

(V'-1)

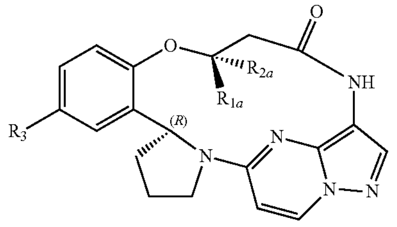

or (V'-2)

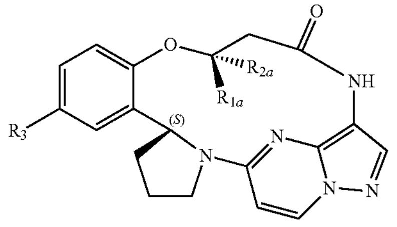

wherein, $R_3$ is selected from H, D, halogen, —CN or —$NO_2$;

$R_{1a}$ and $R_{2a}$ are each independently selected from H, D, $C_{0-6}$ alkyl or $C_{1-6}$ haloalkyl; wherein the above groups are optionally substituted by one or more D atoms until completely deuterated;

alternatively.

$R_3$ is selected from H, D, halogen, —CN or —$NO_2$;

$R_{1a}$ and $R_{2a}$ are each independently selected from H, D, $C_{0-6}$ alkyl or $C_{1-6}$ haloalkyl; $R_{1a}$ and $R_{2a}$ are not H or D at the same time; wherein the above groups are optionally substituted by one or more D atoms until completely deuterated;

or pharmaceutically acceptable salts, enantiomers, diastereomers, racemates, solvates, hydrates, polymorphs, prodrugs or active metabolites thereof.

$A_1$, $A_2$, $A_3$ and $A_4$

In a specific embodiment, $A_1$ is $CR_1$; in another specific embodiment. $A_1$ is CH; in another specific embodiment, $A_1$ is CD; in another specific embodiment, $A_1$ is N.

In a specific embodiment, $A_2$ is $CR_2$; in another specific embodiment, $A_2$ is CH; in another specific embodiment, $A_2$ is CD; in another specific embodiment, $A_2$ is N.

In a specific embodiment, $A_3$ is $CR_3$; in another specific embodiment, $A_3$ is CH; in another specific embodiment, $A_3$ is CD; in another specific embodiment, $A_3$ is CF; in another specific embodiment, $A_3$ is N.

In a specific embodiment. $A_4$ is $CR_4$; in another specific embodiment. $A_4$ is CH; in another specific embodiment, $A_4$ is CD; in another specific embodiment, $A_4$ is N.

$R_1$, $R_2$, $R_3$ and $R_4$

In a specific embodiment, $R_1$, $R_2$. $R_3$ and $R_4$ are independently H; in another specific embodiment, $R_1$, $R_2$, $R_3$ and $R_4$ are independently D; in another specific embodiment, $R_1$, $R_2$, $R_3$ and $R_4$ are independently halogen; in another specific embodiment, $R_1$, $R_2$, $R_3$ and $R_4$ are independently —CN; in another specific embodiment, $R_1$, $R_2$, $R_3$ and $R_4$ are independently —$NO_2$; in another specific embodiment, $R_1$, $R_2$, $R_3$ and $R_4$ are independently —$OR_a$; in another specific embodiment, $R_1$, $R_2$, $R_3$ and $R_4$ are independently —$SR_a$; in another specific embodiment, $R_1$, $R_2$, $R_3$ and $R_4$ are independently —$NR_bR_c$; in another specific embodiment, $R_1$, $R_2$, $R_3$ and $R_4$ are independently —C(O)R; in another specific embodiment, $R_1$, $R_2$, $R_3$ and $R_4$ are independently —C(O)OR; in another specific embodiment, $R_1$, $R_2$, $R_3$ and $R_4$ are independently —C(O)$NR_bR_c$; in another specific embodiment, $R_1$, $R_2$, $R_3$ and $R_4$ are independently —OC(O)$R_a$; in another specific embodiment, $R_1$, $R_2$, $R_3$ and $R_4$ are independently —$NR_b$C(O)$R_a$; in another specific embodiment. $R_1$, $R_2$, $R_3$ and $R_4$ are independently —S(O)$R_a$; in another specific embodiment. $R_1$, $R_2$, $R_3$ and $R_4$ are independently —$S(O)_2R_a$; in another specific embodiment, $R_1$, $R_2$, $R_3$ and $R_4$ are independently $C_{1-6}$ alkyl; in another specific embodiment, $R_1$, $R_2$, $R_3$ and $R_4$ are independently $C_{1-6}$ haloalkyl; in another specific embodiment, $R_1$, $R_2$, $R_3$ and $R_4$ are independently $C_{3-7}$ cycloalkyl; in another specific embodiment, $R_1$, $R_2$, R and $R_4$ are independently 3- to 7-membered heterocyclyl; in another specific embodiment, $R_1$, $R_2$, $R_3$ and $R_4$ are independently $C_{6-10}$ aryl; in another specific embodiment, $R_1$, $R_2$, $R_3$ and $R_4$ are independently 5- to 10-membered heteroaryl; in another specific embodiment, each group defined in $R_1$, $R_2$, $R_3$ and $R_4$ is optionally substituted by one or more D atoms until completely deuterated.

$L_1$

In a specific embodiment, $L_1$ is C($R_{1a}$)($R_{2a}$); in another specific embodiment, $L_1$ is O; in another specific embodiment, $L_1$ is S; in another specific embodiment, $L_1$ is N($R_{1a}$); in another specific embodiment, $L_1$ is C(O); in another specific embodiment, $L_1$ is S(O); in another specific embodiment, $L_1$ is $S(O)_2$.

$L_2$

In a specific embodiment, $L_2$ is C($R_{1b}$)($R_{2b}$); in another specific embodiment, $L_2$ is O; in another specific embodiment, $L_2$ is S; in another specific embodiment, $L_2$ is N($R_{1b}$); in another specific embodiment, $L_2$ is C(O); in another specific embodiment, $L_2$ is S(O); in another specific embodiment, $L_2$ is $S(O)_2$.

$L_3$

In a specific embodiment, $L_3$ is C($R_{1f}$)($R_{2f}$); in another specific embodiment, $L_3$ is O; in another specific embodiment, $L_3$ is S; in another specific embodiment, $L_3$ is N($R_{1f}$);

in another specific embodiment, $L_3$ is C(O); in another specific embodiment, $L_4$ is S(O); in another specific embodiment, $L_3$ is $S(O)_2$.

$L_4$

In a specific embodiment, $L_4$ is $C(R_{1g})(R_{2g})$; in another specific embodiment, $L_4$ is O; in another specific embodiment, $L_4$ is S; in another specific embodiment, $L_4$ is $N(R_{1g})$; in another specific embodiment, $L_4$ is C(O); in another specific embodiment, L is S(O); in another specific embodiment, $L_4$ is $S(O)_2$.

$L_5$

In a specific embodiment, $L_5$ is $C(R_{1h})(R_{2h})$; in another specific embodiment, $L_5$ is O; in another specific embodiment, $L_5$ is S; in another specific embodiment, $L_5$ is $N(R_{1h})$; in another specific embodiment, $L_5$ is C(O); in another specific embodiment, $L_5$ is S(O); in another specific embodiment, $L_5$ is $S(O)_2$.

X

In a specific embodiment, X is O; in another specific embodiment, X is S; in another specific embodiment, X is $N(R_{1c})$; in another specific embodiment, X is $C(R_{1c})(R_{2c})$.

Y

In a specific embodiment, Y is O; in another specific embodiment, Y is S; in another specific embodiment, Y is $N(R_{1d})$; in another specific embodiment. Y is $C(R_{1d})(R_{2d})$.

W

In a specific embodiment, W is O; in another specific embodiment, W is S; in another specific embodiment, W is $N(R_{1e})$; in another specific embodiment, W is $C(R_{1c})(R_{2c})$.

R

In a specific embodiment, R is H; in another specific embodiment, R is D; in another specific embodiment, R is $C_{1-6}$ alkyl; in another specific embodiment, R is $C_{1-6}$ haloalkyl; in another specific embodiment, R is $C_{3-7}$ cycloalkyl; in another specific embodiment, R is 3- to 7-membered heterocyclyl; in another specific embodiment, R is $C_{6-10}$ aryl; in another specific embodiment, R is 5- to 10-membered heteroaryl; in another specific embodiment, each group defined in R is optionally substituted by one or more D atoms until completely deuterated.

m

In a specific embodiment, m is 1; in another specific embodiment, m is 2; in another specific embodiment, m is 3; in another specific embodiment, m is 4; in another specific embodiment, m is 5.

n

In a specific embodiment, n is 1; in another specific embodiment, n is 2; in another specific embodiment, n is 3.

$R_{1a}$ and $R_{2a}$, $R_{1b}$ and $R_{2b}$, $R_{1c}$ and $R_{2c}$, $R_{1d}$ and $R_{2e}$, $R_{1e}$ and $R_{2e}$, $R_{1f}$ and $R_{2f}$, $R_{1g}$ and $R_{2g}$, $R_{1h}$ and $R_{2h}$ In a specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently H; in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently D; in another specific embodiment, $R_{1a}$ and $R_{2a}/R_{1b}$ and $R_{2b}/R_{1c}$ and $R_{2c}/R_{1a}$ and $R_{2d}/R_{1e}$ and $R_{2e}/R_{1f}$ and $R_{2f}/R_{1g}$ and $R_{2g}/R_{1h}$ and $R_{2h}$ are independently halogen; in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently —$C_{0-6}$ alkylene-CN; in another specific embodiment, $R_{1a}$ and $R_{2a}/R_{1b}$ and $R_{2b}/R_{1c}$ and $R_{2b}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently —$C_{0-6}$ alkylene-$OR_a$; in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently —$C_{0-6}$ alkylene-$SR_a$; in another specific embodiment. $R_{1a}$ and $R_{2a}/R_{1b}$ and $R_{2b}/R_{1c}$ and $R_{2c}/R_{1d}$ and $R_{2d}/R_{1e}$, and $R_{2e}/R_{1f}$ and $R_{2f}/R_{1g}$ and $R_{2g}/R_{1h}$ and $R_{2h}$ are independently —$C_{0-6}$ alkylene-$NR_bR_c$; in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently —$C_{0-6}$ alkylene-C(O)$R_a$; in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently —$C_{0-6}$ alkylene-C(O)$OR_a$; in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently —$C_{0-6}$ alkylene-C(O)$NR_bR_c$; in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently $C_{1-6}$ alkyl; in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently $C_{1-6}$ haloalkyl; in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently $C_{2-4}$ alkenyl; in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently $C_{2f}$ alkynyl; in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently —$C_{0-6}$ alkylene-$C_{3-6}$ cycloalkyl in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently —$C_{0-6}$ alkylene-3- to 7-membered heterocyclyl; in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ are independently —$C_{0-6}$ alkylene-$C_{6-10}$ aryl; in another specific embodiment. $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ and $R_{2d}$ are independently —$C_{0-6}$ alkylene-5- to 10-membered heteroaryl; in another specific embodiment, $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$, together with the atom to which they are attached form a $C_{3-7}$ cycloalkyl; in another specific embodiment. $R_{1a}$ and $R_{2a}/R_{1b}$ and $R_{2b}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$, together with the atom to which they are attached form a 3- to 7-membered heterocyclyl; in another specific embodiment, each group defined in $R_{1a}$ and $R_{2a}/R_{1b}$ and $R_{2d}/R_{1c}$ and $R_{2c}/R_{1d}$ and $R_{2d}/R_{1e}$ and $R_{2e}/R_{1f}$ and $R_{2f}/R_{1g}$ and $R_{2g}/R_{1h}$ and $R_{2h}$ is optionally substituted by one or more D atoms until completely deuterated.

Substituents on different atoms in —X-$(L_1)_m$-Y— can be connected to form $C_{3-10}$ cycloalkyl, 3- to 10-membered heterocyclyl, $C_{6-14}$ aryl or 3- to 10-membered heteroaryl. In a specific embodiment, substituents on different atoms in —X-$(L_1)_m$-Y— can be connected to form $C_{3-10}$ cycloalkyl; in another specific embodiment, substituents on different atoms in —X-$(L)_m$-Y— can be connected to form 3- to 10-membered heterocyclyl; in another specific embodiment, substituents on different atoms in —X-$(L_1)_m$-Y— can be connected to form $C_{6-14}$ aryl; in another specific embodiment, substituents on different atoms in —X-$(L_1)_m$-Y— can be connected to form 3- to 10-membered heteroaryl; in another specific embodiment, the formed $C_{3-10}$ cycloalkyl, 3- to 10-membered heterocyclyl, $C_{6-14}$ aryl or 3- to 10-membered heteroaryl is optionally substituted by one or more D atoms until completely deuterated.

Substituents on different atoms in -$(L_2)_n$-W— can be connected to form $C_{3-10}$ cycloalkyl, 3- to 10-membered heterocyclyl, $C_{6-14}$ aryl or 3- to 10-membered heteroaryl. In a specific embodiment, substituents on different atoms in $-(L_2)_n$-W— can be connected to form $C_{3-10}$ cycloalkyl; in another specific embodiment, substituents on different atoms in $-(L_2)_n$-W— can be connected to form 3- to 10-membered heterocyclyl; in another specific embodiment, substituents on different atoms in $-(L_2)_n$-W— can be connected to form $C_{6-4}$ aryl; in another specific embodiment, substituents on different atoms in $-(L_2)_n$-W— can be connected to form 3- to 10-membered heteroaryl; in another specific embodiment, the formed $C_{3-10}$ cycloalkyl, 3- to 10-membered heterocyclyl, $C_{6-14}$ aryl or 3- to 10-membered heteroaryl is optionally substituted by one or more D atoms until completely deuterated.

Substituents on different atoms in $-L_5-(L_3)_n-L_4$- can be connected to form $C_{3-10}$ cycloalkyl, 3- to 10-membered heterocyclyl, $C_{6-14}$ aryl or 3- to 10-membered heteroaryl. In a specific embodiment, substituents on different atoms in $-L_5-(L_3)_n-L_4$- can be connected to form $C_{3-10}$ cycloalkyl; in another specific embodiment, substituents on different atoms in $-L_5-(L_3)_n-L_4$- can be connected to form 3- to 10-membered heterocyclyl; in another specific embodiment, substituents on different atoms in $-L_5-(L_3)_n-L_4$- can be connected to form $C_{6-14}$ aryl; in another specific embodiment, substituents on different atoms in $-L_5-(L_3)_n-L_4$- can be connected to form 3- to 10-membered heteroaryl; in another specific embodiment, the formed $C_{3-10}$ cycloalkyl, 3- to 10-membered heterocyclyl, $C_{6-14}$ aryl or 3- to 10-membered heteroaryl is optionally substituted by one or more D atoms until completely deuterated.

For example, when —X-$(L_1)_m$-Y— represents —C($R_{1c}$)($R_{2c}$)—C($R_a$)($R_{2a}$)—C($R_{1d}$)($R_{2d}$)—, $R_{1e}$ or $R_{2e}$ on the first carbon atom can form a ring with $R_{1a}$ or $R_{2a}$ on the second carbon atom, or $R_{1c}$ or $R_{2e}$ on the first carbon atom can form a ring with $R_{1d}$ or $R_{2d}$ on the third carbon atom, or $R_{1a}$ or $R_{2a}$ on the second carbon atom can form a ring with $R_{1d}$ or $R_{2d}$ on the third carbon atom. For another example, when $-(L_2)_n$-W— represents —C($R_{1b}$)($R_{2b}$)—C($R_{1b}$)($R_{2b}$)—N($R_{1c}$)—, $R_{1b}$ or $R_{2b}$ on the first carbon atom can form a ring with $R_{1b}$ or $R_{2b}$ on the second carbon atom, or $R_{1b}$ or $R_{2b}$ on the first carbon atom can form a ring with $R_{1e}$ on the third nitrogen atom, or $R_{1b}$ or $R_{2b}$ on the second carbon atom can form a ring with $R_{1e}$ on the third nitrogen atom.

Any technical solution or any combination thereof of the above specific embodiments can be combined with any technical solution or any combination thereof of other specific embodiments. For example, any technical solution or any combination thereof of $A_1$ can be combined with any technical solution or any combination thereof of $A_1$-$A_4$, $R_1$-$R_4$, X, Y, W, R, $L_1$-$L_5$, m and n. The present disclosure is intended to include a combination of all these technical solutions, limited to space, these technical solutions will not be listed one by one.

In another embodiment, the compound of the present disclosure may be selected from the following compounds:

T-1

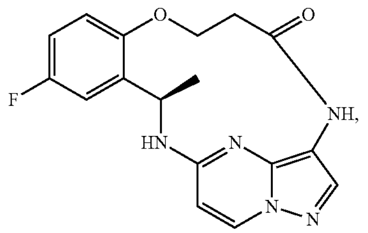

-continued

T-2-A

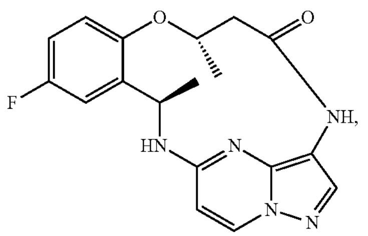

T-2-B

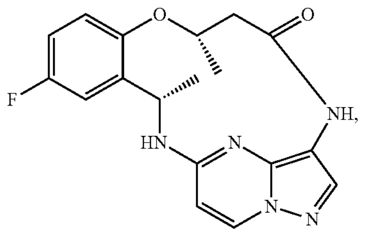

T-3

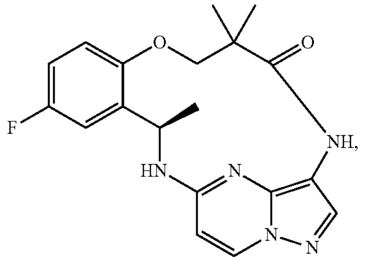

T-4

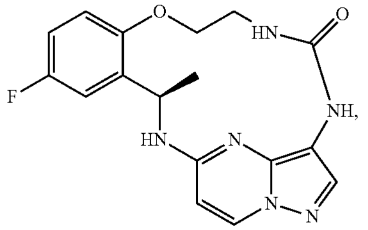

T-5

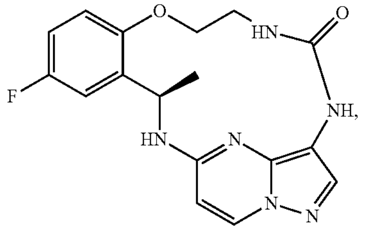

T-6

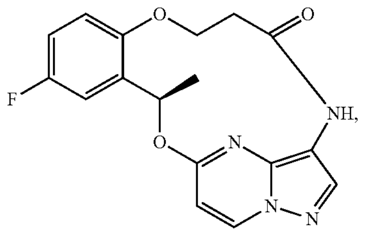

-continued
L-1-A
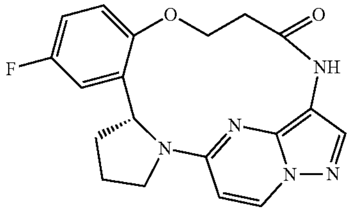,
L-1-B
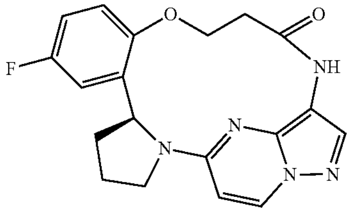,
9a
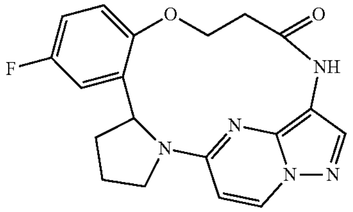,
L-2-A
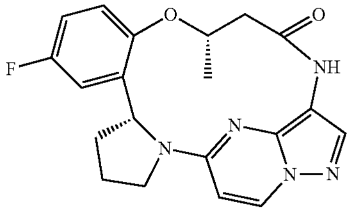,
L-2-B
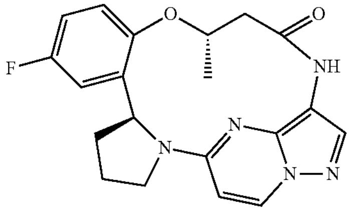,
13a
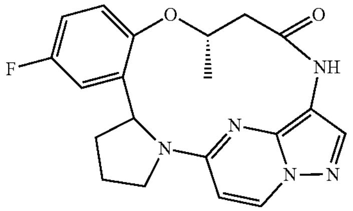,
L-3-A
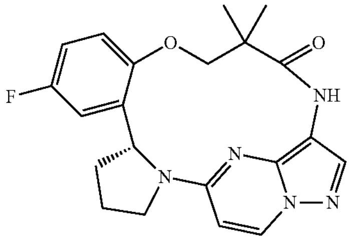,
-continued
L-3-B
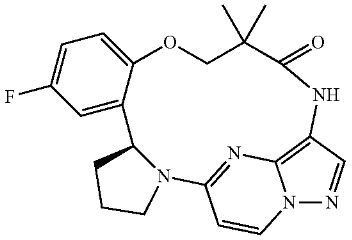,
18a
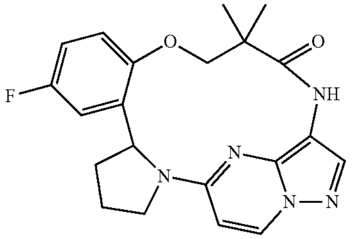,
23a
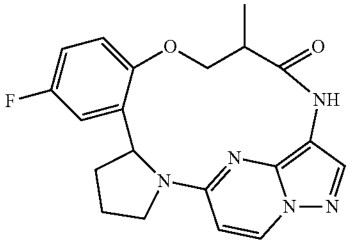,
L-4-A
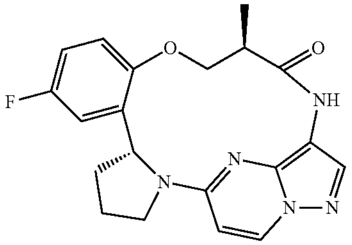,
L-4-B
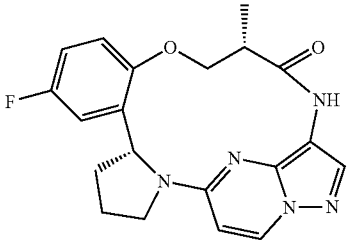,
L-4-C
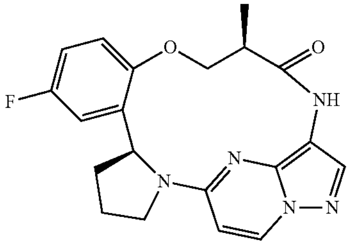, -continued
L-4-D
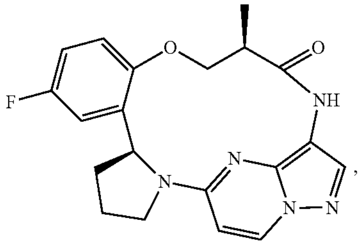
28a
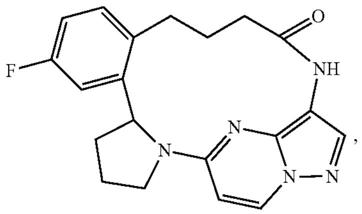
L-5-A
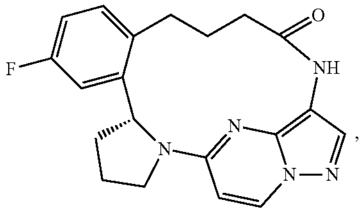
L-5-B
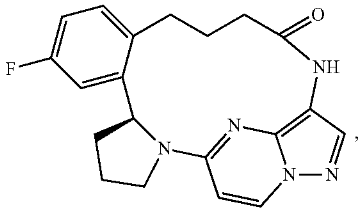
32a
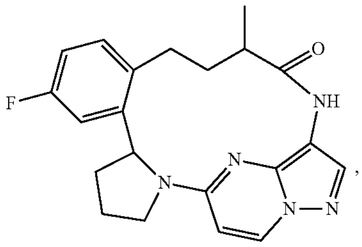
L-6-A
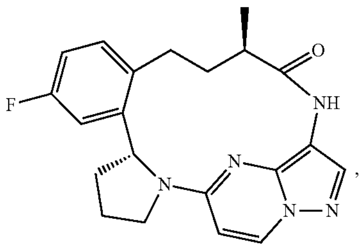
-continued
L-6-B
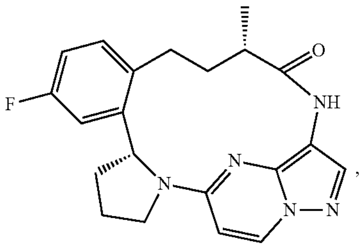
L-6-C
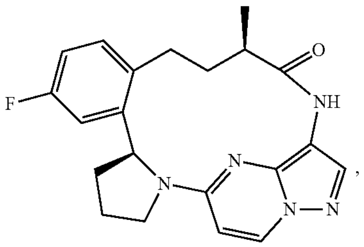
L-6-D
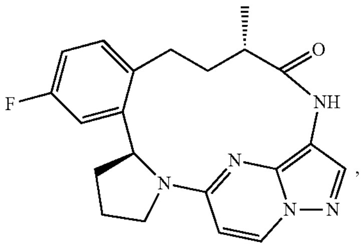
41a
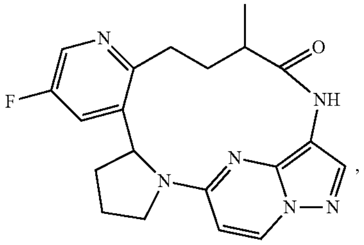
L-7-A
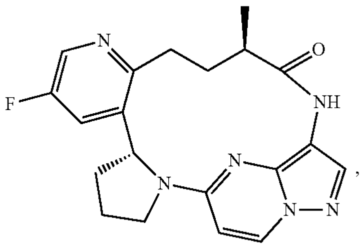
L-7-B
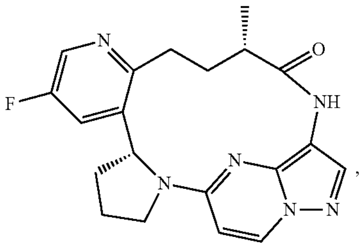

-continued

L-7-C

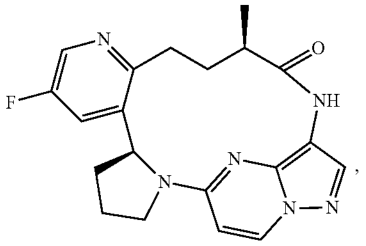

L-7-D

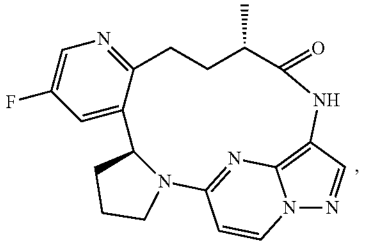

45a

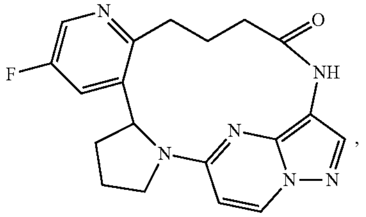

L-8-A

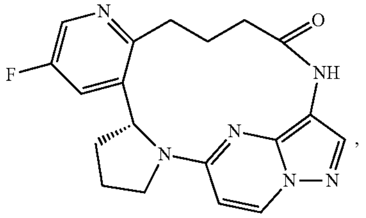

L-8-B

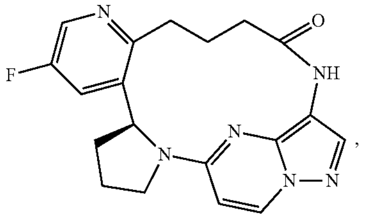

56a

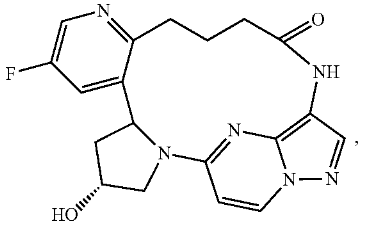

-continued

L-9-A

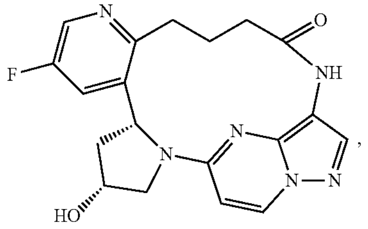

L-9-B

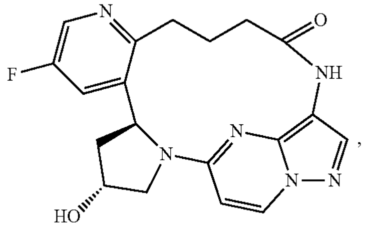

64a

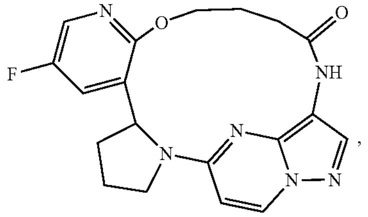

L-10-A

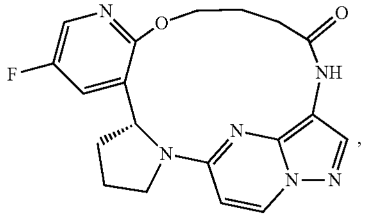

L-10-B

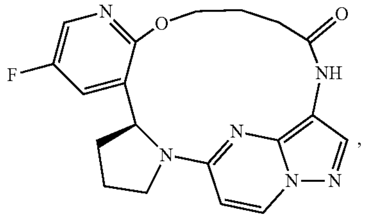

or pharmaceutically acceptable salts, enantiomers, diastereomers, racemates, solvates, hydrates, polymorphs, prodrugs or active metabolites thereof.

The compounds of the present disclosure may include one or more asymmetric centers, and thus may exist in a variety of stereoisomeric forms, for example, enantiomers and/or diastereomers. For example, the compounds of the present disclosure may be in the form of an individual enantiomer, diastereomer or geometric isomer (e.g., cis- and trans-isomers), or may be in the form of a mixture of stereoisomers, including racemic mixture and a mixture enriched in one or more stereoisomers. The isomers can be separated from the mixture by the methods known to those skilled in the art, including chiral high pressure liquid chromatography (HPLC) and the formation and crystallization of chiral salts; or preferred isomers can be prepared by asymmetric synthesis.

It will be understood by those skilled in the art that the organic compounds can form complexes with solvents in which they are reacted or from which they are precipitated or crystallized. These complexes are known as "solvates." Where the solvent is water, the complex is known as "hydrate." The present disclosure encompasses all solvates of the compounds of the present disclosure.

The term "solvate" refers to forms of a compound or a salt thereof, which are associated with a solvent, usually by a solvolysis reaction. This physical association may include hydrogen bonding. Conventional solvents include water, methanol, ethanol, acetic acid, DMSO, THF, diethyl ether, etc. The compounds described herein can be prepared, for example, in crystalline form, and can be solvated. Suitable solvates include pharmaceutically acceptable solvates and further include both stoichiometric solvates and non-stoichiometric solvates. In some cases, the solvates will be capable of isolation, for example, when one or more solvent molecules are incorporated into the crystal lattice of a crystalline solid. "Solvate" includes both solution-phase and isolatable solvates. Representative solvates include hydrates, ethanolates and methanolates.

The term "hydrate" refers to a compound that is associated with water. Generally, the number of water molecules contained in a hydrate of a compound is in a definite ratio to the number of the compound molecules in the hydrate. Therefore, hydrates of a compound can be represented, for example, by a general formula R.x $H_2O$, wherein R is the compound, and x is a number greater than 0. Given compounds can form more than one type of hydrates, including, for example, monohydrates (x is 1), lower hydrates (x is a number greater than 0 and smaller than 1, for example, hemihydrates (R.x $H_2O$)) and polyhydrates (x is a number greater than 1, for example, dihydrates (R.2$H_2O$) and hexahydrates (R.6$H_2O$)).

Compounds of the present disclosure may be in an amorphous or a crystalline form (polymorph). Furthermore, the compounds of the present disclosure may exist in one or more crystalline forms. Therefore, the present disclosure includes all amorphous or crystalline forms of the compounds of the present disclosure within its scope. The term "polymorph" refers to a crystalline form of a compound (or a salt, hydrate or solvate thereof) in a particular crystal packing arrangement. All polymorphs have the same elemental composition. Different crystalline forms generally have different X-ray diffraction patterns, infrared spectra, melting points, density, hardness, crystal shapes, optical and electrical properties, stability, and solubility. Recrystallization solvents, rate of crystallization, storage temperatures, and other factors may cause one crystalline form to dominate. Various polymorphs of a compound can be prepared by crystallization under different conditions.

The present disclosure also comprises compounds that are labeled with isotopes, which are equivalent to those described in formula (I), but one or more atoms are replaced by atoms having an atom mass or mass number that are different from that of atoms that are common in nature. Examples of isotopes which may be introduced into the compounds of the disclosure include isotopes of hydrogen, carbon, nitrogen, oxygen, phosphorus, sulfur, fluorine and chlorine, such as $^{2}H$, $^{3}H$, $^{13}C$, $^{11}C$, $^{14}C$, $^{15}N$, $^{18}O$, $^{17}O$, $^{31}P$, $^{32}P$, $^{35}S$, $^{18}F$ and $^{36}Cl$, respectively. Compounds of the present disclosure that comprise the above isotopes and/or other isotopes of other atoms, prodrugs thereof and pharmaceutically acceptable salts of said compounds or prodrugs all are within the scope of the present disclosure. Certain isotope-labeled compounds of the present disclosure, such as those incorporating radioactive isotopes (e.g., $^{3}H$ and $^{14}C$), can be used for the measurement of the distribution of drug and/or substrate in tissue. Tritium, which is $^{1}H$ and carbon-14, which is $^{14}C$ isotope, are particularly preferred, because they are easy to prepare and detect. Furthermore, replaced by heavier isotopes, such as deuterium, which is $^{2}H$, may provide therapeutic benefits due to the higher metabolic stability, such as prolonging the half-life in vivo or decreasing the dosage requirements, and thus may be preferred in some cases. Isotope-labeled compounds of formula (I) of the present disclosure and prodrugs thereof can be prepared generally by using readily available isotope-labeled reagents to replace non-isotope-labeled reagents in the following schemes and/or the procedures disclosed in the examples and preparation examples.

In addition, prodrugs are also included within the context of the present disclosure. The term "prodrug" as used herein refers to a compound that is converted into an active form that has medical effects in vivo by, for example, hydrolysis in blood. Pharmaceutically acceptable prodrugs are described in T. Higuchi and V. Stella, Prodrugs as Novel Delivery Systems, A.C.S. Symposium Series, Vol. 14, Edward B. Roche, ed., Bioreversible Carriers in Drug Design. American Pharmaceutical Association and Pergamon Press, 1987, and D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

The prodrugs are any covalently bonded compounds of the present disclosure, which release the parent compound in vivo when the prodrug is administered to a patient. Prodrugs are typically prepared by modifying functional groups in such a way that the modifications can be cleaved either by routine manipulation or decompose in vivo to yield the parent compound. Prodrugs include, for example, compounds of the present disclosure wherein the hydroxyl, amino or sulfhydryl groups are bonded to any group that, when administered to a patient, cleaves to form the hydroxyl, amino or sulfhydryl groups. Thus, representative examples of prodrugs include (but are not limited to) the acetate/acetamide, formate/formamide and benzoate/benzamide derivatives of the hydroxyl, amino or sulfhydryl functional groups of the compounds of formula (I). Furthermore, in the case of carboxylic acid (—COOH), esters such as methyl esters and ethyl esters, etc. can be employed. The ester itself may be active in their own and/or hydrolyzable under in vivo conditions in the human body. Suitable pharmaceutically acceptable in vivo hydrolysable ester groups include those groups that can readily break down in the human body to release the parent acids or salts thereof.

Pharmaceutical Compositions, Formulations and Kits

In another aspect, the disclosure provides a pharmaceutical composition comprising a compound of the present disclosure (also referred to as the "active ingredient") and a pharmaceutically acceptable excipient. In certain embodiments, the pharmaceutical composition comprises an effective amount of the active ingredient. In certain embodiments, the pharmaceutical composition comprises a therapeutically effective amount of the active ingredient. In certain embodiments, the pharmaceutical composition comprises a prophylactically effective amount of the active ingredient.

A pharmaceutically acceptable excipient for use in the present disclosure refers to a non-toxic carrier, adjuvant or vehicle which does not destroy the pharmacological activity of the compound formulated together. Pharmaceutically acceptable carriers, adjuvants, or vehicles that may be used in the compositions of the present disclosure include, but are not limited to, ion exchangers, alumina, aluminum stearate, lecithin, serum proteins (e.g., human serum albumin), buffer substances (such as phosphate), glycine, sorbic acid, potassium sorbate, a mixture of partial glycerides of saturated plant fatty acids, water, salt or electrolyte (such as protamine sulfate), disodium hydrogen phosphate, potassium hydrogen phosphate, sodium chloride, zinc salt, silica gel, magnesium trisilicate, polyvinyl pyrrolidone, cellulose-based materials, polyethylene glycol, sodium carboxymethyl cellulose, polyacrylate, wax, polyethylene-polyoxypropylene block polymers, polyethylene glycol and lanolin.

The present disclosure also includes kits (e.g., pharmaceutical packs). Kits provided may include a compound disclosed herein, other therapeutic agents, and a first and a second containers (e.g., vials, ampoules, bottles, syringes, and/or dispersible packages or other materials) containing the compound disclosed herein or other therapeutic agents. In some embodiments, kits provided can also optionally include a third container containing a pharmaceutically acceptable excipient for diluting or suspending the compound disclosed herein and/or other therapeutic agent. In some embodiments, the compound disclosed herein provided in the first container and the other therapeutic agents provided in the second container is combined to form a unit dosage form.

The pharmaceutical composition provided by the present disclosure may be administered by a variety of routes including, but not limited to, oral administration, parenteral administration, inhalation administration, topical administration, rectal administration, nasal administration, oral administration, vaginal administration, administration by implant or other means of administration. For example, parenteral administration as used herein includes subcutaneous administration, intradermal administration, intravenous administration, intramuscular administration, intra-articular administration, intraarterial administration, intrasynovial administration, intrasternal administration, intracerebroventricular administration, intralesional administration, and intracranial injection or infusion techniques.

Generally, the compounds provided herein are administered in an effective amount. The amount of the compound actually administered will typically be determined by a physician, in the light of the relevant circumstances, including the condition to be treated, the chosen route of administration, the actual compound administered, the age, weight, and response of the individual patient, the severity of the patient's symptoms, and the like.

When used to prevent the disorder disclosed herein, the compounds provided herein will be administered to a subject at risk for developing the condition, typically on the advice and under the supervision of a physician, at the dosage levels described above. Subjects at risk for developing a particular condition generally include those that have a family history of the condition, or those who have been identified by genetic testing or screening to be particularly susceptible to developing the condition.

The pharmaceutical compositions provided herein can also be administered chronically ("chronic administration"). Chronic administration refers to administration of a compound or pharmaceutical composition thereof over an extended period of time, e.g., for example, over 3 months, 6 months, 1 year, 2 years, 3 years, 5 years, etc, or may be continued indefinitely, for example, for the rest of the subject's life. In certain embodiments, the chronic administration is intended to provide a constant level of the compound in the blood, e.g., within the therapeutic window over the extended period of time.

The pharmaceutical compositions of the present disclosure may be further delivered using a variety of dosing methods. For example, in certain embodiments, the pharmaceutical composition may be given as a bolus, e.g., in order to raise the concentration of the compound in the blood to an effective level rapidly. The placement of the bolus dose depends on the desired systemic levels of the active ingredient. e.g., an intramuscular or subcutaneous bolus dose allows a slow release of the active ingredient, while a bolus delivered directly to the veins (e.g., through an IV drip) allows a much faster delivery which quickly raises the concentration of the active ingredient in the blood to an effective level. In other embodiments, the pharmaceutical composition may be administered as a continuous infusion, e.g., by IV drip, to provide maintenance of a steady-state concentration of the active ingredient in the subject's body. Furthermore, in still yet other embodiments, the pharmaceutical composition may be administered as first as a bolus dose, followed by continuous infusion.

The compositions for oral administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules or the like in the case of solid compositions. In such compositions, the compound is usually a minor component (from about 0.1 to about 50% by weight or alternatively from about 1 to about 40% by weight) with the remainder being various vehicles or excipients and processing aids helpful for forming the desired dosing form.

With oral dosing, one to five and especially two to four and typically three oral doses per day are representative regimens. Using these dosing patterns, each dose provides from about 0.01 to about 20 mg/kg of the compound provided herein, with preferred doses each providing from about 0.1 to about 10 mg/kg, and especially about 1 to about 5 mg/kg.

Transdermal doses are generally selected to provide similar or lower blood levels than are achieved using injection doses, generally in an amount ranging from about 0.01 to about 20% by weight, alternatively from about 0.1 to about 20% by weight, alternatively from about 0.1 to about 10% by weight, and yet alternatively from about 0.5 to about 15% by weight.

Injection dose levels range from about 0.1 mg/kg/hour to at least 10 mg/kg/hour, all for from about 1 to about 120 hours and especially 24 to 96 hours. A preloading bolus of from about 0.1 mg/kg to about 10 mg/kg or more may also be administered to achieve adequate steady state levels. The maximum total dose is not expected to exceed about 2 g/day for a 40 to 80 kg human patient.

Liquid forms suitable for oral administration may include a suitable aqueous or nonaqueous vehicle with buffers, suspending and dispensing agents, colorants, flavors and the like. Solid forms may include, for example, any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate; a glidant such as colloidal silicon dioxide; a sweetening agent such as sucrose or saccharin; or a flavoring agent such as peppermint, methyl salicylate, or orange flavoring.

Injectable compositions are typically based upon injectable sterile saline or phosphate-buffered saline or other injectable excipients known in the art. As before, the active compound in such compositions is typically a minor component, often being from about 0.05 to 10% by weight with the remainder being the injectable excipient and the like.

Transdermal compositions are typically formulated as a topical ointment or cream containing the active ingredient(s). When formulated as a ointment, the active ingredients will typically be combined with either a paraffinic or a water-miscible ointment base. Alternatively, the active ingredients may be formulated in a cream with, for example an oil-in-water cream base. Such transdermal formulations are well-known in the art and generally include additional ingredients to enhance the dermal penetration of stability of the active ingredients or Formulation. All such known transdermal formulations and ingredients are included within the scope provided herein.

The compounds provided herein can also be administered by a transdermal device. Accordingly, transdermal administration may be accomplished using a patch either of the reservoir or porous membrane type, or of a solid matrix variety.

The above-described components for orally administrable, injectable or topically administrable compositions are merely representative. Other materials as well as processing techniques and the like are set forth in Part 8 of Remington's Pharmaceutical Sciences, 17th edition, 1985, Mack Publishing Company, Easton, Pa., which is incorporated herein by reference.

The compounds of the present disclosure can also be administered in sustained release forms or from sustained release drug delivery systems. A description of representative sustained release materials may be found in Remington's Pharmaceutical Sciences.

The present disclosure also relates to the pharmaceutically acceptable formulations of a compound of the present disclosure. In one embodiment, the formulation comprises water. In another embodiment, the formulation comprises a cyclodextrin derivative. The most common cyclodextrins are α-, β- and γ-cyclodextrins consisting of 6, 7 and 8 α-1,4-linked glucose units, respectively, optionally comprising one or more substituents on the linked sugar moieties, which include, but are not limited to, methylated, hydroxyalkylated, acylated, and sulfoalkylether substitution. In certain embodiments, the cyclodextrin is a sulfoalkyl ether β-cyclodextrin, e.g., for example, sulfobutyl ether β-cyclodextrin, also known as Captisol. See, e.g., U.S. Pat. No. 5,376,645. In certain embodiments, the formulation comprises hexapropyl-β-cyclodextrin (e.g., 10-50% in water).

Indications

Exemplary diseases include cancer, pain, neurological diseases, autoimmune diseases, and inflammation. Cancers include, for example, lung cancer, colon cancer, breast cancer, prostate cancer, hepatocellular carcinoma, renal cell carcinoma, gastric and esophageal cancer, glioblastoma, head and neck cancer, inflammatory myofibroblastic tumor and anaplastic large cell lymphoma. Pain includes, for example, pain of any source or cause, including cancer pain, chemotherapy pain, nerve pain, injury pain or pain from other sources. Autoimmune diseases include, for example, rheumatoid arthritis, Sjogren syndrome, type I diabetes and lupus. Exemplary neurological diseases include Alzheimer's disease, Parkinson's disease, amyotrophic lateral sclerosis and Huntington's disease. Exemplary inflammatory diseases include atherosclerosis, allergies, and inflammation due to infection or injury.

In one aspect, the compounds and pharmaceutical compositions of the present disclosure specifically target tyrosine receptor kinases, especially ALK, ROS1 and TRK. Therefore, the compounds and pharmaceutical compositions can be used to prevent, reverse, alleviate or inhibit the activity of one or more of the kinases. In a preferred embodiment, the method of treatment targets cancer. In other embodiments, the method is used to treat lung cancer or non-small cell lung cancer.

In the inhibition method of the present disclosure, "effective amount" is intended to mean an amount effective to inhibit the target protein. The measurement and adjustment of targets can be implemented by conventional analytical methods (such as those described below). The adjustment can be used in a variety of settings, including in vitro analysis. In the said methods, the cells are preferably cancer cells with abnormal signal transduction due to the up-regulation of ALK, ROS1 and TRK.

In the treatment method of the present disclosure, "effective amount" is intended to refer to an amount or dosage sufficient to produce the desired therapeutic benefit in an individual in need of the treatment. The effective amount or dosage of the compounds of the present disclosure can be determined by conventional methods (e.g., modeling, dose escalation or clinical trials) and conventional factors (e.g., the mode or route of drug delivery, the pharmacokinetics of the drug, the severity and process of the infection, the individual's health and weight, and the judgment of the attending physician). Exemplary dosages are in the range of about 0.1 mg to 1 g per day, or about 1 mg to 50 mg per day, or about 50 mg to 250 mg per day or about 250 mg to 1 g per day. The total dosage can be in a single or separated dose units (e.g., BID, TID, QID).

After the patient's disease has improved, the dosage can be adjusted for preventive or maintenance treatment. For example, the dosage or frequency of administration or both can be reduced according to symptoms to an amount of maintaining the required therapeutic or preventive effect. Of course, if the symptoms have been reduced to an appropriate level, then the treatment can be stopped. However, when any symptom recurs, patients may require long-term intermittent treatment. Patients may also require long-term chronic treatment.

Drug Combination

The compounds described herein can be used in combination with one or more other active ingredients in pharmaceutical compositions or methods to treat the diseases and disorders described herein. Other additional active ingredients include other therapeutic agents or drugs that alleviate the adverse effects of the therapeutic agent on the expected disease target. The combination can be used to increase efficacy, improve symptoms of other diseases, reduce one or more negative effects, or reduce the required dosage of the compound of the present disclosure. Additional active ingredients can be formulated into a pharmaceutical composition separated from that of the compounds of the present disclosure or can be included in a single pharmaceutical composition with the compounds of the present disclosure. The additional active ingredient can be administered simultaneously with, before or after the administration of the compound of the present disclosure.

Combination agents include those additional active ingredients that known or observed to be effective in the treatment of the diseases and conditions described herein, including those effectively against another target related to the disease. For example, the compositions and formulations of the present disclosure, and treatment methods may further include other drugs or medicines, such as other active agents that can be used to treat or alleviate the target disease or related symptoms or conditions. For cancer indications, other such agents include, but are not limited to, kinase inhibitors, for example, EGFR inhibitors (such as erlotinib, gefitinib); Raf inhibitors (such as vemurafenib), VEGFR inhibitors (such as sunitinib); standard chemotherapeutic agents such as alkylating agents, antimetabolites, antitumor antibiotics, topoisomerase inhibitors, platinum drugs, mitotic inhibitors, antibodies, hormone therapy or corticosteroids. For pain indications, suitable combination agents include anti-inflammatory agents, such as NSAID. The pharmaceutical composition of the present disclosure may additionally include one or more of the active agents, and the method of treatment may additionally include administering an effective amount of one or more of the active agents.

EXAMPLES

The present disclosure will be further described below in combination with specific embodiments. It should be understood that these examples are only used to illustrate the present disclosure and not to limit the scope of the present disclosure. The experimental methods without specific conditions in the following examples generally follow the conventional conditions or the conditions recommended by the manufacturer. Unless otherwise stated, parts and percentages are parts by weight and weight percent.

Generally, in the preparation process, each reaction is carried out in an inert solvent at a temperature from room temperature to reflux temperature (such as 0° C. to 100° C., alternatively 0° C. to 80° C.). The reaction time is usually 0.1-60 hours, alternatively 0.5-24 hours.

Example 1: Preparation of (13R)-11-fluoro-13-methyl-6,7,13,14-tetrahydro-1,15-ethenopyrazolo[4,3-f][1,4,8,10]benzoxatriazacyclotridecin-5(6H)-one (Compound T-1)

T-1

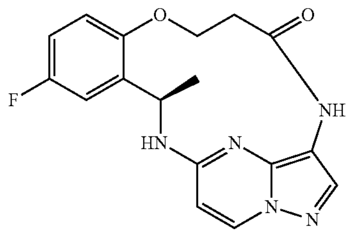

The following route was used for the synthesis:

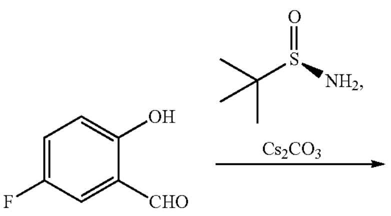

-continued

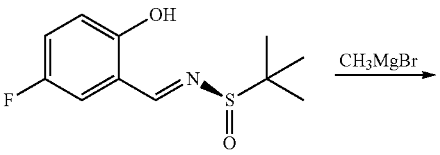

1

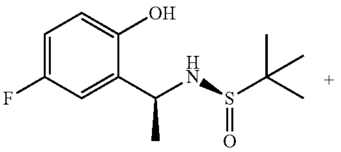

2

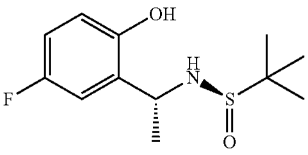

3

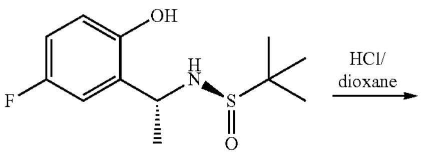

3

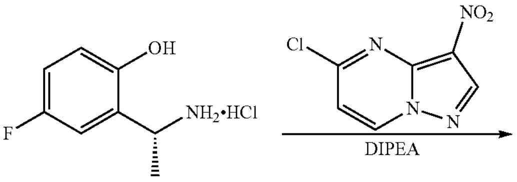

4

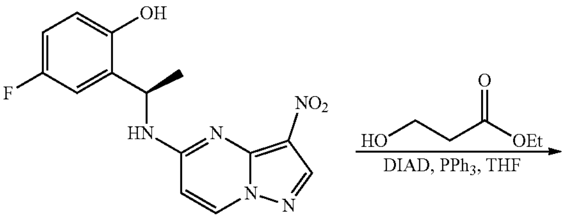

5

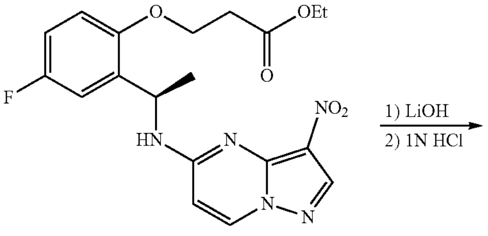

6

-continued

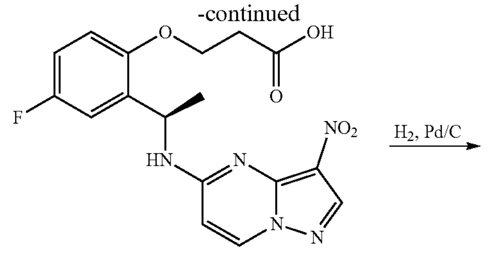

7

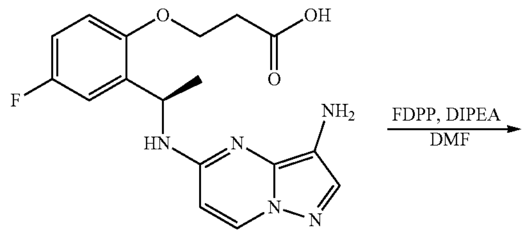

8

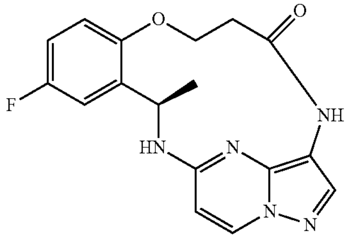

T-1

Step 1 Synthesis of Compound 1

5-fluoro-2-hydroxybenzaldehyde (1.4 g, 10.0 mmol), and R-tert-butylsulfinamide (1.21 g, 10.0 mmol) were added to a reaction flask, which were dissolved in 20 ml dichloromethane, cesium carbonate was added (5.21 g, 16.0 mmol), and the reaction was stirred at room temperature for 18 hours under nitrogen protection. The reaction was quenched by adding an excess amount of water, and extracted 3-4 times with dichloromethane. The organic phases were combined, washed with saturated brine, concentrated, purified by column chromatography, and dried in vacuum to afford 2.11 g of the product. Yield: 86.8%.

Step 2 Synthesis of Compounds 2 and 3

Compound 1 (1.86 g, 7.67 mmol) was added to a reaction flask, which was dissolved by adding 25 ml of anhydrous terahydrofuran, and a solution of 3M methylmagnesium bromide in anhydrous tetrahydrofuran (12.8 ml, 38.4 mmol) was slowly added at −65° C. After the addition, the reaction was warmed to room temperature and stirred overnight. TLC was used to monitor the completion of the reaction. 20 ml of water was added dropwise to quench the reaction in an ice bath, the organic phase was separated, and the aqueous phase was extracted with ethyl acetate for 3-4 times. The organic phases were combined, washed with saturated brine, concentrated and then purified by silica gel column chromatography (petroleum ether:ethyl acetate=2:1) to afford 0.98 g of compound 2 and 1.1 g of compound 3. Yield: 100%.

Step 3 Synthesis of Compound 4

Compound 3 (1.14 g, 4.4 mmol) was added to a reaction flask, to which a solution of 4 N hydrogen chloride in dioxane (13.7 ml, 54.77 mmol) was added, and the reaction was stirred at room temperature for 4 hours. A white solid was precipitated out, which was filtered to afford 798 mg of the product. The product was directly used in the next step without purification. Yield: 95%.

Step 4 Synthesis of Compound 5

Compound 4 (382 mg, 2.0 mmol), 5-chloro-3-nitropyrazolo[1,5-a]pyrimidine (396 mg, 2.0 mmol) and DIPEA (N,N-diisopropylethylamine, 1.29 g, 10 mmol) were added to a reaction flask, and 8 ml anhydrous ethanol was added. The reaction was heated to 80° C. for 1 hour. TLC was used to monitor the completion of the reaction. The reaction was concentrated to remove the solvent, and purified by silica gel column chromatography to afford 538 mg of the product. Yield: 85%. LC-MS (APCI): m/z=318.3 $(M+1)^+$.

Step 5 Synthesis of Compound 6

Compound 5 (100 mg, 0.315 mmol), ethyl 3-hydroxypropionate (55.8 mg, 0.473 mmol) and triphenylphosphine (124.1 mg, 0.473 mmol) were added to a reaction flask, to which 5 ml anhydrous tetrahydrofuran was added under nitrogen protection, and DIAD (diisopropyl azodicarboxylate, 95.6 mg, 0.473 mmol) was added dropwise at 0° C. After the addition, the reaction was warmed to room temperature and stirred for 15 hours. The reaction was concentrated to remove the solvent, and purified by silica gel column chromatography to afford 51.6 mg of the product. Yield: 38%. LC-MS (APCI): m/z=418.1 $(M+1)^+$.

Step 6 Synthesis of Compound 7

Compound 6 (192 mg, 0.46 mmol) was added to a reaction flask, which was dissolved in 8 ml methanol, and a solution of lithium hydroxide monohydrate (96.6 mg, 2.3 mmol) in 4 ml water was added. The solution was heated to 50° C. and reacted for 4-5 hours. TLC was used to monitor the completion of the reaction. The reaction was cooled to 0° C., pH thereof was adjusted to weak acidic with 1N dilute hydrochloric acid, and the reaction was extracted with ethyl acetate for 3-4 times. The organic phases were combined, dried over anhydrous sodium sulfate, filtered and concentrated to afford 174 mg of product. Yield: 97%. LC-MS (APCI): m/z=390.5 $(M+1)^+$.

Step 7 Synthesis of Compound 8

Compound 7 (174 mg, 0.45 mmol) was added to a reaction flask, which was dissolved in 5 ml methanol, and a catalytic amount of Pd/C was added. The reaction was filled with hydrogen gas, stirred and reacted at room temperature for 5-7 hours. TLC was used to monitor the completion of the reaction. After completion, the catalyst was removed by filtration, and the filtrate was concentrated to afford crude product of compound 8. The crude product was directly used in the next step without purification. LC-MS (APCI): m/z=360.4 $(M+1)^+$.

Step 8 Synthesis of Compound T-1

Compound 8 (161 mg, 0.45 mmol) was added to a reaction flask, which was dissolved in 15 ml anhydrous DMF, and FDPP (pentafluorophenyl diphenylphosphinate, 207.5 mg, 0.54 mmol) and DIPEA (290.8 mg, 2.25 mmol) were added. The reaction was stirred at room temperature overnight under nitrogen protection. TLC was used to monitor the completion of the reaction. After completion, an excess amount of water was added to the reaction, which was extracted with ethyl acetate for 3-4 times. The organic phases were combined, washed to with saturated brine, concentrated and then purified by silica gel column chromatography to afford 106 mg of the title product. Yield: 69%. LC-MS (APCI): m/z=342.5 $(M+1)^+$. $^1H$ NMR (400 MHz, DMSO-$d_6$) δ 10.11 (s, 1H), 8.56 (s, 1H), 8.12 (d, J=2.3 Hz, 1H), 7.35 (t, J=4.4 Hz, 1H), 6.98 (m, 2H), 6.52 (d, J=2.3

Hz, 1H), 4.25 (t, J=3.3 Hz, 2H), 4.01 (m, 1H), 2.66 (t, J=3.3 Hz, 2H), 1.21 (d, J=5.5 Hz, 3H).

Example 2-1: Preparation of (7S,13R)-11-fluoro-7,13-dimethyl-6,7,13,14-tetrahydro-1,15-ethenopyrazolo[4,3-f][1,4,8,10]benzoxatriazacyclotiidecin-5(6H)-one (Compound T-2-A)

T-2-A

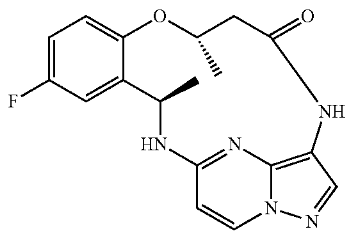

The following route was used or the synthesis:

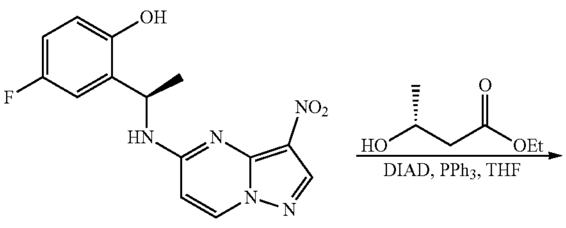

5

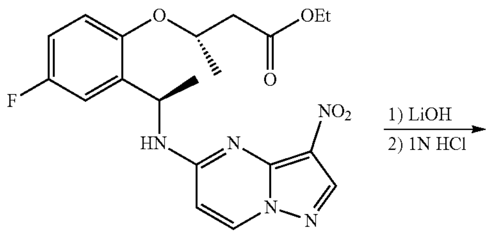

9

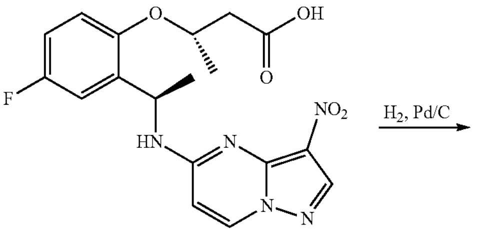

10

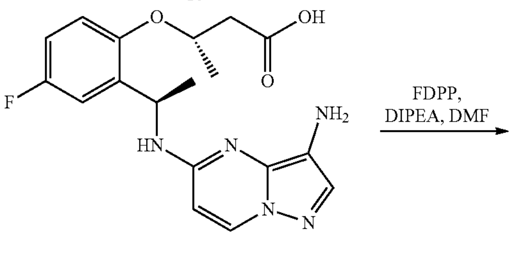

11

-continued

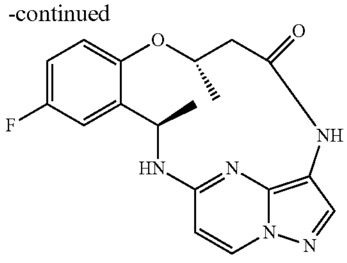

T-2-A

Step 1 Synthesis of Compound 9

Compound 5 (200 mg, 0.63 mmol), ethyl (R)-3-hydroxybutyrate (125 mg, 0.946 mmol) and triphenylphosphine (248.2 mg, 0.946 mmol) were added to a reaction flask, 10 ml anhydrous tetrahydrofuran was added under nitrogen protection, and DIAD (191.2 mg, 0.946 mmol) was added dropwise at 0° C. After the addition, the reaction was warmed to room temperature and stirred for 15 hours. The reaction was concentrated to remove the solvent, and purified by silica gel column chromatography to afford 78.8 mg of the product. Yield: 29%. LC-MS (APCI): m/z=432.1 $(M+1)^+$.

Step 2 Synthesis of Compound 10

Compound 9 (200 mg, 0.46 mmol) was added to a reaction flask, which was dissolved in 8 ml methanol, and a solution of lithium hydroxide monohydrate (96.6 mg, 2.3 mmol) in 4 ml water was added. The solution was heated to 50° C. and reacted for 4-5 hours. TLC was used to monitor the completion of the reaction. The reaction was cooled to 0° C., pH thereof was adjusted to weak acidic with 1N dilute hydrochloric acid, and the reaction was extracted with ethyl acetate for 3-4 times. The organic phases were combined, dried over anhydrous sodium sulfate, filtered and concentrated to afford 182 mg of product. Yield: 98%. LC-MS (APCI): m/z=404.5 $(M+1)^+$.

Step 3 Synthesis of Compound 11

Compound 10 (209 mg, 0.52 mmol) was added to a reaction flask, which was dissolved in 8 ml methanol, and a catalytic amount of Pd/C was added. The reaction was filled with hydrogen gas, stirred and reacted at room temperature for 5-7 hours. TLC was used to monitor the completion of the reaction. After completion, the catalyst was removed by filtration, and the filtrate was concentrated to afford crude product of compound 11. The crude product was directly used in the next step without purification. LC-MS (APCI): m/z=374.6 $(M+1)^+$.

Step 4 Synthesis of Compound T-2-A

Compound 11 (168 mg, 0.45 mmol) was added to a reaction flask, which was dissolved in 15 ml anhydrous DMF, and FDPP (207.5 mg, 0.54 mmol) and DIPEA (290.8 mg, 2.25 mmol) were added. The reaction was stirred at room temperature overnight under nitrogen protection. TLC was used to monitor the completion of the reaction. After completion, an excess amount of water was added to the reaction, which was extracted with ethyl acetate for 3-4 times. The organic phases were combined, washed with saturated brine, concentrated and then purified by silica gel column chromatography to afford 81 mg of the title product. Yield: 51%. LC-MS (APCI): m/z=356.3 $(M+1)^+$. $^1H$ NMR (400 MHz, DMSO-$d_6$) δ 10.13 (s, 1H), 8.53 (s, 1H), 8.11 (d, J=2.7 Hz, 1H), 7.35 (t, J=4.4 Hz, 1H), 6.99 (m, 2H), 6.50 (d, J=2.7 Hz, 1H), 4.06 (m, 1H), 3.99 (m, 1H), 2.66 (t, J=3.3 Hz, 2H), 1.26-1.21 (m, 6H).

Example 2-2: Preparation of (7S,13S)-11-fluoro-7,13-dimethyl-6,7,13,14-tetrahydro-1,15-ethenopyrazolo[4,3-f][1,4,8,10]benzoxatriazacyclotidecin-5(6H)-one (Compound T-2-B)

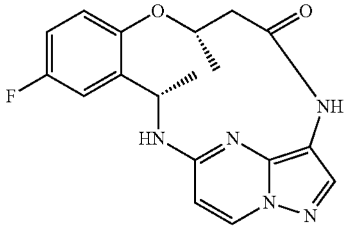

T-2-B

The following route was used for the synthesis:

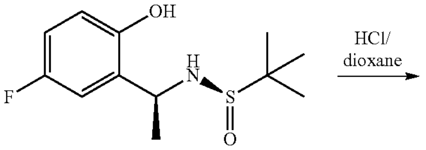

2

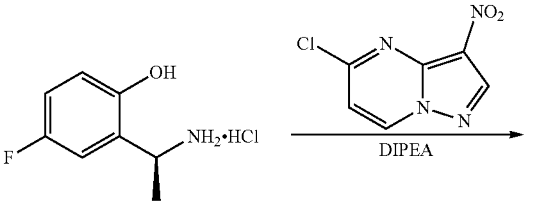

12

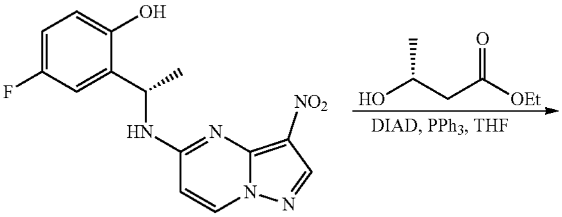

13

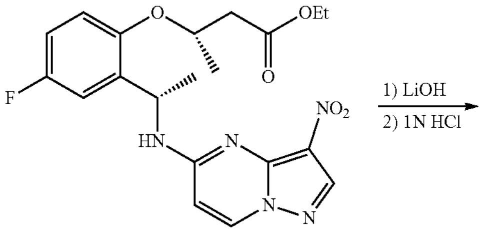

14

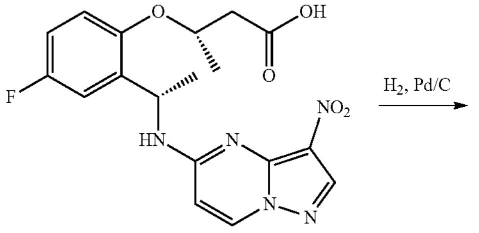

15

-continued

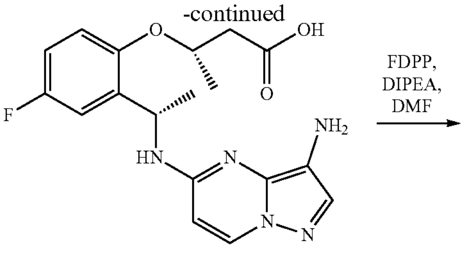

16

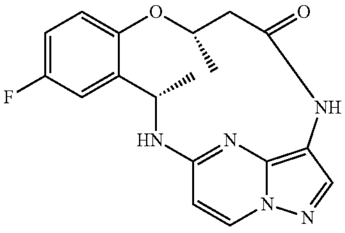

T-2-B

Step 1 Synthesis of Compound 12

Compound 2 (1.14 g, 4.4 mmol) was added in a reaction flask, to which a solution of 4 N hydrogen chloride in dioxane (13.7 ml, 54.77 mmol) was added, and the reaction was stirred at room temperature for 4 hours. A white solid was precipitated out, which was filtered to afford 798 mg of product. The product was directly used in the next step without purification. Yield: 95%.

Step 2 Synthesis of Compound 13

Compound 12 (382 mg, 2.0 mmol), 5-chloro-3-nitropyrazolo[1,5-a]pyrimidine (396 mg, 2.0 mmol) and DIPEA (N,N-diisopropylethylamine, 1.29 g, 10 mmol) were added to a reaction flask, and 8 ml absolute ethanol was added. The reaction was heated to 80° C. for 1 hour. TLC was used to monitor the completion of the reaction. The reaction was concentrated to remove the solvent, and purified by silica gel column chromatography to afford 538 mg of the product. Yield: 85%. LC-MS (APCI): m/z=318.3 $(M+1)^+$.

Step 3 Synthesis of Compound 14

Compound 13 (200 mg, 0.63 mmol), ethyl (R)-3-hydroxybutyrate (125 mg, 0.946 mmol) and triphenylphosphine (248.2 mg, 0.946 mmol) were added to a reaction flask, and 10 ml anhydrous tetrahydrofuran was added under nitrogen protection, and DIAD (191.2 mg, 0.946 mmol) was added dropwise at 0° C. After the addition, the reaction was warmed to room temperature and stirred for 15 hours. The reaction was concentrated to remove the solvent, and purified by silica gel column chromatography to afford 78.8 mg of the product. Yield: 29%. LC-MS (APCI): m/z=432.1 $(M+1)^+$.

Step 4 Synthesis of Compound 15

Compound 14 (200 mg, 0.46 mmol) was added to a reaction flask, which was dissolved in 8 ml methanol, and a solution of lithium hydroxide monohydrate (96.6 mg, 2.3 mmol) in 4 ml water was added. The solution was heated to 50° C. and reacted for 4-5 hours. TLC was used to monitor the completion of the reaction. The reaction was cooled to 0° C., pH thereof was adjusted to weak acidic with 1N dilute hydrochloric acid, and the reaction was extracted with ethyl acetate for 3-4 times. The organic phases were combined, dried over anhydrous sodium sulfate, filtered and concentrated to afford 182 mg of product. Yield: 98%. LC-MS (APCI): m/z=404.5 $(M+1)^+$.

Step 5 Synthesis of Compound 16

Compound 15 (209 mg, 0.52 mmol) was added to a reaction flask, which was dissolved in 8 ml methanol, and a catalytic amount of Pd/C was added. The reaction was filled with hydrogen gas, stirred and reacted at room temperature for 5-7 hours. TLC was used to monitor the completion of the reaction. After completion, the catalyst was removed by filtration, and the filtrate was concentrated to afford crude product of compound 16. The crude product was directly used in the next step without purification. LC-MS (APCI): m/z=374.6 $(M+1)^+$.

Step 6 Synthesis of Compound T-2-B

Compound 16 (168 mg, 0.45 mmol) was added to a reaction flask, which was dissolved in 15 ml anhydrous DMF, and FDPP (207.5 mg, 0.54 mmol) and DIPEA (290.8 mg, 2.25 mmol) were added. The reaction was stirred at room temperature overnight under nitrogen protection. TLC was used to monitor the completion of the reaction. After completion, an excess amount of water was added to the reaction, which was extracted with ethyl acetate for 3-4 times. The organic phases were combined, washed with saturated brine, concentrated and then purified by silica gel column chromatography to afford 81 mg of the title product. Yield: 51%. LC-MS (APCI): m/z=356.3 $(M+1)^+$. $^1H$ NMR (400 MHz. DMSO-4) δ 10.13 (s, 1H), 8.53 (s, 1H), 8.11 (d, J=2.7 Hz, 1H), 7.35 (t, J=4.4 Hz, 1H), 6.99 (m, 2H), 6.50 (d, J=2.7 Hz, 1H), 4.06 (m, 1H), 3.99 (m, 1H), 2.66 (t, J=3.3 Hz, 2H), 1.26-1.21 (m, 6H).

Example 3: Preparation of ((13R)-11-fluoro-6,6,13-trimethyl-6,7,13,14-tetrahydro-1,15-ethenopyrazolo [4,3-f][1,4,8,10]benzoxatriazacyclotridecin-5(6H)-one (Compound T-3)

T-3

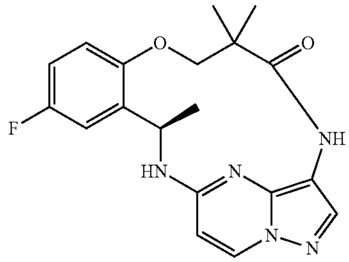

The following route was used for the synthesis:

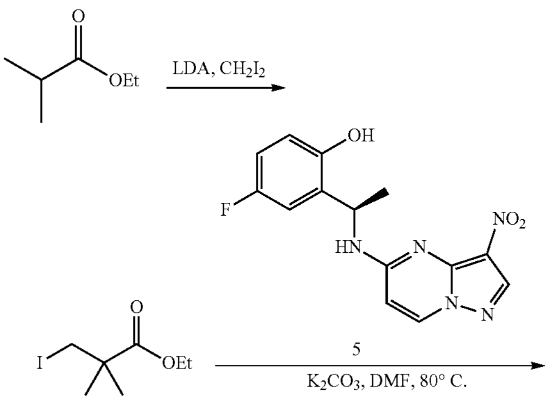

5

17

-continued

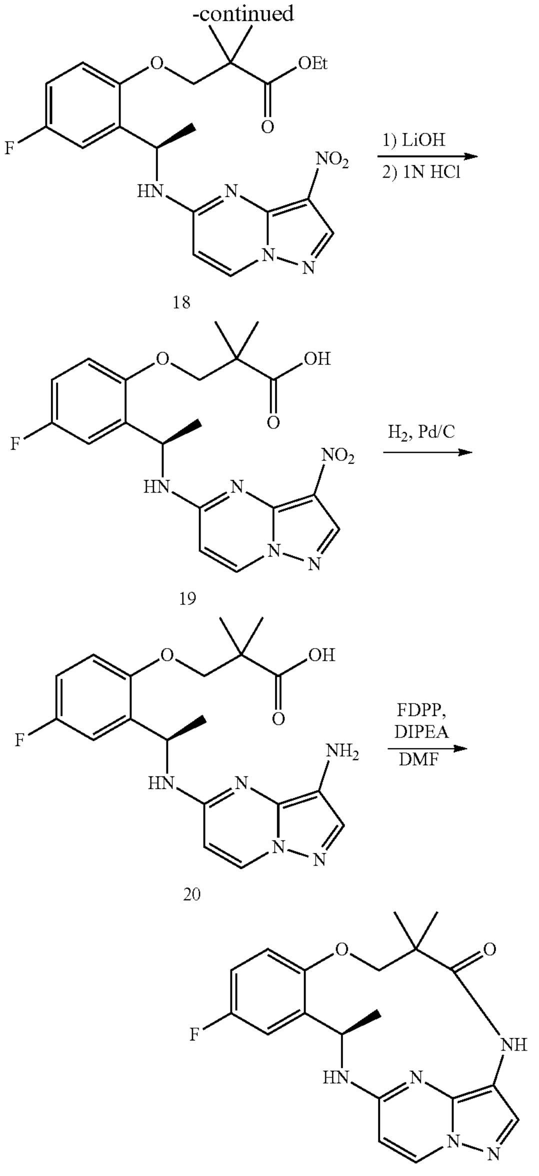

18

19

20

T-3

Step 1 Synthesis of Compound 17

Ethyl isobutyrate (2.5 g, 21.5 mmol) was added to a reaction flask, and 40 ml anhydrous tetrahydrofuran was added under nitrogen protection. The mixture was cooled to −40° C., and LDA (lithium diisopropylamide, 11.8 ml, 23.6 mmol) was slowly added dropwise. After the addition, the reaction was gradually warmed to room temperature and stirred to react for half an hour. After cooled to −40° C., a solution of diiodomethane (5.76 g, 21.5 mmol) in 10 ml anhydrous tetrahydrofuran was slowly added. After the addition, the temperature of the reaction was warmed to room temperature and the reaction was reacted overnight. Water was added to quench the reaction, the organic phase was separated, and the aqueous phase was extracted with ethyl acetate for 3-4 times. The organic phases were combined, washed with saturated brine, dried over anhydrous sodium sulfate, filtered and concentrated to afford 4.62 g of the product. Yield: 84%.

Step 2 Synthesis of Compound 18

Compound 5 (300 mg, 0.95 mmol), compound 17 (291 mg, 1.14 mmol) and potassium carbonate (525.2 mg, 3.8 mmol) were added into a reaction flask, and DMF was added. The reaction was heated to 80° C. and stirred to react overnight. TLC was used to monitor the completion of the reaction. After completion, the reaction was cooled to room temperature, added with an excess amount of water, and extracted with ethyl acetate for 3-4 times. The organic phases were combined, washed with saturated brine, concentrated and then purified by silica gel column chromatography to afford 321.3 mg of the title product. Yield: 76%, LC-MS (APCI): m/z=446.1 $(M+1)^+$.

Step 3 Synthesis of Compound 19

Compound 18 (321 mg, 0.72 mmol) was added to a reaction flask, which was dissolved in 10 ml methanol, a solution of lithium hydroxide monohydrate (151.5 mg, 3.5 mmol) in 3 ml water was added, and the reaction was heated to 50° C. and reacted for 4-5 hours. TLC was used to monitor the completion of the reaction. The reaction was cooled to 0° C., pH thereof was adjusted to weak acidic with 1N dilute hydrochloric acid, and the reaction was extracted with ethyl acetate for 3-4 times. The organic phases were combined, dried over anhydrous sodium sulfate, filtered and concentrated to afford 279 mg of the product. Yield: 93%. LC-MS (APCI): m/z=418.3 $(M+1)^+$.

Step 4 Synthesis of Compound 20

Compound 19 (279 mg, 0.67 mmol) was added to a reaction flask, which was dissolved in 10 ml methanol, and a catalytic amount of Pd/C was added. The reaction was filled with hydrogen gas, stirred and reacted at room temperature for 5-7 hours. TLC was used to monitor the completion of the reaction. After completion, the catalyst was removed by filtration, and the filtrate was concentrated to afford crude product of compound 20, which was directly used in the next reaction without purification. LC-MS (APCI): m/z=387.9 $(M+1)^+$.

Step 5 Synthesis of Compound T-3

Compound 20 (259 mg, 0.67 mmol) was added to a reaction flask, which was dissolved in 20 ml anhydrous DMF, and FDPP (309 mg, 0.80 mmol) and DIPEA (433 mg, 3.35 mmol) were added. The reaction was stirred to react at room temperature overnight under nitrogen protection. TLC was used to monitor the completion of the reaction. After completion, the reaction was diluted with an excess amount of water, and extracted with ethyl acetate for 3-4 times. The organic phases were combined, washed with saturated brine, concentrated and then purified by silica gel column chromatography to afford 136 mg of the title product. Yield: 55%. LC-MS (APCI): m/z=370.3 $(M+1)^+$. $^1H$ NMR (400 MHz. DMSO-$d_6$) δ 10.15 (s, 1H), 8.56 (s, 1H), 8.12 (d, J=2.3 Hz, 1H), 7.37 (t, J=4.4 Hz, 1H), 6.99 (m, 2H), 6.52 (d, J=2.3 Hz, 1H), 4.23 (s, 2H), 4.00 (m, 1H), 1.21 (d, J=5.5 Hz, 3H).

Example 4: Preparation of (14R)-12-fluoro-14-methyl-5,6,7,8,14,15-hexahydro-1,16-ethenopyrazolo[4,3-g][1,4,9,11]benzoxatetraazacyclotetradecin-5(6H)-one (Compound T-4)

T-4

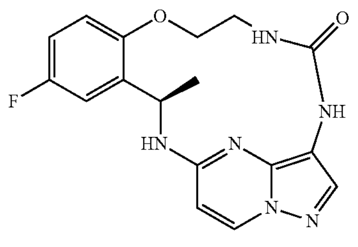

The following route was used or the synthesis:

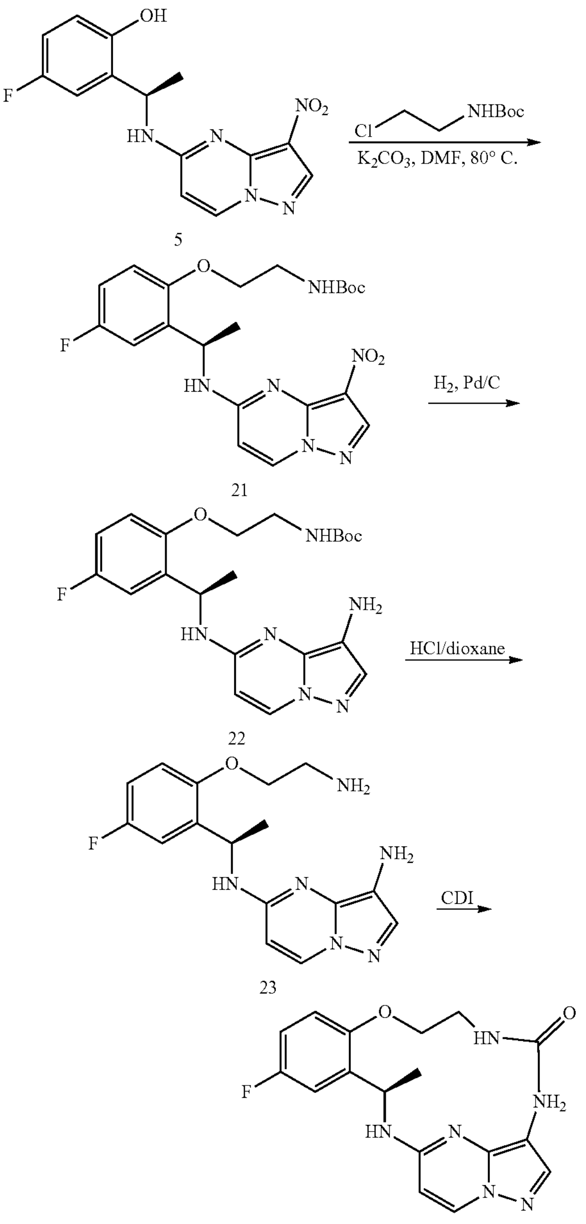

T-4

Step 1 Synthesis of Compound 21

Compound 5 (300 mg, 0.95 mmol), N-tert-butoxycarbonyl-2-chloroethylamine (203.3 mg, 1.13 mmol) and potassium carbonate (525.2 mg, 3.8 mmol) were added to a reaction flask, and dissolved in 20 ml anhydrous DMF. The reaction was heated to 80° C. and reacted overnight. TLC was used to monitor the completion of the reaction. After completion, the reaction was diluted with an excess amount of water, and extracted with ethyl acetate for 3-4 times. The organic phases were combined, washed with saturated brine, concentrated and then purified by silica gel column chromatography to afford 345 mg of the product. Yield: 79%. LC-MS (APCI): m/z=461.2 $(M+1)^+$.

Step 2 Synthesis of Compound 22

Compound 21 (346 mg, 0.75 mmol) was added to a reaction flask, which was dissolved in 12 ml anhydrous methanol, and a catalytic amount of Pd/C was added. The reaction was filled with hydrogen gas, and reacted at room temperature for 1-2 hours. TLC was used to monitor the completion of the reaction. The reaction was filtered after completion, the filtrate was concentrated to afford 346 mg of the product, which was directly used in the next reaction without purification. LC-MS (APCI): m/z=431.3 $(M+1)^+$.

Step 3 Synthesis of Compound 23

Compound 22 (346 mg, 0.75 mmol) was added to a reaction flask, and 4M hydrogen chloride in dioxane (10 ml, 40 mmol) was added. The reaction was stirred at room temperature for 2-3 hours. After monitoring the completion of the reaction with MS, the reaction was concentrated to remove the solvent, which is then directly used in the next reaction. LC-MS (APCI): m/z=331.6 $(M+1)^+$.

Step 4 Synthesis of Compound T4

Compound 23 (200 mg, 0.61 mmol) was added to a reaction flask, to which 15 ml of dichloromethane solvent was added, and CDI (N,N'-carbonyldiimidazole, 196 mg, 1.21 mmol) was then added. The reaction was stirred at room temperature for 6 hours. TLC was used to monitor the completion of the reaction. The reaction was concentrated to remove the solvent, and purified by silica gel column chromatography to afford 134 mg of the product. Yield: 62%. LC-MS (APCI): m/z=357.5 $(M+1)^+$. $^1H$ NMR (400 MHz, DMSO-$d_6$) δ 10.11 (s, 1H), 9.85 (s, 1H), 8.56 (s, 1H), 8.12 (d, J=2.3 Hz, 1H), 7.35 (t, J=4.4 Hz 1H), 6.98 (m, 2H), 6.51 (d, J=2.3 Hz, 1H), 4.35 (t, J=3.5 Hz, 2H), 4.01 (m, 1H), 3.85 (t, J=3.5 Hz, 2H), 1.24 (d, J=5.5 Hz, 3H).

Example 5: Preparation of (14R)-12-fluoro-14-methyl-5,6,7,8,14,15-hexahydro-1,16-ethenopyrazolo[4,3-g][1,4,9,11]benzodioadiazatridecin-5(6H)-one (Compound T-5)

T-5

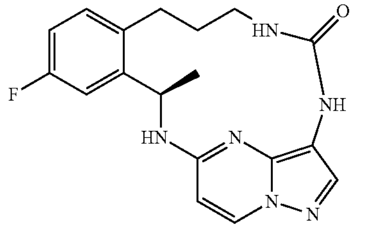

The following route was used for the synthesis:

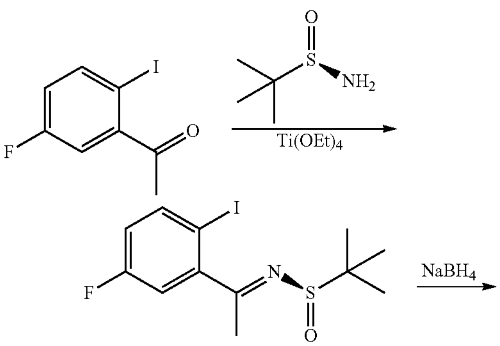

24

-continued

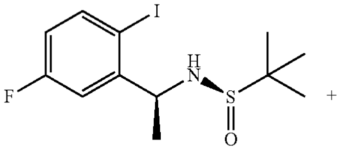

25

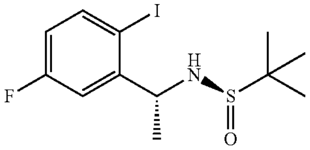

26

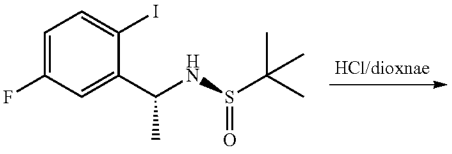

26

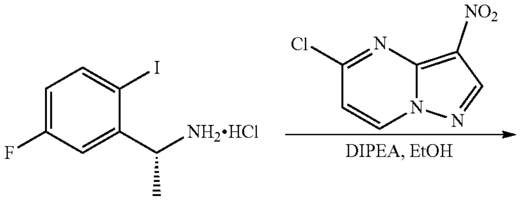

27

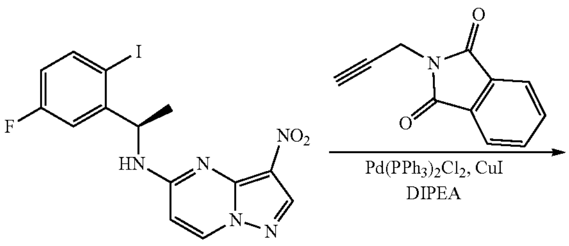

28

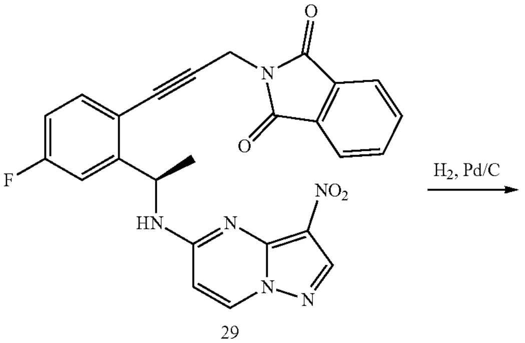

29

-continued

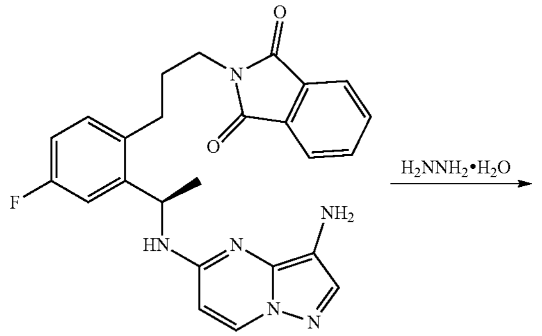

30

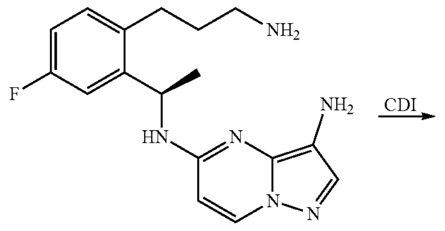

31

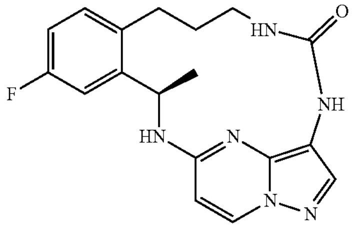

T-5

Step 1 Synthesis of Compound 24

5-fluoro-2-iodoacetophenone (3.5 g, 13.26 mmol), (R)-tert-butylsulfinamide (2.41 g, 19.88 mmol) and tetraethyl titanate (7.54 g, 26.52 mmol) were added to a reaction flask, 50 ml anhydrous tetrahydrofuran was added, and the reaction was heated to reflux and stirred for 12 hours under nitrogen protection. TLC was used to monitor the completion of the reaction. The reaction was diluted with water and extracted 3-4 times with ethyl acetate. The organic phases were combined, washed with saturated brine, concentrated and then purified by silica gel column chromatography to afford 3.94 g of the product. Yield: 81%. LC-MS (APCI): m/z=368.4 $(M+1)^+$.

Step 2 Synthesis of Compound 26

Compound 24 (3.5 g, 9.54 mmol) was added to a reaction flask, which was dissolved in 25 ml tetrahydrofuran and 0.5 ml water, and sodium borohydride (0.54 g, 14.3 mmol) was added in batches at 0° C. After the addition, the reaction was warmed to room temperature and stirred to react for 12 hours. TLC was used to monitor the completion of the reaction. After completion, the reaction was diluted with water and extracted 3-4 times with ethyl acetate. The organic phases were combined, washed with saturated brine, concentrated and then purified by silica gel column chromatography to afford 3.27 g of the product. Yield: 93%. LC-MS (APCI): m/z=370.6 $(M+1)^+$.

Step 3 Synthesis of Compound 27

Compound 26 (3.27 g, 8.87 mmol) was added to a reaction flask, to which 4 M hydrogen chloride in dioxane (20 ml, 80 mmol) was then added, and the reaction was stirred at room temperature for 4-5 hours. A white solid was precipitated out, the resultant product was filtered and directly used in the next reaction after it was dried in vacuum. LC-MS (APCI): m/z=266.4 $(M+1)^+$.

Step 4 Synthesis of Compound 28

Compound 27 (300 mg, 1.13 mmol), 5-chloro-3-nitropyrazolo[1,5-a]pyrimidine (224 mg, 1.13 mmol) were added to a reaction flask, which was dissolved by adding 10 ml ethanol, and DIPEA (584 mg, 4.52 mmol) was added. The reaction was heated to 80° C. and stirred for 1 hour. TLC was used to monitor the completion of the reaction. The reaction was cooled to room temperature, concentrated and then purified by silica gel column chromatography to afford 371 mg of the product. Yield: 77%. LC-MS (APCI): m/z=428.1 $(M+1)^+$.

Step 5 Synthesis of Compound 29

Compound 28 (371 mg, 0.87 mmol), 3-phthalimido-1-propyne (241 mg, 1.3 mmol), bis(triphenylphosphine)palladium dichloride (30.5 mg, 0.043 mmol) and copper iodide (16.4 mg, 0.086 mmol) were added to a reaction flask, which was dissolved in 10 ml anhydrous tetrahydrofuran, and DIPEA (337.3 mg, 2.61 mmol) was added. The reaction was stirred and reacted overnight at room temperature under nitrogen protection. TLC was used to monitor the completion of the reaction. The reaction solution was concentrated and purified by silica gel column chromatography to afford 274 mg of the product. Yield: 65%. LC-MS (APCI): m/z=485.5 $(M+1)^+$.

Step 6 Synthesis of Compound 30

Compound 29 (274 mg, 0.57 mmol) was added to a reaction flask, which was dissolved in 5 ml methanol, and a catalytic amount of Pd/C was then added. The reaction was filled with hydrogen gas, stirred and reacted at room temperature overnight. TLC was used to monitor the completion of the reaction, and the reaction solution was filtered to afford 258 mg of the crude product, which was directly used in the next reaction. LC-MS (APCI): m/z=459.4 $(M+1)^+$.

Step 7 Synthesis of Compound 31

Compound 30 (258 mg, 0.56 mmol) was added to a reaction flask, which was dissolved in 10 ml methanol, then an excess amount of hydrazine hydrate was added. The reaction was heated to reflux and reacted for 4-6 hours. TLC was used to monitor the completion of the reaction. The reaction was concentrated to remove the solvent, and diluted with water, extracted with chloroform/isopropanol (3:1) for 4-5 times. The organic phases 0.5 were combined, washed with saturated brine, concentrated, and then purified by column chromatography to afford 71.6 mg of the product. Yield: 39%, LC-MS (APCI): m/z=329.6 $(M+1)^+$.

Step 8 Synthesis of Compound T-5

Compound 31 (71 mg, 0.22 mmol) was added to a reaction flask, and 10 ml dichloromethane solvent was added, then CDI (54 mg, 0.33 mmol) was added. The reaction was stirred and reacted for 6 hours at room temperature. TLC was used to monitor the completion of the reaction. The reaction was concentrated to remove the solvent, and purified by silica gel column chromatography to afford 51 mg of the product. Yield: 66%. LC-MS (APCI): m/z=355.1 $(M+1)^+$. $^1H$ NMR (400 MHz, DMSO-$d_6$) δ 10.11 (s, 1H), 8.56 (s, 1H), 8.12 (d, J=2.3 Hz, 1H), 7.35 (t, J=4.4 Hz, 1H), 6.98 (m, 2H), 6.52 (d, J=2.3 Hz, 1H), 4.01 (m, 1H), 2.66 (t, J=3.8 Hz, 2H), 2.45 (t, J=5.2 Hz, 2H), 1.75 (m, 2H), 1.21 (d, J=5.5 Hz, 3H).

Example 6: Preparation of (13R)-11-fluoro-13-methyl-6,7,13,14-tetrahydr-1,15-ethenopyrazolo[4,3-f][1,4,8,10]benzodioadiazatridecin-5(6H)-one (Compound T-6)

T-6

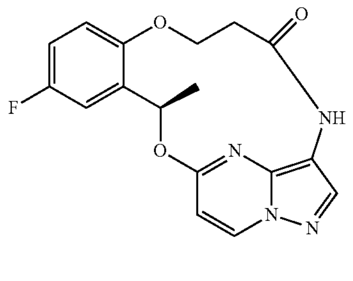

The following route was used for the synthesis:

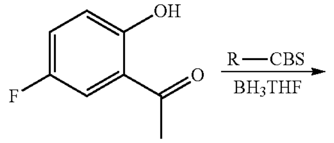

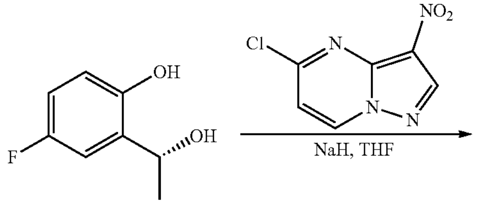

32

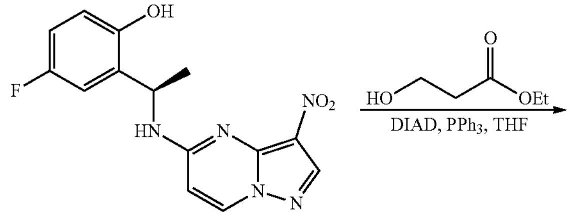

33

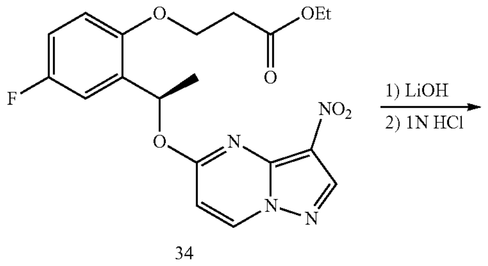

34

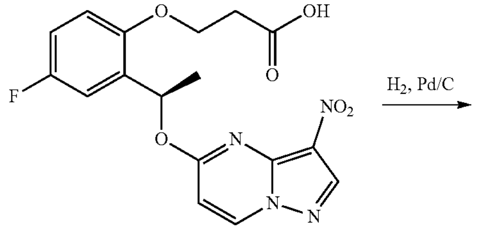

35

-continued

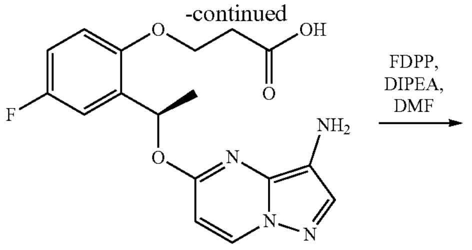

36

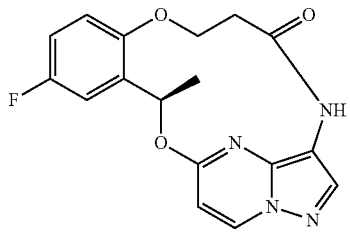

T-6

Step 1 Synthesis of Compound 32

5-fluoro-2-hydroxyacetophenone (4.5 g, 29.2 mmol) was added to a reaction flask, which was dissolved in 40 ml anhydrous THF, and R—CBS (1.46 ml, 1.46 mmol) was added dropwise at 0° C. under nitrogen protection. After the addition, the reaction was stirred for 20 minutes, borane in tetrahydrofuran (29.2 ml, 29.2 mmol) was then slowly added dropwise. After the addition, the reaction was stirred and reacted for half an hour at low temperature. TLC was used to monitor the completion of the reaction. After completion, a small amount of methanol was added to quench the reaction. The reaction was concentrated to remove the solvent, ethyl acetate and water were added, the organic phase was separated, and aqueous phase was extracted with ethyl acetate for 3-4 times. The organic phases were combined, washed with saturated brine, concentrated and purified by column chromatography to afford 4.33 g of the product. Yield: 95%.

Step 2 Synthesis of Compound 33

Compound 32 (1.0 g, 6.41 mmol), 5-chloro-3-nitropyrazolo[1,5-α]pyrimidine (1.27 g, 6.41 mmol) were added to a reaction flask, which was dissolved in 20 ml ethanol, and NaH (2.48 g, 19.23 mmol) was added. The reaction was heated to 80° C., stirred and reacted for 1 hour. TLC was used to monitor the completion of the reaction. The reaction was cooled to room temperature, concentrated and purified by column chromatography to afford 1.79 g of the product. Yield: 88%. LC-MS (APCI): m/z=319.2 $(M+1)^+$.

Step 3 Synthesis of Compound 34

Compound 33 (1.2 g, 3.77 mmol), ethyl 3-hydroxypropionate (0.67 g, 5.66 mmol) and triphenylphosphine (1.48 g, 5.66 mmol) were added to a reaction flask, to which 5 ml anhydrous tetrahydrofuran was added under nitrogen protection, and DIAD (1.14 g, 5.66 mmol) was added dropwise under 0° C. After the addition, the reaction was warmed to room temperature and stirred for 15 hours. The reaction was concentrated to remove the solvent, and purified by silica gel column chromatography to afford 488.5 mg of the product. Yield: 31%. LC-MS (APCI): m/z=419.7 (M+1).

Step 4 Synthesis of Compound 35

Compound 34 (488 mg, 1.17 mmol) was added to a reaction flask, which was dissolved in 10 ml methanol, and a solution of lithium hydroxide monohydrate (245 mg, 5.84 mmol) in 4 ml water was added. The reaction was heated to 50° C. and reacted for 4-5 hours. TLC was used to monitor the completion of the reaction. The reaction was cooled to 0° C., pH thereof was adjusted to weak acidic with 1N dilute hydrochloric acid, and the reaction was extracted with ethyl acetate for 3-4 times. The organic phases were combined, dried over anhydrous sodium sulfate, filtered and concentrated to afford 433.4 mg of the product. Yield: 95%. LC-MS (APCI): m/z=391.5 $(M+1)^+$.

Step 5 Synthesis of Compound 36

Compound 35 (433 mg, 1.11 mmol) was added to a reaction flask, which was dissolved in 10 ml methanol, and a catalytic amount of Pd/C was added. The reaction was filled with hydrogen gas, stirred and reacted at room temperature for 5-7 hours. TLC was used to monitor the completion of the reaction. After completion, the catalyst was removed by filtration, and the filtrate was concentrated to afford crude product of compound 36, which was directly used in the next reaction without purification. LC-MS (APCI): m/z=361.4 $(M+1)^+$.

Step 6 Synthesis of Compound T-6

Compound 36 (399 mg, 1.11 mmol) was added to a reaction flask, which was dissolved in 25 ml anhydrous DMF, and FDPP (511.8 mg, 1.33 mmol) and DIPEA (717.3 mg, 5.55 mmol) were added. The reaction was stirred at room temperature overnight under nitrogen protection. TLC was used to monitor the completion of the reaction. After completion, the reaction was diluted with an excess amount of water, and extracted with ethyl acetate for 3-4 times. The organic phases were combined, washed with saturated brine, concentrated and then purified by silica gel column chromatography to afford 221 mg of the title product. Yield: 58%. LC-MS (APCI): m/z=343.5 $(M+1)^+$. LC-MS (APCI): m/z=342.5 $(M+1)^+$. $^1$H NMR (400 MHz. DMSO-$d_6$) δ 10.13 (s, 1H), 8.59 (s, 1H), 8.10 (d, J=2.3 Hz, 1H), 7.35 (t, J=4.4 Hz, 1H), 6.98 (m, 2H), 6.52 (d, J=2.3 Hz, 1H), 4.25 (t, J=3.3 Hz, 2H), 4.12 (m, 1H), 2.68 (t, J=3.3 Hz, 2H), 1.23 (d, J=5.5 Hz, 3H).

Example 7: Preparation of 9-fluoro-13-oxa-2,17,20,21,24-pentaazapentacyclo[16.5.2.$0^{2,6}$.$0^{7,12}$.$0^{21,25}$]pentacosane-1(24),7,9,11,18(25),19,22-heptaene-16-one (Compound 9a), (6R)-9-fluoro-13-oxa-2,7,20,21,24-pentaazapentacyclo[16.5.2.$0^{26}$.$0^{7,12}$.$0^{21,25}$]pentacosane-1(24),7,9,11,18(25),19,22-heptaene-16-one (Compound L-1-A), and (6S)-9-fluoro-13-oxa-2,17,20,21,24-pentaazapentacyclo[16.5.2.$0^{2,6}$.$0^{7,12}$.$0^{21,25}$]pentacosane-1(24),7,9,11,18(25),19,22-heptaene-16-one (Compound L1-1-B)

9a

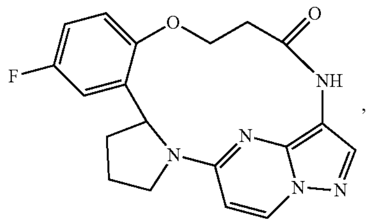

,

-continued

L-1-A

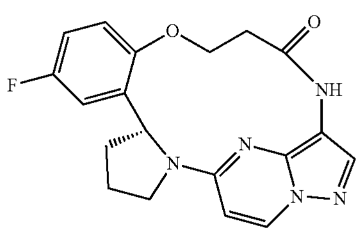

and

L-1-B

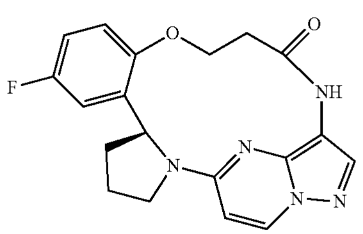

The following route was used for the synthesis:

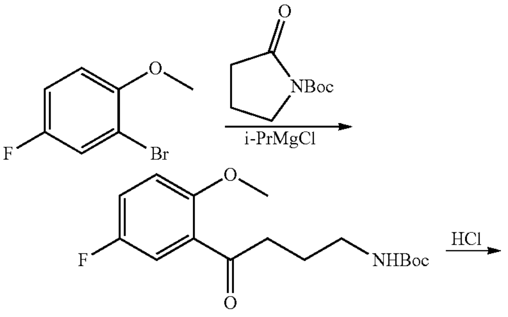

1a

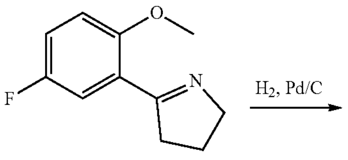

2a

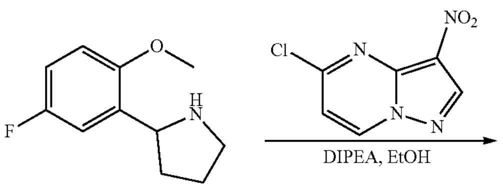

3a

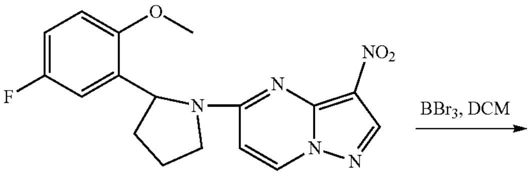

4a

-continued

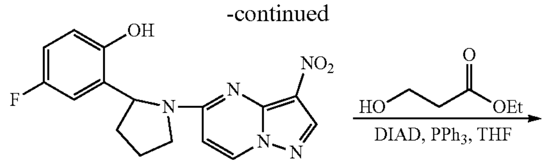

5a

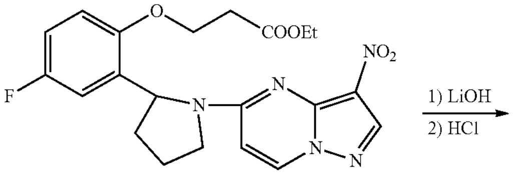

6a

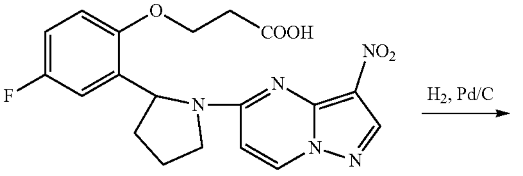

7a

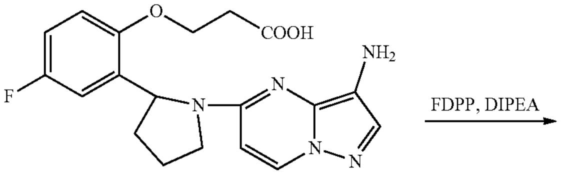

8a

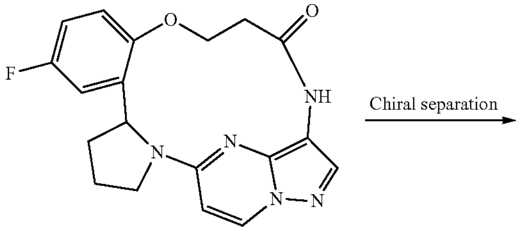

9a

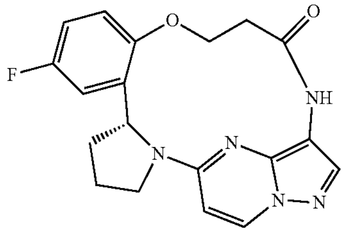

+

L-1-A

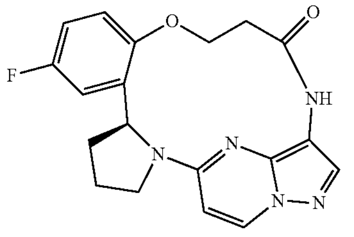

L-1-B

Step 1 Synthesis of Compound 1a 2-bromo-4-fluoro-1-methoxybenzene (18.95 g, 93 mmol) was dissolved in anhydrous THF (100 mL), and isopropyl magnesium chloride solution (43.4 mL, 86.8 mmol) was slowly added dropwise at −40° C. After the addition, the mixture was naturally warmed to 0° C. and stirred for 1 h, and a solution of N-tert-butoxycarbonyl-2-pyrrolidone (11.46 g, 62.0 mmol) in anhydrous tetrahydrofuran (30 mL) was then slowly added dropwise at −40° C. After the addition, the mixture was stirred at room temperature for 30 min. The reaction solution was poured into 100 mL of saturated ammonium chloride solution and stirred for 10 min, then the reaction solution was separated by standing. The aqueous phase was extracted three times with 40 mL ethyl acetate. The organic phases were combined and washed with saturated brine, and dried over anhydrous sodium sulfate. The residue was filtered and concentrated, purified by column chromatography to afford 17.68 g of compound 1a as light yellow liquid. Yield: 61.1%. LC-MS (APCI): m/z=312.1 $(M+1)^+$.

Step 2 Synthesis of Compound 2a

Compound 1a (1.2 g, 3.85 mmol) was dissolved in toluene (10 mL), to which 0.7 mL concentrated hydrochloric acid was added. The reaction was heated to 65° C., stirred and reacted overnight. The reaction was cooled to room temperature, pH thereof was adjusted to 14 with 2 M sodium hydroxide, and stirred for 1 h. TLC was used to monitor the completion of the reaction. The organic phase was separated, and the aqueous phase was extracted 3 times with ethyl acetate. The organic phases were combined, washed with saturated brine, concentrated, and purified by column chromatography to afford 557 mg of compound 2a as yellow liquid. Yield: 75%. LC-MS (APCI): m/z=194.3 $(M+1)^+$.

Step 3 Synthesis of Compound 3a

Compound 2a (557 mg, 2.89 mmol) was dissolved in anhydrous methanol (10 mL), Pd/C (50 mg) was added, and the reaction was hydrogenated at room temperature overnight. The reaction was filtered, the filter residue was washed with 20 mL ethyl acetate, and the filtrate was concentrated to afford 556 mg of compound 3a as colorless oily liquid which was directly used in the next step. Yield: 98.5%. LC-MS (APCI): m/z=196.3 $(M+1)^+$.

Step 4 Synthesis of Compound 4a

Compound 3a (722 mg, 3.7 mmol) and 5-chloro-3-nitro-pyrazolo[1,5-a]pyrimidine (733 mg, 3.7 mmol) were dissolved in anhydrous ethanol (10 mL), DIPEA (N,N-diisopropylethylamine, 1.91 g, 14.8 mmol) was added at room temperature, and heated to reflux for 30 min. The reaction solution was concentrated, purified by column chromatography (PE/EA, 30%-50%) to afford 1.15 g of compound 4a as light yellow solid powder. Yield: 81%. LC-MS (APCI): m/z=385.5 $(M+1)^+$.

Step 5 Synthesis of Compound 5a

Compound 4a (1.57 g, 4.1 mmol) was dissolved in 10 ml anhydrous dichloromethane, 1 M boron tribromide solution (20.5 ml, 20.5 mmol) was added dropwise at 0° C. After the addition, the reaction was warmed to room temperature and reacted for 1-2 hours. TLC was used to monitor the completion of the reaction. After completion, a small amount of water was added dropwise to quench the reaction under ice bath, the organic phase was separated, and the aqueous phase was extracted with dichloromethane for 3-4 times. The organic phases were combined, washed with saturated brine, concentrated and then purified by silica gel column chromatography to afford 880 mg of the title product. Yield: 58%. LC-MS (APCI): m/z=371.6 $(M+1)^+$.

Step 6 Synthesis of Compound 6a

Compound 5a (116 mg, 0.315 mmol), ethyl 3-hydroxy-propionate (55.8 mg, 0.473 mmol) and triphenylphosphine (124.1 mg, 0.473 mmol) were added to a reaction flask, to which 5 ml anhydrous tetrahydrofuran was added under nitrogen protection, and DIAD (diisopropyl azodicarboxylate, 95.6 mg, 0.473 mmol) was added dropwise at 0° C. After the addition, the reaction was warmed to room temperature and stirred to react for 15 hours. The reaction was concentrated to remove the solvent, and purified by silica gel column chromatography to afford 53 mg of the product. Yield: 38%. LC-MS (APCI): m/z=444.1 $(M+1)^+$.

Step 7 Synthesis of Compound 7a

Compound 6a (204 mg, 0.46 mmol) was added to a reaction flask, which was dissolved in 8 ml methanol, and a solution of lithium hydroxide monohydrate (96.6 mg, 2.3 mmol) in 4 ml water was added. The reaction was heated to 50° C. and reacted for 4-5 hours. TLC was used to monitor the completion of the reaction. The reaction was cooled to 0° C., pH thereof was adjusted to weak acidic with 1N dilute hydrochloric acid, and the reaction was extracted with ethyl acetate for 3-4 times. The organic phases were combined, dried over anhydrous sodium sulfate, filtered and concentrated to afford 181 mg of the product. Yield: 95%. LC-MS (APCI): m/z=416.5 $(M+1)^+$.

Step 8 Synthesis of Compound 8a

Compound 7a (186 mg, 0.45 mmol) was added to a reaction flask, which was dissolved in 5 ml methanol and a catalytic amount of Pd/C was added. The reaction was filled with hydrogen gas, stirred and reacted at room temperature for 5-7 hours. TLC was used to monitor the completion of the reaction. After completion, the catalyst was removed by filtration, and the filtrate was concentrated to afford crude product of compound 8a, which was directly used in the next reaction without purification. LC-MS (APCI): m/z=386.4 $(M+1)^+$.

Step 9 Synthesis of Compound 9a

The product obtained in the previous step was dissolved in 20 ml of anhydrous DMF, FDPP (pentafluorophenyl diphenylphosphinate, 240 mg, 0.62 mmol) and DIPEA (336 mg, 2.6 mmol) were added at room temperature, and the reaction was stirred and reacted overnight under nitrogen protection. TLC was used to monitor the completion of the reaction. After completion, the reaction was diluted by water, and extracted with ethyl acetate for 3-4 times. The organic phases were combined, washed with saturated brine, concentrated and then purified by silica gel column chromatography to afford 71 mg of compound 9a as off-white solid. Yield: 43%. LC-MS (APCI): m/z=368.3 $(M+1)^+$. $^1H$ NMR (400 MHz, DMSO-$d_6$) δ 10.11 (s, 1H), 8.87 (s, 1H), 8.04 (d, J=2.3 Hz, 1H), 7.52 (s, 1H), 7.44 (d, J=3.3 Hz, 1H), 7.28 (d, J=3.3 Hz, 1H), 6.74 (d, J=2.3 Hz, 1H), 4.38 (t, J=4.4 Hz, 2H), 4.12 (m 1H), 3.61 (dd, J=17.0, 9.3 Hz, 2H), 2.36 (t, J=4.4 Hz, 2H), 2.01-1.65 (m, 2H), 1.22 (d, J=4.5 Hz, 2H).

Step 10 Synthesis of Compounds L-1-A and L-1-B

Preparative chiral column: CHIRALPAK IC (brand name), 4.6 mm×250 mm (internal diameter×length), 5 μm (particle size of the filler)

Column temperature: 30° C.

Flow rate: 1.0 mL/min

UV detection wavelength: 254 nm

Mobile phase: methyl tert-butyl ether:methanol=70:30

Under the above preparative chiral column and chiral resolution conditions, racemic compound 9a was separated to afford target compound L-1-A (retention time: 20.33 min, relative amount: 43.4%) and L-1-B (retention time: 6.31 min, relative amount: 44.0%).

Example 8: Preparation of (14S)-9-fluoro-4-methyl-3-oxa-2,17,20,21,24-pentaazapentacyclo[16.5.2.$0^{2,6}$.$0^{7,12}$.$0^{21,25}$]pentacosane-1(24),7,9,11,18(25),19,22-heptaene-16-one (Compound 13a), (6R,14S)-9-fluoro-14-methyl-13-oxa-2,17,20,21,24-pentaazapentacyclo[16.5.2.$0^{2,6}$.$0^{7,12}$.$0^{21,25}$]pentacosane-1(24),7,9,11,18(25),19,22-heptaene-16-one (Compound L-2-A), and (6S,14S)-9-fluoro-14-methyl-13-oxa-2,17,20,21,24-pentaazapentacyclo[16.5.2.$0^{2,6}$.$0^{7,12}$.$0^{21,25}$]pentacosane-1(24),7,9,11,18(25),19,22-heptaene-16-one (Compound L-2-B)

13a

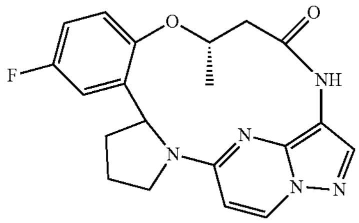

,

L-2-A

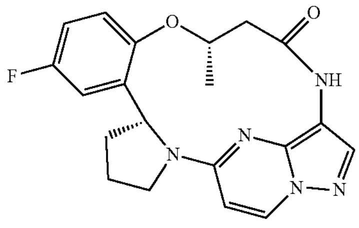

and

L-2-B

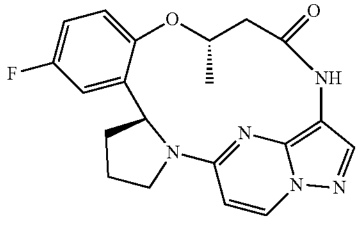

The following route was used for the synthesis:

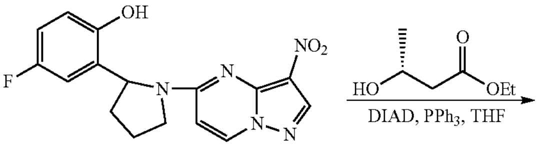

5a

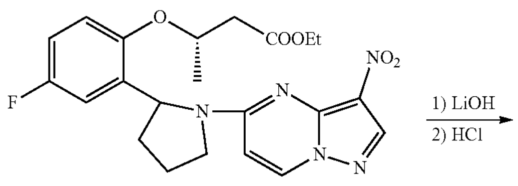

10a

-continued

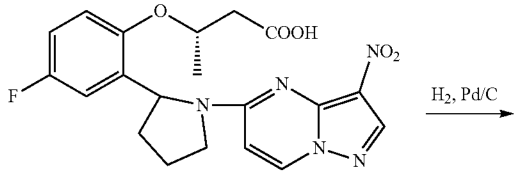

11a

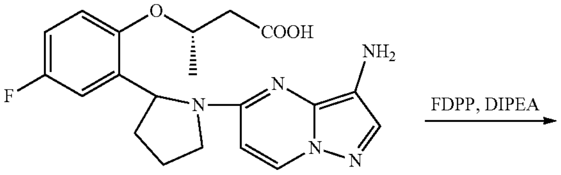

12a

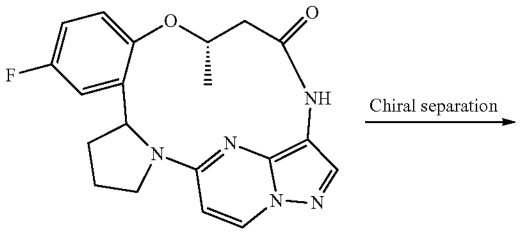

13a

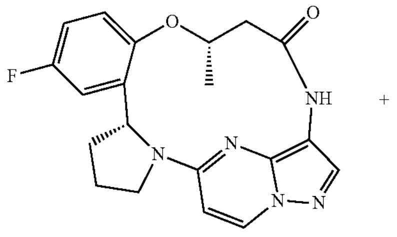

+

L-2-A

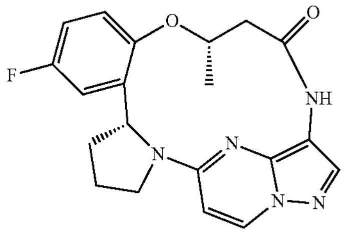

L-2-B

Step Synthesis of Compound 10a

Compound 5a (216 mg, 0.63 mmol), ethyl (R)-3-hydroxybutyrate (125 mg, 0.946 mmol) and triphenylphosphine (248.2 mg, 0.946 mmol) was added to a reaction flask, to which 10 ml anhydrous tetrahydrofuran was added under nitrogen protection, and DIAD (191.2 mg 0.946 mmol) was added dropwise at 0° C. After the addition, the reaction was warmed to room temperature and stirred for 15 hours. The reaction was concentrated to remove the solvent, purified by silica gel column chromatography to afford 77.7 mg of the product. Yield 27%. LC-MS (APCI): m/z=458.1 $(M+1)^+$.

Step 2 Synthesis of Compound 11a

Compound 10a (210 mg, 0.46 mmol) was added to a reaction flask, which was dissolved in 8 ml methanol, and a solution of lithium hydroxide monohydrate (96.6 mg, 2.3 mmol) in 4 ml water was added. The reaction was heated to 50° C. and reacted for 4-5 hours. TLC was used to monitor the completion of the reaction. The reaction was cooled to 0° C., pH thereof was adjusted to weak acidic with 1N dilute hydrochloric acid, and the reaction was extracted with ethyl acetate for 3-4 times. The organic phases were combined, dried over anhydrous sodium sulfate, filtered and concentrated to afford 193 mg of the product. Yield: 98%. LC-MS (APCI): m/z=430.5 $(M+1)^+$.

Step 3 Synthesis of Compound 12a

Compound 1a (223 mg, 0.52 mmol) was added to a reaction flask, which was dissolved in 8 ml methanol and a catalytic amount of Pd/C was added. The reaction was filled with hydrogen gas, stirred and reacted at room temperature for 5-7 hours, TLC was used to monitor the completion of the reaction. After completion, the catalyst was removed by filtration, and the filtrate was concentrated to afford crude product of compound 12a, which was directly used in the next reaction without purification. LC-MS (APCI): m/z=400.6 $(M+1)^+$.

Step 4 Synthesis of Compound 13a

Compound 12a (180 mg, 0.45 mmol) was added to a reaction flask, which was dissolved in 15 ml anhydrous DMF, and FDPP (207.5 mg, 0.54 mmol) and DIPEA (290.8 mg, 2.25 mmol) was added. The reaction was stirred at room temperature overnight under nitrogen protection. TLC was used to monitor the completion of the reaction. After completion, the reaction was diluted with an excess amount of water, and extracted with ethyl acetate for 3-4 times. The organic phases were combined, washed with saturated brine, concentrated and then purified by silica gel column chromatography to afford 103 mg of the title product. Yield: 60%. LC-MS (APCI): m/z=382.3 $(M+1)^+$. $^1H$ NMR (400 MHz. DMSO-$d_6$) δ 10.08 (s, 1H), 8.83 (s, 1H), 8.04 (d, J=2.3 Hz, 1H), 7.52 (s, 1H), 7.42 (d, J=3.3 Hz, 1H), 7.28 (d, J=3.3 Hz, 1H), 6.74 (d, J=2.3 Hz, 1H), 4.31 (m, 1H), 4.12 (m, 1H), 3.55 (dd, J=17.0, 9.3 Hz, 2H), 2.32 (t, J=4.4 Hz, 2H), 1.95-1.61 (m, 2H), 1.22 (d, J=4.5 Hz, 2H), 1.15 (d, J=4.4 Hz, 3H).

Step 5 Synthesis of Compounds L-2-A and L-2-B

Preparative chiral column: CHIRALPAK IC (brand name), 4.6 mm×250 mm (internal diameter×length), 5 μm (particle size of the filler)

Column temperature: 30° C.

Flow rate: 1.0 mL/min

UV detection wavelength: 254 nm

Mobile phase: methyl tert-butyl ether:methanol=70:30

Under the above preparative chiral column and chiral resolution conditions, racemic compound 13a was separated to afford target compound L-2-A (retention time: 27.06 min, relative amount: 27.7%) and L-2-B (retention time: 7.02 min, relative amount: 67.8%).

Example 9: Preparation of 9-fluoro-15,15-dimethyl-13-oxa-2,17,20,21,24-pentaazapentacyclo[16.5.2.$0^{2,6}$.$0^{7,12}$.$0^{21,25}$]pentacosane-1(24),7,9,11,18(25),19,22-heptaene-16-one (Compound 18a) (6R)-9-fluoro-15,15-dimethyl-13-oxa-2,17,20,21,24-pentaazapentacyclo[16.5.2.$0^{2,6}$.$0^{7,12}$.$0^{21,25}$]pentacosane-1(24),7,9,11,18(25),19,22-heptaene-16-one (Compound L-3-A), and (6S)-9-fluoro-15,15-dimethyl-13-oxa-2,17,20,21,24-pentaazapentacyclo[16.5.2.$0^{2,6}$.$0^{7,12}$.$0^{21,25}$]pentacosane-1(24),7,9,11,18(25),19,22-heptaene-16-one (Compound L-3-B)

18a

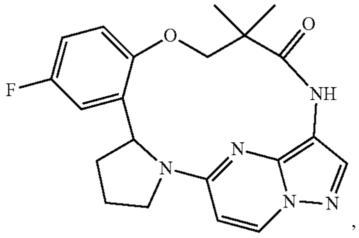

,

L-3-A

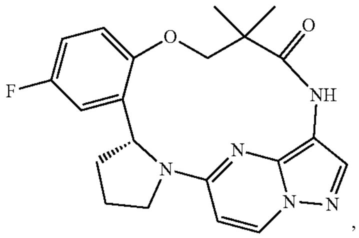

, and

L-3-B

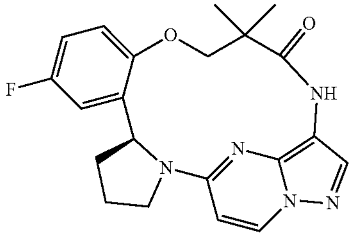

The following route was used for the synthesis:

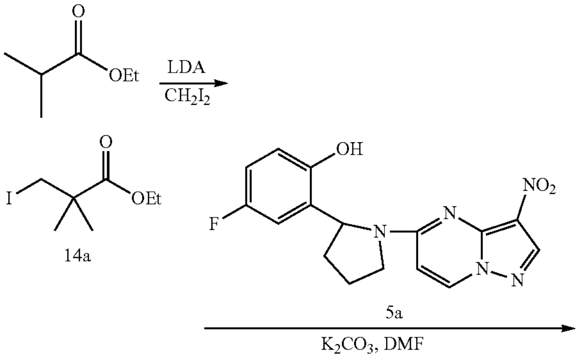

14a

5a

-continued

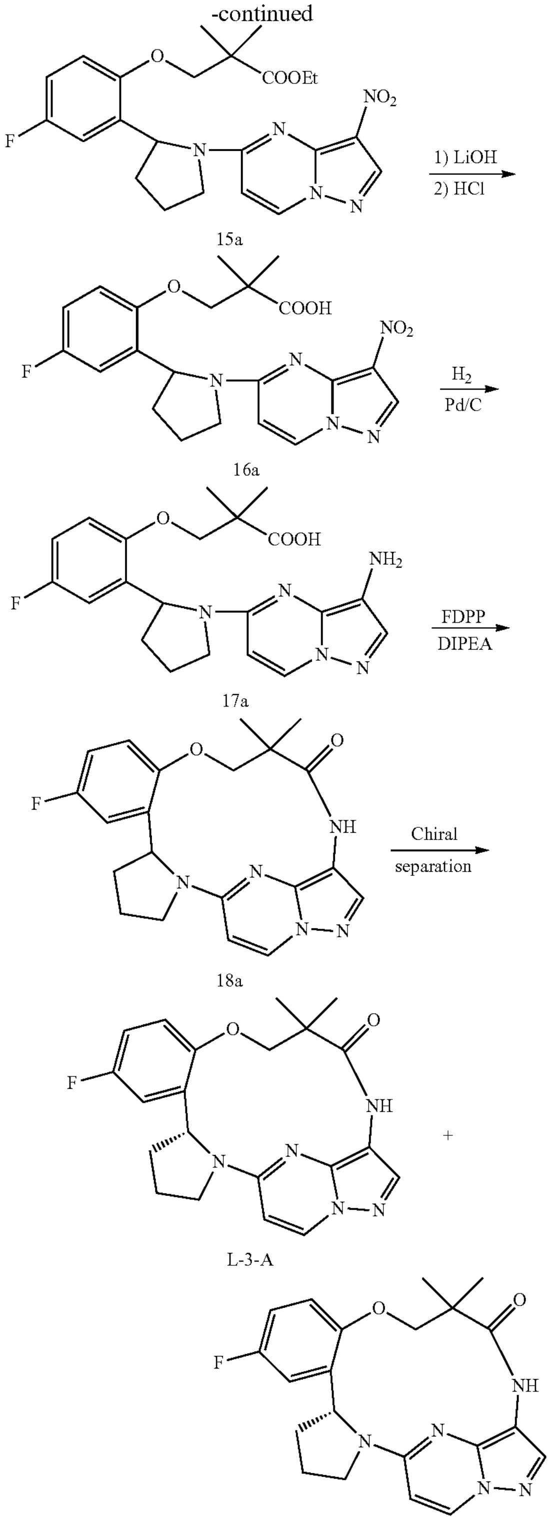

15a

16a

17a

18a

L-3-A

L-3-B

Step 1 Synthesis of Compound 14a

Ethyl isobutyrate (2.5 g, 21.5 mmol) was added to a reaction flask, and 40 ml anhydrous tetrahydrofuran was added under nitrogen protection. The mixture was cooled to −40° C., and LDA (11.8 ml, 23.6 mmol) was slowly added dropwise. After the addition, the reaction was gradually warmed to room temperature and stirred for half an hour.

Then it was cooled to −40° C., and a solution of diiodomethane (5.76 g, 21.5 mmol) in 10 ml anhydrous tetrahydrofuran was slowly added dropwise. After the addition, the reaction was warmed to room temperature and reacted overnight. Water was added to quench the reaction, the organic phase was separated, and the aqueous phase was extracted with ethyl acetate for 3-4 times. The organic phases were combined, washed with saturated brine, dried over anhydrous sodium sulfate, filtered and concentrated to afford 4.62 g of the product. Yield: 84%.

Step 2 Synthesis of Compound 15a

Compound 5a (326 mg, 0.95 mmol), compound 14a (291 mg, 1.14 mmol) and potassium carbonate (525.2 mg, 3.8 mmol) were added to a reaction flask, and DMF was added. The reaction was heated to 80° C. stirred and reacted overnight. TLC was used to monitor the completion of the reaction. After completion, the reaction was cooled to room temperature, added with an excess amount of water, and extracted with ethyl acetate for 3-4 times. The organic phases were combined, washed with saturated brine, concentrated and then purified by silica gel column chromatography to afford 300 mg of the title product. Yield: 67%, LC-MS (APCI): m/z=472.1 $(M+1)^+$.

Step 3 Synthesis of Compound 16a

Compound 15a (339 mg, 0.72 mmol) was added to a reaction flask, which was dissolved in 10 ml methanol, and a solution of lithium hydroxide monohydrate (151.5 mg, 3.5 mmol) in 3 ml water was added. The reaction was heated to 50° C. and reacted for 4-5 hours. TLC was used to monitor the completion of the reaction. The reaction was cooled to 0° C. pH thereof was adjusted to weak acidic with 1N dilute hydrochloric acid, and the reaction was extracted with ethyl acetate for 3-4 times. The organic phases were combined, dried over anhydrous sodium sulfate, filtered and concentrated to afford 296 mg of the product. Yield: 93%. LC-MS (APCI): m/z=444.3 $(M+1)^+$.

Step 4 Synthesis of Compound 17a

Compound 16a (297 mg, 0.67 mmol) was added to a reaction flask, which was dissolved in 10 ml methanol, and a catalytic amount of Pd/C was added. The reaction was filled with hydrogen gas, stirred and reacted at room temperature for 5-7 hours. TLC was used to monitor the completion of the reaction. After completion, the catalyst was removed by filtration, and the filtrate was concentrated to afford crude product of compound 17a, which was directly used in the next reaction without purification. LC-MS (APCI): m/z=414.9 $(M+1)^+$.

Step 5 Synthesis of Compound 18a

Compound 17a (277 mg, 0.67 mmol) was added to a reaction flask, which was dissolved in 20 ml anhydrous DMF, and FDPP (309 mg, 0.80 mmol) and DIPEA (433 mg, 3.35 mmol) were added. The reaction was stirred at room temperature overnight under nitrogen protection. TLC was used to monitor the completion of the reaction. After completion, the reaction was diluted with an excess amount of water, and extracted with ethyl acetate for 3-4 times. The organic phases were combined, washed with saturated brine, concentrated and then purified by silica gel column chromatography to afford 111 mg of the title product. Yield: 42%. LC-MS (APCI): m/z=396.3 $(M+1)^+$. $^1$H NMR (400 MHz, DMSO-d) δ 10.10 (s, 1H), 8.85 (s, 1H), 8.04 (d, J=2.3 Hz, 1H), 7.52 (s, 1H), 7.42 (d, J=3.3 Hz, 1H), 7.28 (d. J=3.3 Hz, 1H), 6.74 (d, J=2.3 Hz, 1H), 4.32 (t, J=4.4 Hz, 2H), 4.12 (m, 1H), 3.61 (dd, J=17.0, 9.3 Hz, 2H), 2.01-1.65 (m, 2H), 1.22 (d, J=4.5 Hz, 2H), 1.05 (s, 6H).

Step 6 Synthesis of Compounds L-3-A and L-3-B

Preparative chiral column: CHIRALPAK IC (brand name), 4.6 mm×250 mm (internal diameter×length), 5 μm (particle size of the filler)

Column temperature: 30° C.

Flow rate: 1.0 mL/min

UV detection wavelength: 254 nm

Mobile phase: methyl tert-butyl ether:methanol=70:30

Under the above preparative chiral column and chiral resolution conditions, racemic compound 18a was separated to afford target compound L-3-A (retention time: 24.2 min, relative amount: 33.1%) and L-3-B (retention time: 8.34 min, relative amount: 61.0%).

Example 10: Preparation of 9-fluoro-15-methyl-13-oxa-2,17,20,21,24-pentaazapentacyclo[16.5.2.$0^{2,6}.0^{7,12}.0^{21,25}$]pentacosane-1(24),7,9,11,18(25),19,22-heptaene-16-one (Compound 23a), (6R,1SR)-9-fluoro-15-methyl-13-oxa-2,17,20,21,24-pentaazapentacyclo[16.5.2.$0^{2,6}.0^{7,12}.0^{21,25}$]pentacosane-1(24),7,9,11,18(25),19,22-heptaene-16-one (Compound L-4-A), (6R,1SS)-9-fluoro-15-methyl-13-oxa-2,17,20,21,24-pentaazapentacyclo[16.5.2.$0^{2,6}.0^{7,12}.0^{21,25}$]pentacosane-1(24),7,9,11,18(25),19,22-heptaene-16-one (Compound L-4-B), (6S,15R)-9-fluoro-15-methyl-13-oxa-2,17,20,21,24-pentaazapentacyclo[16.5.2.$0^{2,6}.0^{7,12}.0^{21,25}$]pentacosane-1(24),7,9,11,18(25),19,22-heptaene-16-one (Compound L-4-C), and (6S,15S)-9-fluoro-15-methyl-13-oxa-2,17,20,21,24-pentaazapentacyclo[16.5.2.$0^{2,6}.0^{7,12}.0^{21,25}$]pentacosane-1(24),7,9,11,18(25),19,22-heptaene-16-one (Compound L-4-D)

23a

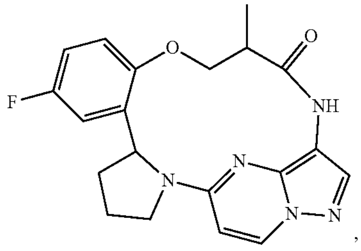

,

L-4-A

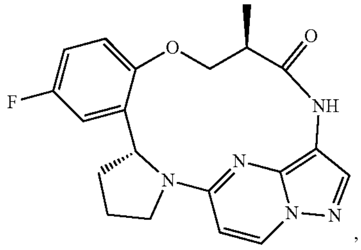

,

L-4-B

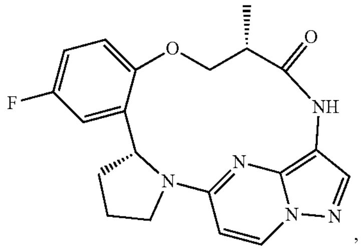

,

-continued
L-4-C
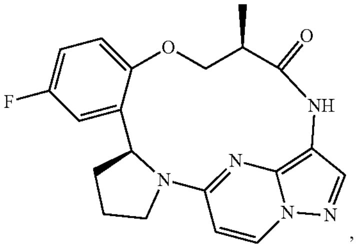
,
L-4-D
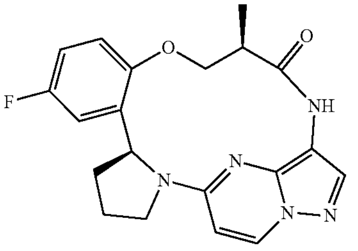
The following route was used for the synthesis:
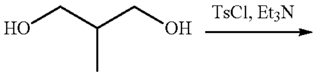
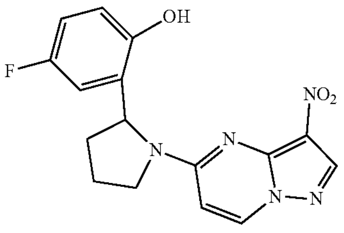
5a
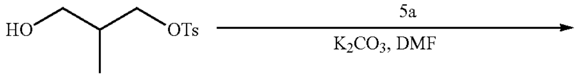
19a
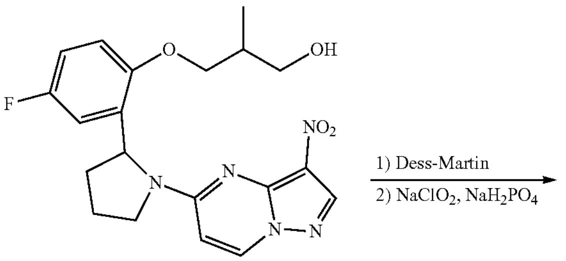
20a
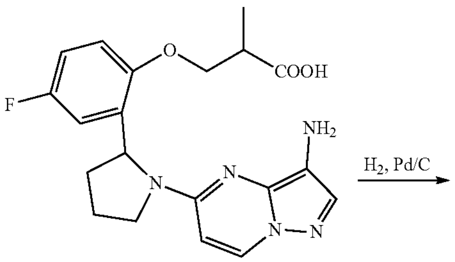
21a
-continued
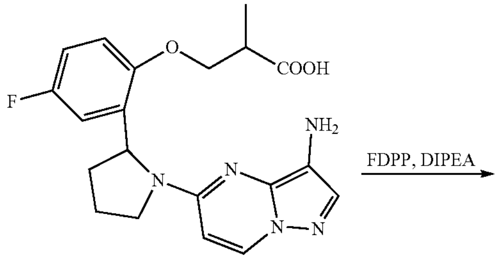
22a
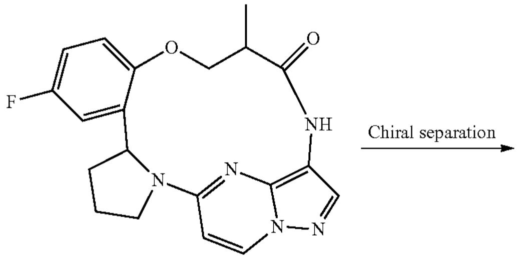
23a
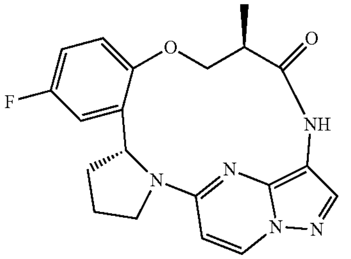
+
L-4-A
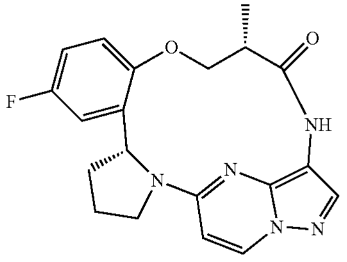
+
L-4-B
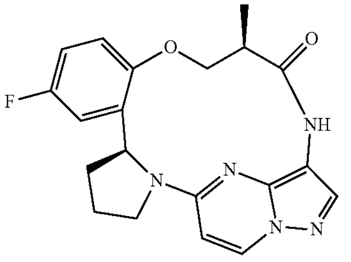
+
L-4-C -continued

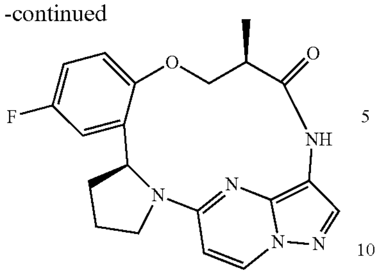

L-4-D

Step 1 Synthesis of Compound 19a 2-methyl-1,3-propanediol (2.0 g, 22.2 mmol) was dissolved in dichloromethane (30 ml), triethylamine (3.37 g, 33.3 mmol) was added under ice bath, and p-toluenesulfonyl chloride (TsCl, 4.23 g, 22.2 mmol) was added in batches while maintaining the temperature no higher than 5° C. After the addition, the reaction was stirred and reacted at the low temperature for 2-3 hours. TLC was used to monitor the completion of the reaction. After completion, 20 ml water was added, and the organic phase was separated, washed with saturated brine, concentrated and then purified by column chromatography to afford 3.52 g of compound 19a as colorless oily liquid. Yield: 65%. LC-MS (APCI): m/z=245.6 $(M+1)^+$.

Step 2 Synthesis of Compound 20a

Compound 5a (800 mg, 2.33 mmol) was dissolved in DMF (20 ml), and potassium carbonate (805 mg, 5.82 mmol) and compound 19a (854 mg, 3.49 mmol) were added. The reaction was heated to 80°, and stirred and reacted for 4-6 hours. TLC was used to monitor the completion of the reaction. After completion, the reaction was cooled to room temperature, added with an excess amount of water, and extracted with ethyl acetate for 3-4 times. The organic phases were combined, washed with saturated brine, concentrated and then purified by column chromatography to afford 691 mg of the light yellow solid. Yield: 71.4%. LC-MS (APCI): m/z=416.1 $(M+1)^+$.

Step 3 Synthesis of Compound 21a

Compound 20a (606 mg, 1.46 mmol) was dissolved in dichloromethane (20 ml), Dess-Martin oxidant (928 mg, 2.19 mmol) was added in batches under ice bath, and the reaction was gradually warmed to room temperature and stirred for 1 hour. TLC was used to monitor the completion of the reaction. After completion, the reaction was diluted with dichloromethane, washed 2-3 times with saturated sodium bicarbonate solution, and the organic phase was concentrated and directly used in the next reaction.

The intermediate obtained in the previous step was dissolved in acetonitrile (20 ml), sodium dihydrogen phosphate (876 mg, 7.3 mmol) was added, and a solution of sodium chlorite (264 mg, 2.92 mmol) in 5 ml water was added under ice bath, the reaction was gradually warmed to room temperature and stirred for 1 hour. TLC was used to monitor the completion of the reaction. After completion, the reaction was added with an excess amount of water, and extracted with ethyl acetate for 3-4 times. The organic phases were combined, washed with saturated brine, concentrated and then purified by column chromatography to afford 552 mg of compound 21a. Yield: 88%. LC-MS (APCI): m/z=430.4 $(M+1)^+$.

Step 4 Synthesis of Compound 22a

Compound 21a (540 mg, 1.26 mmol) was dissolved in methanol (15 ml), a catalytic amount of Pd/C was added, and the reaction was put under a balloon filled with hydrogen gas. The reaction was stirred and reacted at room temperature overnight. TLC was used to monitor the completion of the reaction. After completion, the catalyst was removed by filtration, and the filtrate was concentrated to afford 478 mg crude product of compound 22a, which was directly used in the next reaction. Yield: 95%. LC-MS (APCI): m/z=400.8 $(M+1)^+$.

Step 5 Synthesis of Compound 23a

Compound 22a (447 mg, 1.12 mmol) was dissolved in anhydrous DMF (20 ml), and DIPEA (580 mg, 4.48 mmol) and FDPP (516.4 mg, 1.34 mmol) were added. The reaction was stirred at room temperature overnight under nitrogen protection. TLC was used to monitor the completion of the reaction. After completion, the reaction was diluted with an excess amount of water, and extracted with ethyl acetate for 3-4 times. The organic phases were combined, washed with saturated brine, concentrated and then purified by column chromatography to afford 184 mg of compound 23a as light yellow solid. Yield: 43%. LC-MS (APCI): m/z=382.3 $(M+1)^+$. $^1H$ NMR (500 MHz, DMSO-$d_6$) δ 8.58 (s, 1H), 8.54 (d, J=7.6 Hz, 1H), 7.76 (s, 1H), 7.09 (d, J=7.2 Hz, 1H), 7.01-6.87 (m, 2H), 6.44 (d, J=7.6 Hz, 1H), 5.54 (s, 1H), 4.35-4.25 (m, 1H), 4.18 (t, J=10.6 Hz, 1H), 3.90 (d, J=9.2 Hz, 1H), 3.61 (s, 1H), 2.96 (s, 1H), 2.31 (s, 2H), 1.97 (d, J=7.0 Hz, 1H), 1.83 (d, J=5.0 Hz, 1H), 1.23 (d, J=7.1 Hz, 3H).

Step 6 Synthesis of Compounds L-4-A, L-4-B. L-4-C and L-4-D

Preparative chiral column: CHIRALPAK IC (brand name), 4.6 mm×250 mm (internal diameter×length), 5 μm (particle size of the filler)

Column temperature: 30° C.

Flow rate: 1.0 mL/min

UV detection wavelength: 254 nm

Mobile phase: methyl tert-butyl ether:methanol=70:30

Under the above preparative chiral column and chiral resolution conditions, racemic compound 23a was separated to afford target compound $L_4$-A (retention time: 6.28 min, relative amount: 22.3%), L-4-B (retention time: 18.46 min, relative amount: 22.4%), L-4-C (retention time: 30.45 min, relative amount: 22.2%) and L-4-D (retention time: 37.26 min, relative amount: 22.4%).

Example 11: Preparation of 9-fluoro-2,17,20,21,24-pentaazapentacyclo[16.5.2.$0^{2,6}$.$0^{7,12}$.$0^{21,25}$]pentacosane-1(24),7,9,11,18(25),19,22-heptaene-16-one (Compound 28a), (6R)-9-fluoro-2,17,20,21,24-pentaazapentacyclo[16.5.2.$0^{2,6}$.$0^{7,12}$.$0^{21,25}$]pentacosane-1(24),7,9,11,18(25),19,22-heptaene-16-one (Compound L-5-A), and (6S)-9-fluoro-2,17,20,21,24-pentaazapentacyclo[16.5.2.$0^{2,6}$.$0^{7,12}$.$0^{21,25}$]pentacosane-1(24),7,9,11,18(25),19,22-heptaene-16-one (Compound L-5-B)

28a

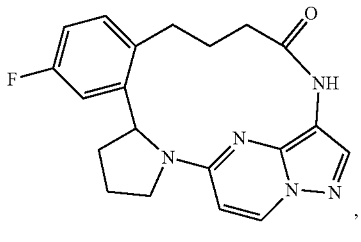

,

-continued

L-5-A

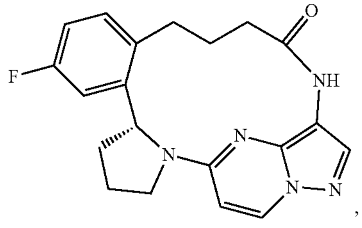

,

L-5-B

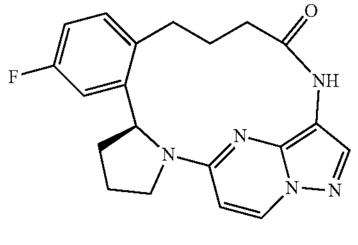

The following route was used for the synthesis:

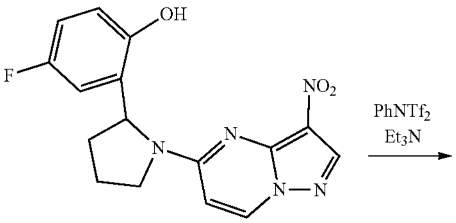

5a

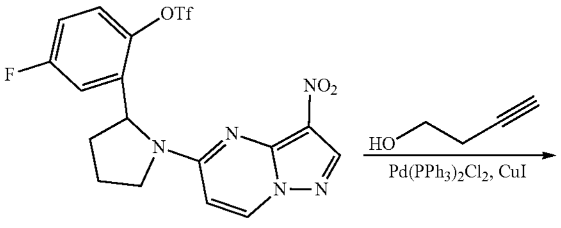

24a

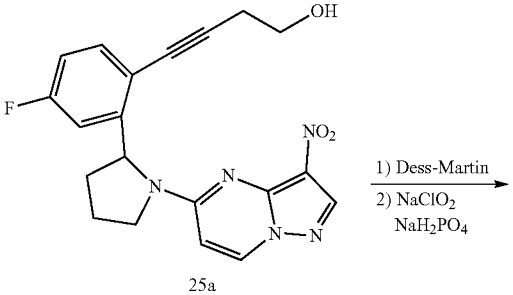

25a

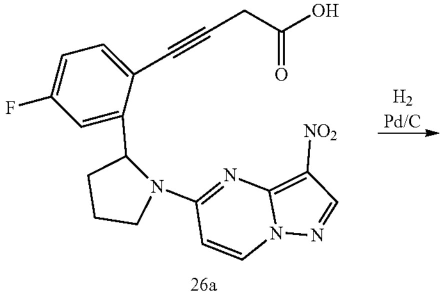

26a

-continued

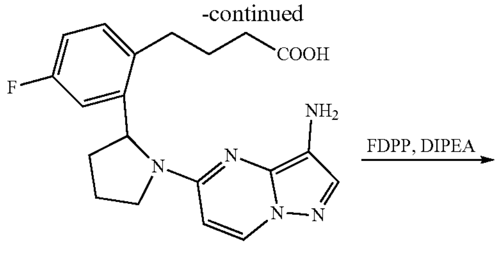

27a

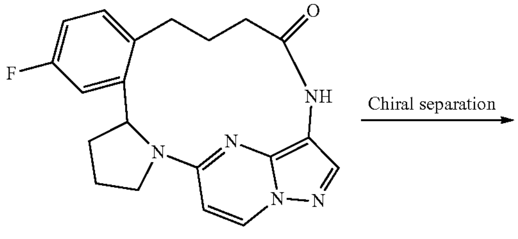

28a

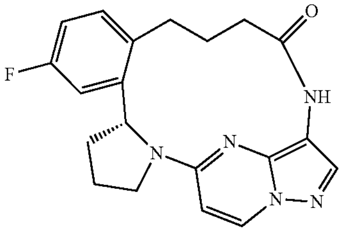

+

L-5-A

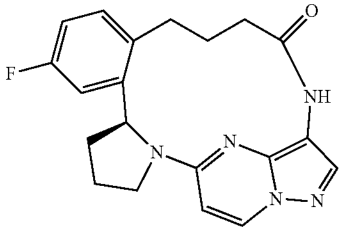

L-5-B

Step 1 Synthesis of Compound 24a

Compound 5a (1.0 g, 2.91 mmol) was dissolved in dichloromethane (30 ml), triethylamine (589.5 mg, 5.82 mmol) was added, and N,N-bis(trifluoromethylsulfonyl)aniline (1.25 g, 3.49 mmol). The reaction was stirred at room temperature overnight. TLC was used to monitor the completion of the reaction. After completion, the reaction was concentrated to remove the solvent, purified by silica gel column chromatography to afford 1.02 g of compound 24a as light yellow solid. Yield: 74%. LC-MS (APCI): m/z=476.4 $(M+1)^+$.

Step 2 Synthesis of Compound 25a

Compound 24a (1.42 g, 3 mmol) and 3-butyn-1-ol (315 mg, 4.5 mmol) were dissolved in dioxane (30 ml), bis(triphenylphosphine)palladium dichloride (21 mg, 0.03 mmol) and copper iodide (57 mg, 0.3 mmol) were added under nitrogen protection. The reaction was heated to 100° C. and stirred for 5 hours. TLC was used to monitor the completion of the reaction. After completion, the reaction was cooled to room temperature, diluted with water, and extracted with ethyl acetate for 3-4 times. The organic phases were combined, washed with saturated brine, concentrated and then purified by column chromatography to afford 854 mg of compound 25a as light yellow solid. Yield: 72%. LC-MS (APCI): m/z=396.8 $(M+1)^+$.

Step 3 Synthesis of Compound 26a

Compound 25a (577 mg, 1.46 mmol) was dissolved in dichloromethane (20 ml), Dess-Martin oxidant (928 mg, 2.19 mmol) was added in batches under ice bath, and the reaction was gradually warmed to room temperature and stirred for 1 hour. TLC was used to monitor the completion of the reaction. After completion, the reaction was diluted with dichloromethane, the resultant solution was washed 2-3 times with saturated sodium bicarbonate solution. After concentration, the organic phase was directly used in the next reaction.

The intermediate obtained in the previous step was dissolved in acetonitrile (20 ml), sodium dihydrogen phosphate (876 mg, 7.3 mmol) was added, and a solution of sodium chlorite (264 mg, 2.92 mmol) in 5 ml water was added under ice bath, and the reaction was gradually warmed to room temperature and stirred for 1 hour. TLC was used to monitor the completion of the reaction. After completion, the reaction was added with an excess amount of water, and extracted with ethyl acetate for 3-4 times. The organic phases were combined, washed with saturated brine, concentrated and then purified by column chromatography to afford 466 mg of compound 26a. Yield: 78%. LC-MS (APCI): m/z=410.2 $(M+1)^+$.

Step 4 Synthesis of Compound 27a

Compound 26a (515 mg, 1.26 mmol) was dissolved in methanol (15 ml), a catalytic amount of Pd/C was added, and the reaction was put under a balloon filled with hydrogen gas. The reaction was stirred and reacted at room temperature overnight. TLC was used to monitor the completion of the reaction. After completion, the catalyst was removed by filtration, and the filtrate was concentrated to afford 468.6 mg crude product of compound 27a, which was directly used in the next reaction. Yield: 97%. LC-MS (APCI): m/z=384.6 $(M+1)^+$.

Step 5 Synthesis of Compound 28a

Compound 27a (429 mg, 1.12 mmol) was dissolved in anhydrous DMF (20 ml), and DIPEA (580 mg, 4.48 mmol) and FDPP (516.4 mg, 1.34 mmol) were added. The reaction was stirred at room temperature overnight under nitrogen protection. TLC was used to monitor the completion of the reaction. After completion, the reaction was diluted with an excess amount of water, and extracted with ethyl acetate for 3-4 times. The organic phases were combined, washed with saturated brine, concentrated and then purified by column chromatography to afford 160 mg of compound 28a as light yellow solid. Yield: 39%. LC-MS (APCI): m/z=366.1 $(M+1)^+$. $^1$H NMR (500 MHz, DMSO-$d_6$) δ 8.76 (d, J=7.7 Hz, 1H), 8.42 (d, J=2.4 Hz, 1H), 7.62 (d, J=6.6 Hz, 1H), 7.59 (d, J=6.4 Hz, 1H), 7.57 (dd, J=9.9, 2.4 Hz, 1H), 7.22 (d, J=6.4 Hz, 1H), 6.60 (d, J=7.7 Hz, 1H), 5.36 (t, J=6.5 Hz, 1H), 4.05 (dd, J=16.9, 7.0 Hz, 2H), 3.75 (dd, J=14.0, 8.6 Hz, 1H), 3.67-3.51 (m, 1H), 2.95 (d, J=16.9 Hz, 1H), 2.55 (dd, J=14.0, 10.9 Hz, 1H), 2.42 (dd, J=13.4, 6.5 Hz, 2H), 2.23 (dd, J=12.0, 6.2 Hz, 2H), 2.12-1.96 (m, 1H), 1.79-1.66 (m 1H).

Step 6 Synthesis of Compounds L-5-A and L-5-B

Preparative chiral column: CHIRALPAK IC (brand name), 4.6 mm×250 mm (internal diameter×length), 5 μm (particle size of the filler)

Column temperature: 30° C.

Flow rate: 1.0 mL/min

UV detection wavelength: 254 nm

Mobile phase: methyl tert-butyl ether:methanol=70:30

Under the above preparative chiral column and chiral resolution conditions, racemic compound 28a was separated to afford target compound L-5-A (retention time: 6.28 min, relative amount: 44.6%) and L-5-B (retention time: 18.46 min, relative amount: 44.8%).

Example 12: Preparation of 9-fluoro-15-methyl-2,17,20,21,24-pentaazapentacyclo[16.5.2.0$^{2,6}$.0$^{7,12}$.0$^{21,25}$]pentacosane-1(24),7,9,11,18(25),19,22-heptaene-16-one (Compound 32a), (6R,15R)-9-fluoro-15-methyl-2,17,20,21,24-pentaazapentacyclo[16.5.2.0$^{2,6}$.0$^{7,12}$.0$^{21,25}$]pentacosane-1(24),7,9,11,18(25),19,22-heptaene-16-one (Compound L-6-A), (6R,15S)-9-fluoro-15-methyl-2,17,20,21,24-pentaazapentacyclo[16.5.2.0$^{2,6}$.0$^{7,12}$.0$^{21,25}$]pentacosane-1(24),7,9,11,18(25),19,22-heptaene-16-one (Compound L-6-B), (6S,15R)-9-fluoro-15-methyl-2,17,20,21,24-pentaazapentacyclo[16.5.2.0$^{2,6}$.0$^{7,12}$.0$^{21,25}$]pentacosane-1(24),7,9,11,18(25),19,22-heptaene-16-one (Compound L-6-C), and (6S,15S)-9-fluoro-15-methyl-2,17,20,21,24-pentaazapentacyclo[16.5.2.0$^{2,6}$.0$^{7,12}$.0$^{21,25}$]pentacosane-1(24),7,9,11,18(25),19,22-heptaene-16-one (Compound L-6-D)

32a

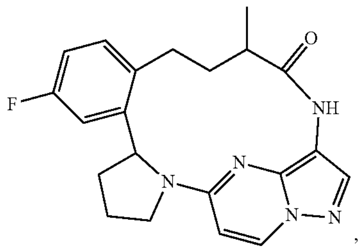

,

L-6-A

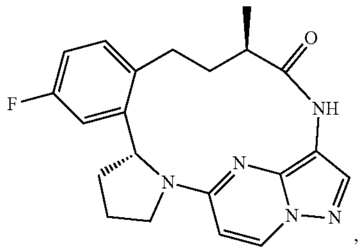

,

L-6-B

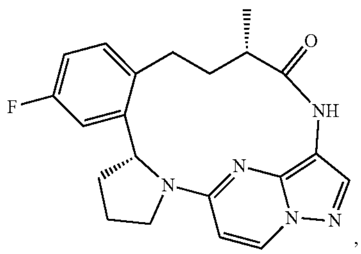

,

L-6-C

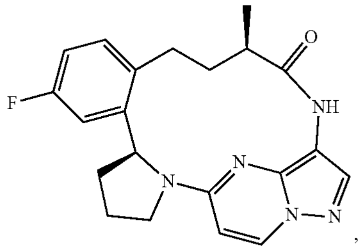

,

-continued

L-6-D

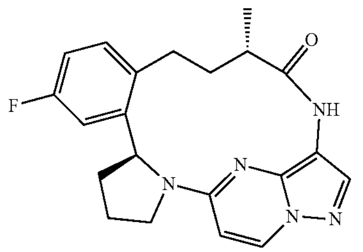

The following route was used for the synthesis:

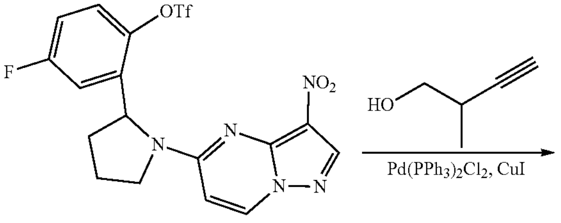

24a

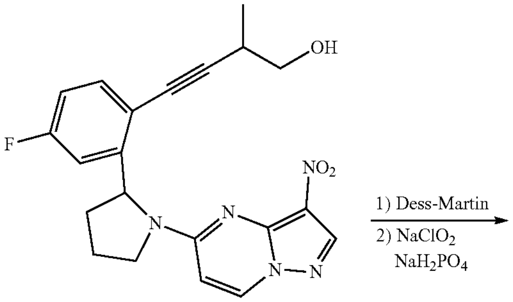

29a

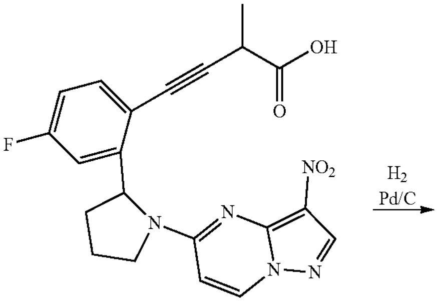

30a

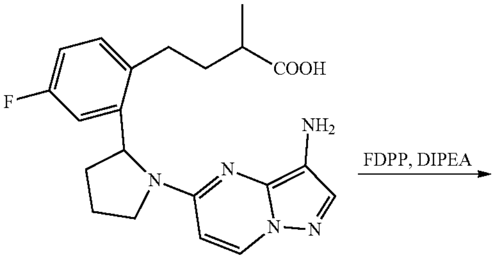

31a

-continued

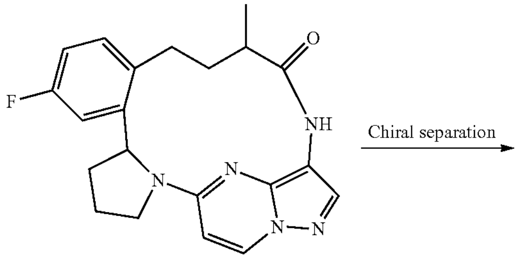

32a

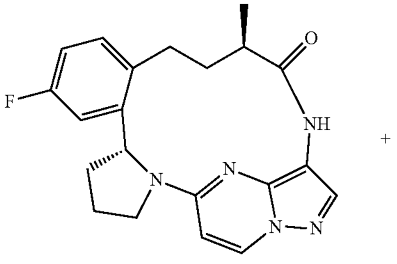

L-6-A

+

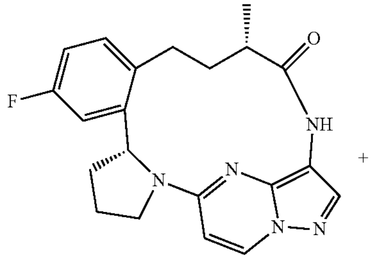

L-6-B

+

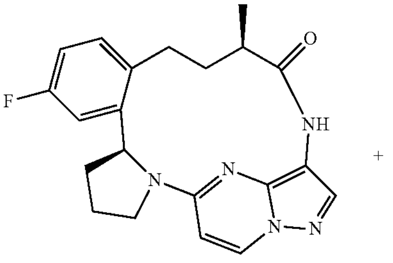

L-6-C

+

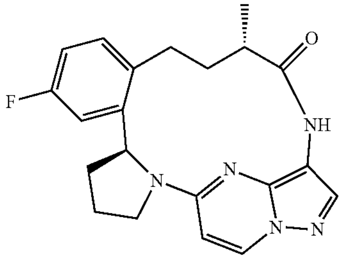

L-6-D

Step 1 Synthesis of Compound 29a

Compound 24a (1.42 g, 3 mmol) and 2-methyl-3-butyn-1-ol (364 mg, 4.5 mmol) were dissolved in dioxane (30 ml), bis(triphenylphosphine)palladium dichloride (21 mg, 0.03 mmol) and copper iodide (57 mg, 0.3 mmol) were added under nitrogen protection. The reaction was heated to 100° C. and stirred for 5 hours. TLC was used to monitor the completion of the reaction. After completion, the reaction was cooled to room temperature, diluted with water, and extracted with ethyl acetate for 3-4 times. The organic phases were combined, washed with saturated brine, concentrated and then purified by column chromatography to afford 773 mg of compound 29a as light yellow solid. Yield: 63%. LC-MS (APCI): m/z=410.1 $(M+1)^+$.

Step 2 Synthesis of Compound 30a

Compound 29a (597 mg, 1.46 mmol) was dissolved in dichloromethane (20 ml), Dess-Martin oxidant (928 mg, 2.19 mmol) was added in batches under ice bath, and the reaction was gradually warmed to room temperature and stirred for 1 hour. TLC was used to monitor the completion of the reaction. After completion, the reaction was diluted with dichloromethane, and washed 2-3 times with saturated sodium bicarbonate solution. After concentration, the organic phase was directly used in the next reaction.

The intermediate obtained in the previous step was dissolved in acetonitrile (20 ml), sodium dihydrogen phosphate (876 mg, 7.3 mmol) was added, and a solution of sodium chlorite (264 mg, 2.92 mmol) in 5 ml water was added under ice bath, and the reaction was gradually warmed to room temperature and stirred for 1 hour. TLC was used to monitor the completion of the reaction. After completion, the reaction was added with an excess amount of water, and extracted with ethyl acetate for 3-4 times. The organic phases were combined, washed with saturated brine, concentrated and then purified by column chromatography to afford 550 mg of compound 30a. Yield: 89%. LC-MS (APCI): m/z=424.2 $(M+1)^+$.

Step 3 Synthesis of Compound 31a

Compound 30a (533 mg, 1.26 mmol) was dissolved in methanol (15 ml), a catalytic amount of Pd/C was added, and the reaction was put under a balloon filled with hydrogen gas. The reaction was stirred and reacted at room temperature overnight. TLC was used to monitor the completion of the reaction. After completion, the catalyst was removed by filtration, and the filtrate was concentrated to afford 485.7 mg crude product of compound 31a, which was directly used in the next reaction. Yield: 97%. LC-MS (APCI): m/z=398.9 $(M+1)^+$.

Step 4 Synthesis of Compound 32a

Compound 31a (445 mg, 1.12 mmol) was dissolved in anhydrous DMF (20 ml), and DIPEA (580 mg, 4.48 mmol) and FDPP (516.4 mg, 1.34 mmol) were added. The reaction was stirred at room temperature overnight under nitrogen protection. TLC was used to monitor the completion of the reaction. After completion, the reaction was diluted with an excess amount of water, and extracted with ethyl acetate for 3-4 times. The organic phases were combined, washed with saturated brine, concentrated and then purified by column chromatography to afford 187 mg of compound 32a as light yellow solid. Yield: 44%. LC-MS (APCI): m/z=380.1 $(M+1)^+$. $^1H$ NMR (500 MHz, DMSO-d) δ 8.76 (d, J=7.7 Hz, 1H), 8.42 (d, J=2.4 Hz, 1H), 7.62 (d, J=6.6 Hz, 1H), 7.59 (d, J=6.4 Hz, 1H), 7.57 (dd, J=9.9, 2.4 Hz, 1H), 7.22 (d, J=6.4 Hz, 1H), 6.60 (d, J=7.7 Hz, 1H), 5.36 (t, J=6.5 Hz, 1H), 4.05 (dd, J=16.9, 7.0 Hz, 2H), 3.75 (dd, J=14.0, 8.6 Hz, 1H), 3.67-3.51 (m, 1H), 2.95 (d, J=16.9 Hz, 1H), 2.42 (dd, J=13.4, 6.5 Hz, 2H), 2.23 (dd, J=12.0.6.2 Hz, 2H),2.12-1.96 (m, 1H), 1.88 (d, J=6.9 Hz, 3H), 1.79-1.66 (m, 1H).

Step 5 Synthesis of Compounds L-6-A, L-6-B, L-6-C and $L_4$-D

Preparative chiral column: CHIRALPAK IC (brand name), 4.6 mm×250 mm (internal diameter×length), 5 μm (particle size of the filler)

Column temperature: 30° C.

Flow rate: 1.0 mL/min

UV detection wavelength: 254 nm

Mobile phase: methyl tert-butyl ether:methanol=70:30

Under the above preparative chiral column and chiral resolution conditions, racemic compound 32a was separated to afford target compound L-6-A (retention time: 7.14 min, relative amount: 21.6%), L-6-B (retention time: 15.69 min, relative amount: 22.8%). L-6-C (retention time: 29.54 min, relative amount: 17.6%) and L-6-D (retention time: 34.26 min. relative amount: 16.9%).

Example 13: Preparation of 9-fluoro-15-methyl-2,11,17,20,21,24-hexaazapentacyclo[16.5.2.$0^{2,6}$.$0^{7,12}$.$0^{21,25}$]pentacosane-1(24),7,9,11,18(25),19,22-heptaene-16-one (Compound 41a), (6R,15R)-9-fluoro-15-methyl-2,11,17,20,21,24-hexaazapentacyclo[16.5.2.$0^{2,6}$.$0^{7,12}$.$0^{21,25}$]pentacosane-1(24),7,9,11,18(25),19,22-heptaene-16-one (Compound L-7-A), (6R,15S)-9-fluoro-15-methyl-2,11,17,20,21,24-hexaazapentacyclo[16.5.2.$0^{2,6}$.$0^{7,12}$.$0^{21,25}$]pentacosane-1(24),7,9,11,18(25),19,22-heptaene-16-one (Compound L-7-B), (6S,15R)-9-fluoro-15-methyl-2,11,17,20,21,24-hexaazapentacyclo[16.5.2.$0^{2,6}$.$0^{7,12}$.$0^{21,25}$]pentacosane-1(24),7,9,11,18(25),19,22-heptaene-16-one (Compound L-7-C), and (6S,15S)-9-fluoro-15-methyl-2,11,17,20,21,24-hexaazapentacyclo[16.5.2.$0^{2,6}$.$0^{7,12}$.$0^{21,25}$]pentacosane-1(24),7,9,11,18(25),19,22-heptaene-16-one (Compound L-7-D)

41a

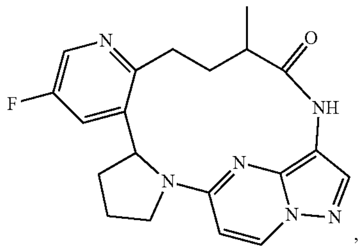

,

L-7-A

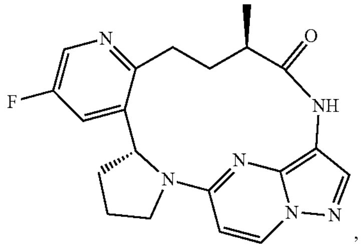

,

L-7-B

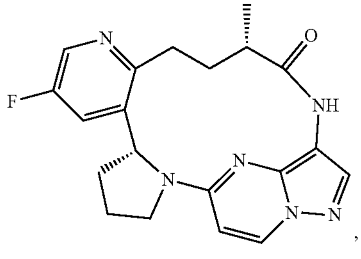

,

-continued
L-7-C
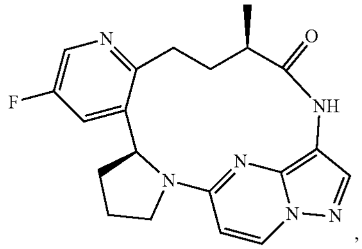
,
L-7-D
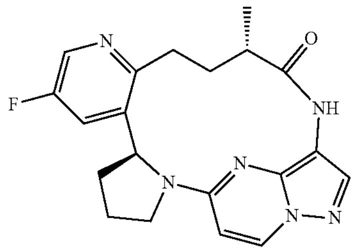
The following route was used for the synthesis:
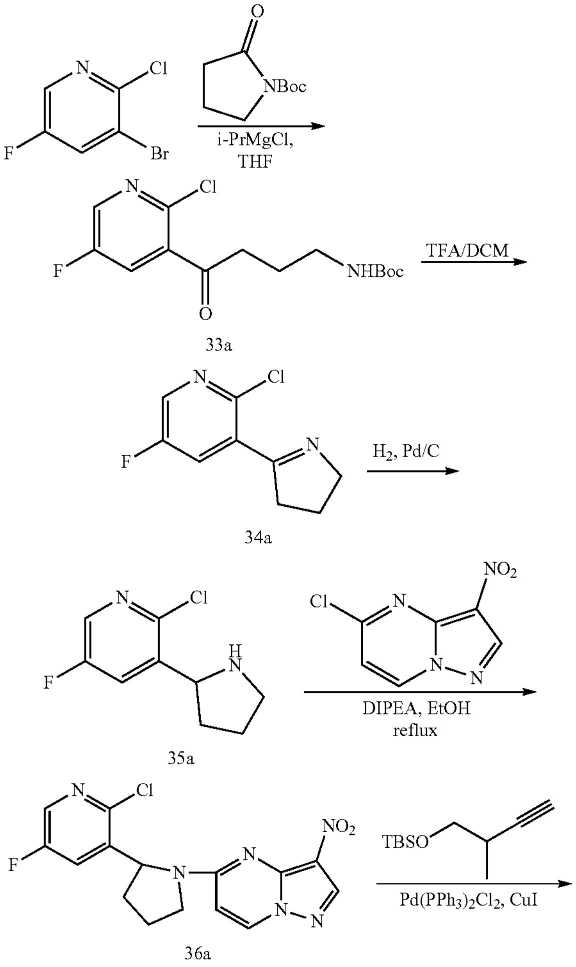
-continued
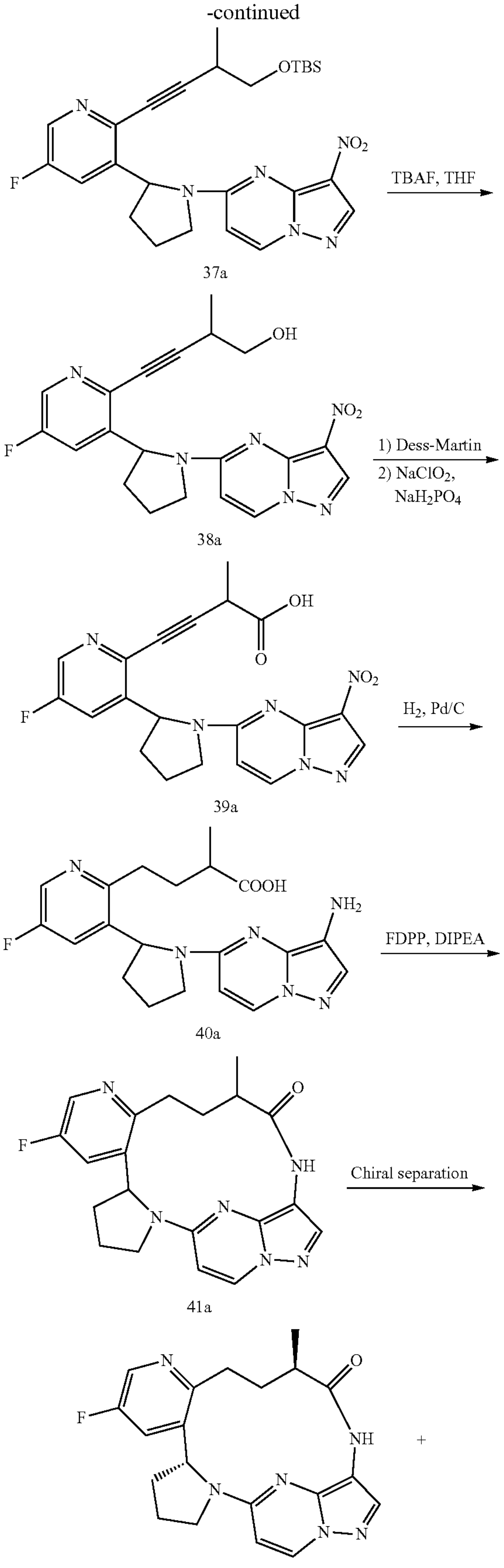
L-7-A -continued

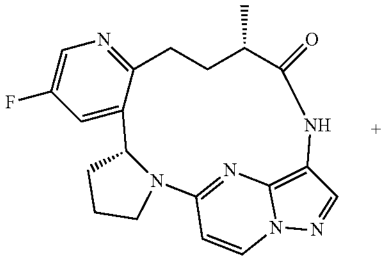

L-7-B

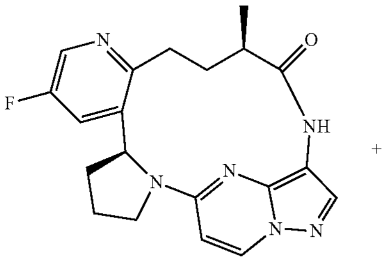

L-7-C

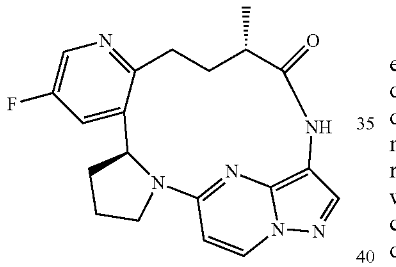

L-7-D

Step 1 Synthesis of Compound 33a 2-chloro-3-bromo-5-fluoropyridine (19.53 g, 93 mmol) was dissolved in anhydrous THF (100 mL), and isopropyl magnesium chloride solution (43.4 mL, 86.8 mmol) was slowly added dropwise at −40° C. After the addition, the mixture was naturally warmed to 0° C. and stirred for 1 h and a solution of N-tert-butoxycarbonyl-2-pyrrolidone (11.46 g, 62.0 mmol) in anhydrous tetrahydrofuran (30 mL) was then slowly added dropwise at −40° C. After the addition, the mixture was stirred at room temperature for 30 min. The reaction solution was poured into 100 mL of saturated ammonium chloride solution and stirred for 10 min, then the reaction solution was separated by standing. The aqueous phase was extracted three times with 40 mL ethyl acetate. The organic phases were combined and washed with saturated brine, dried over anhydrous sodium sulfate. The residue was filtered and concentrated, purified by column chromatography to afford 19.5 g of compound 33a as light yellow liquid. Yield: 66.3%. LC-MS (APCI): m/z=317.2 $(M+1)^+$.

Step 2 Synthesis of Compound 34a

Compound 33a (1.22 g, 3.85 mmol) was dissolved in dichloromethane (10 mL), 2 mL trifluoroacetic acid was added, and the mixture was stirred at room temperature for 1 h. TLC was used to monitor the completion of the reaction. The reaction solution was washed with saturated sodium bicarbonate aqueous solution, the organic phase was separated, and the aqueous phase was extracted 3 times with dichloromethane. The organic phases were combined, washed with saturated brine, concentrated to afford crude product of compound 34a, which was directly used in the next reaction. LC-MS (APCI): m/z=199.3 $(M+1)^+$.

Step 3 Synthesis of Compound 35a

Compound 34a (764 mg, 3.85 mmol) was dissolved in anhydrous methanol (10 mL), Pd/C (50 mg) was added, and hydrogenated at room temperature overnight. The reaction was filtered, the filter residue was washed with 20 mL ethyl acetate, and the filtrate was concentrated to afford 726 mg of compound 35a as colorless oily liquid which was directly used in the next step. Yield: 95%. LC-MS (APCI): m/z=201.3 $(M+1)^+$.

Step 4 Synthesis of Compound 36a

Compound 35a (742 mg, 3.7 mmol) and 5-chloro-3-nitropyrazolo[1,5-a]pyrimidine (733 mg, 3.7 mmol) were dissolved in absolute ethanol (10 mL), DIPEA (1.91 g, 14.8 mmol) was added at room temperature, and the reaction was heated to reflux for 30 min. The reaction solution was concentrated, purified by column chromatography (PE/EA, 30%-50%) to afford 1.09 g of compound 36a as light yellow solid powder. Yield: 81%. LC-MS (APCI): m/z=363.5 $(M+1)^+$.

Step 5 Synthesis of Compound 37a

Compound 36a (1.09 g, 3 mmol) and 4-((tert-butyldimethylsilyl)oxo)-3-methylbutyne (893 mg, 4.5 mmol) were dissolved in dioxane (30 ml), bis(triphenylphosphine)palladium dichloride (21 mg, 0.03 mmol) and copper iodide (57 mg, 0.3 mmol) were added under nitrogen protection. The reaction was heated to 100° C. and stirred for 5 hours. TLC was used to monitor the completion of the reaction. After completion, the reaction was cooled to room temperature, diluted with water, and extracted with ethyl acetate for 3-4 times. The organic phases were combined, washed with saturated brine, concentrated and then purified by column chromatography to afford 936 mg of compound 37a as light yellow solid. Yield: 59.5%. LC-MS (APCI): m/z=525.8 $(M+1)^+$.

Step 6 Synthesis of Compound 38a

Compound 37a (936 mg, 1.78 mmol) was dissolved in anhydrous tetrahydrofuran (20 ml), a solution of 1M tetrabutylammonium fluoride in tetrahydrofuran (3.6 ml, 3.6 mmol) was slowly added dropwise. After the addition, the reaction was stirred and reacted for half an hour. TLC was used to monitor the completion of the reaction. After completion, the reaction was concentrated to remove the solvent, purified by silica gel column chromatography to afford 599 mg of compound 38a. Yield: 82%. LC-MS (APCI): m/z=411.1 $(M+1)^+$.

Step 7 Synthesis of Compound 39a

Compound 38a (599 mg, 1.46 mmol) was dissolved in dichloromethane (20 ml), Dess-Martin oxidant (928 mg, 2.19 mmol) was added in batches under ice bath, the reaction was gradually warmed to room temperature and stirred for 1 hour. TLC was used to monitor the completion of the reaction. After completion, the reaction was diluted with dichloromethane, and washed 2-3 times with saturated sodium bicarbonate solution. After concentration, the organic phase was directly used in the next reaction.

The intermediate obtained in the previous step was dissolved in acetonitrile (20 ml), sodium dihydrogen phosphate (876 mg, 7.3 mmol) was added, and a solution of sodium chlorite (264 mg, 2.92 mmol) in 5 ml water was added under ice bath, and the reaction was gradually warmed to room temperature and stirred for 1 hour. TLC was used to monitor the completion of the reaction. After completion, the reaction was added with an excess amount of water, and extracted with ethyl acetate for 3-4 times. The organic phases were combined, washed with saturated brine, concentrated and then purified by column chromatography to afford 533 mg of compound 39a. Yield: 86.1%. LC-MS (APCI): m/z=425.7 $(M+1)^+$.

Step 8 Synthesis of Compound 40a

Compound 39a (533 mg, 1.26 mmol) was dissolved in methanol (15 ml), a catalytic amount of Pd/C was added, and the reaction was put under a balloon filled with hydrogen gas. The reaction was stirred and reacted at room temperature overnight. TLC was used to monitor the completion of the reaction. After completion, the catalyst was removed by filtration, and the filtrate was concentrated to afford 446.7 mg crude product of compound 40a, which was directly used in the next reaction. Yield: 89%. LC-MS (APCI): m/z=399.7 $(M+1)^+$.

Step 9 Synthesis of Compound 41a

Compound 40a (446.7 mg, 1.12 mmol) was dissolved in anhydrous DMF (20 ml), and DIPEA (580 mg, 4.48 mmol) and FDPP (516.4 mg, 1.34 mmol) were added. The reaction was stirred at room temperature overnight under nitrogen protection. TLC was used to monitor the completion of the reaction. After completion, the reaction was diluted with an excess amount of water, and extracted with ethyl acetate for 3-4 times. The organic phases were combined, washed with saturated brine, concentrated and then purified by column chromatography to afford 200.2 mg of compound 41a as light yellow solid. Yield: 47%. LC-MS (APCI): m/z=381.4 $(M+1)^+$. $^1H$ NMR (500 MHz, DMSO-$d_6$) δ 8.70 (d, J=7.7 Hz, 1H), 8.39 (d, J=2.4 Hz, 1H), 8.01 (s, 1H), 7.66 (d. J=6.6 Hz, 1H), 7.57 (dd, J=9.9, 2.4 Hz, 1H), 6.60 (d, J=7.7 Hz, 1H), 5.36 (t, J=6.5 Hz, 1H), 4.03 (dd, J=16.9, 7.0 Hz, 2H), 3.75 (dd, J=14.0, 8.6 Hz, 1H), 3.67-3.51 (m, 1H), 2.91 (d, J=16.9 Hz, 1H), 2.54 (dd, J=14.0, 10.9 Hz, 1H), 2.44 (dd, J=13.4, 6.5 Hz, 1H), 2.23 (dd, J=12.0, 6.2 Hz, 2H), 2.12-1.96 (m, 1H), 1.79-1.66 (m, 1H), 1.13 (d, J=6.6 Hz, 3H).

Step 10 Synthesis of Compound L-7-A, L-7-B, L-7-C and L-7-D

Preparative chiral column: CHIRALPAK IC (brand name), 4.6 mm×250 mm (internal diameter×length), 5 μm (particle size of the filler)

Column temperature: 30° C.

Flow rate: 1.0 mL/min

UV detection wavelength: 254 nm

Mobile phase: methyl tert-butyl ether:methanol=70:30

Under the above preparative chiral column and chiral resolution conditions, racemic compound 41a was separated to afford target compound L-7-A (retention time: 4.77 min, relative amount: 30.21%), L-7-B (retention time: 15.68 min, relative amount: 22.5%). L-7-C (retention time: 26.31 min, relative amount: 10.66%) and L-7-D (retention time: 29.67 min, relative amount: 23.4%).

Example 14: Preparation of 9-fluoro-2,11,17,20,21,24-hexaazapentacyclo[16.5.2.$0^{2,6}$.$0^{7,12}$.$0^{21,25}$]pentacosane-1(24),7,9,11,18(25),19,22-heptaene-16-one (Compound 45a), (6R)-9-fluoro-2,11,17,20,21,24-hexaazapentacyclo[16.5.2.$0^{2,6}$.$0^{7,12}$.$0^{21,25}$]pentacosane-1(24),7,9,11,18(25),19,22-heptaene-16-one (Compound L-8-A), and (6S')-9-fluoro-2,11,17,20,21,24-hexaazapentacyclo[16.5.2.$0^{2,6}$.$0^{7,12}$.$0^{21,25}$]pentacosane-1(24),7,9,11,18(25),19,22-heptaene-16-one (Compound L-8-B)

45a

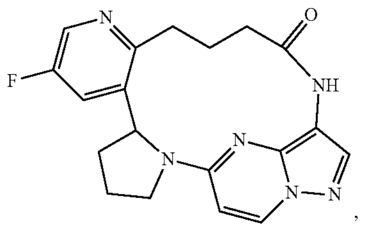

,

L-8-A

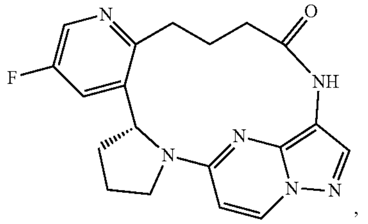

,

L-8-B

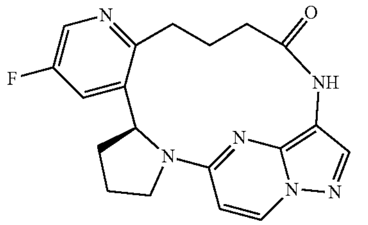

The following route was used for the synthesis:

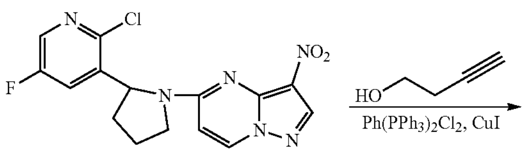

36a

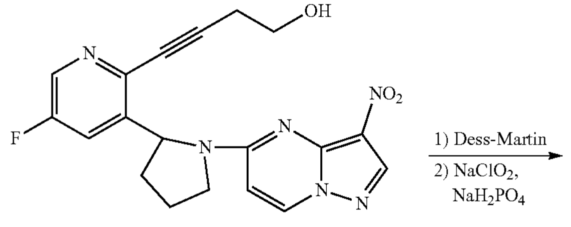

42a

-continued

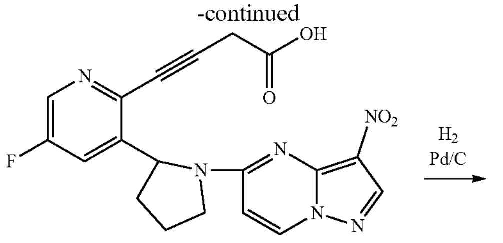

43a

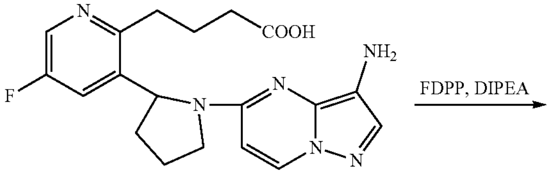

44a

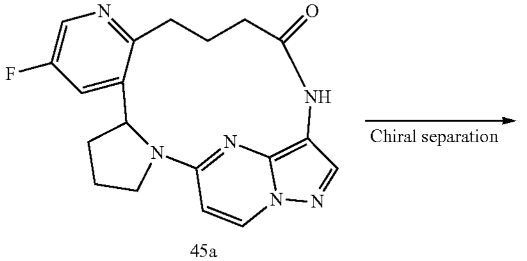

45a

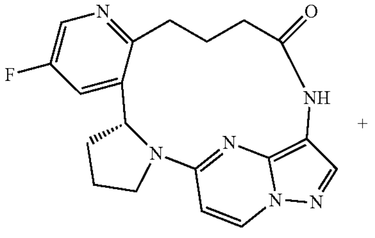

L-8-A

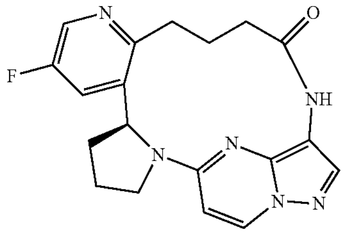

L-8-B

Step 1 Synthesis of Compound 42a

Compound 36a (1.09 g, 3 mmol) and 3-butyn-1-ol (315 mg, 4.5 mmol) were dissolved in dioxane (30 ml), bis (triphenylphosphine)palladium dichloride (21 mg, 0.03 mmol) and copper iodide (57 mg, 0.3 mmol) were added under nitrogen protection. The reaction was heated to 100° C. and stirred for 5 hours. TLC was used to monitor the completion of the reaction. After completion, the reaction was cooled to room temperature, diluted with water, and extracted with ethyl acetate for 3-4 times. The organic phases were combined, washed with saturated brine, concentrated and then purified by column chromatography to afford 845 mg of compound 42a as light yellow solid. Yield: 66%. LC-MS (APCI): m/z=397.1 $(M+1)^+$.

Step 2 Synthesis of Compound 43a

Compound 42a (578 mg, 1.46 mmol) was dissolved in dichloromethane (20 ml), Dess-Martin oxidant (928 mg, 2.19 mmol) was added in batches under ice bath, and the reaction was gradually warmed to room temperature and stirred for 1 hour. TLC was used to monitor the completion of the reaction. After completion, the reaction was diluted with dichloromethane, the resultant solution was washed 2-3 times with saturated sodium bicarbonate solution. After concentration, the organic phase was directly used in the next reaction.

The intermediate obtained in the previous step was dissolved in acetonitrile (20 ml), sodium dihydrogen phosphate (876 mg, 7.3 mmol) was added, and a solution of sodium chlorite (264 mg, 2.92 mmol) in 5 ml water was added under ice bath, and the reaction was gradually warmed to room temperature and stirred for 1 hour. TLC was used to monitor the completion of the reaction. After completion, the reaction was added with an excess amount of water, and extracted with ethyl acetate for 3-4 times. The organic phases were combined, washed with saturated brine, concentrated and then purified by column chromatography to afford 485 mg of compound 43a. Yield: 81%. LC-MS (APCI): m/z=411.4 $(M+1)^+$.

Step 3 Synthesis of Compound 44a

Compound 43a (517 mg, 1.26 mmol) was dissolved in methanol (15 ml), a catalytic amount of Pd/C was added, and the reaction was put under a balloon filled with hydrogen gas. The reaction was stirred and reacted at room temperature overnight. TLC was used to monitor the completion of the reaction. After completion, the catalyst was removed by filtration, and the filtrate was concentrated to afford 450.4 mg crude product of compound 44a, which was directly used in the next reaction. Yield: 93%. LC-MS (APCI): m/z=385.7 $(M+1)^+$.

Step 4 Synthesis of Compound 45a

Compound 44a (430.5 mg, 1.12 mmol) was dissolved in anhydrous DMF (20 ml), and DIPEA (580 mg, 4.48 mmol) and FDPP (516.4 mg, 1.34 mmol) were added. The reaction was stirred at room temperature overnight under nitrogen protection. TLC was used to monitor the completion of the reaction. After completion, the reaction was diluted with an excess amount of water, and extracted with ethyl acetate for 3-4 times. The organic phases were combined, washed with saturated brine, concentrated and then purified by column chromatography to afford 232.7 mg of compound 45a as light yellow solid. Yield: 56.7%. LC-MS (APCI): m/z=367.6 $(M+1)^+$. $^1H$ NMR (500 MHz, DMSO-$d_6$) δ 8.76 (d. J=7.7 Hz, 1H), 8.42 (d, J=2.4 Hz, 1H), 8.01 (s, 1H), 7.62 (d. J=6.6 Hz, 1H), 7.57 (dd, J=9.9, 2.4 Hz, 1H), 6.60 (d, J=7.7 Hz, 1H), 5.36 (t, J=6.5 Hz, 1H), 4.05 (dd, J=16.9, 7.0 Hz, 2H), 3.75 (dd, J=14.0, 8.6 Hz, 1H), 3.67-3.51 (m, 1H), 2.91 (d, J=16.9 Hz, 1H), 2.54 (dd, J=14.0, 10.9 Hz, 1H), 2.44 (dd, J=13.4, 6.5 Hz, 2H), 2.23 (dd, J=12.0, 6.2 Hz, 2H), 2.12-1.96 (m 1H), 1.79-1.66 (m, 1H).

Step 5 Synthesis of Compounds L-8-A and L-8-B

Preparative chiral column: CHIRALPAK IC (brand name), 4.6 mm×250 mm (internal diameter×length), 5 μm (particle size of the filler)

Column temperature: 30° C.

Flow rate: 1.0 mL/min

UV detection wavelength: 254 nm

Mobile phase: methyl tert-butyl ether:methanol=70:30

Under the above preparative chiral column and chiral resolution conditions, racemic compound 45a was separated to afford target compound L-8-A (retention time: 20.15 min, relative amount: 43.7%) and L-8-B (retention time: 8.25 min, relative amount: 44.0%).

Example 15: Preparation of (4R)-9-fluoro-4-hydroxy-2,11,17,20,21,24-hexaazapentacyclo[16.5.2.0$^{2,6}$.0$^{7,12}$.0$^{21,25}$]pentacosane-1(24),7,9,11,18(25),19,22-heptaene-16-one (Compound 56a), (4R,6R)-9-fluoro-4-hydroxy-2,11,17,20,21,24-hexaazapentacyclo[16.5.2.0$^{2,6}$.0$^{7,12}$.0$^{21,25}$]pentacosane-1(24),7,9,11,18(25),19,22-heptaene-16-one (Compound L-9-A), and (4R,6S)-9-fluoro-4-hydroxy-2,11,17,20,21,24-hexaazapentacyclo[16.5.2.0$^{2,6}$.0$^{7,12}$.0$^{21,25}$]pentacosane-1(24),7,9,11,18(25),19,22-heptaene-16-one (Compound L-9-B)

56a

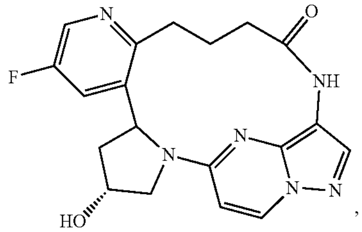

,

L-9-A

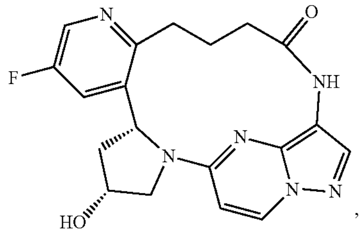

,

L-9-B

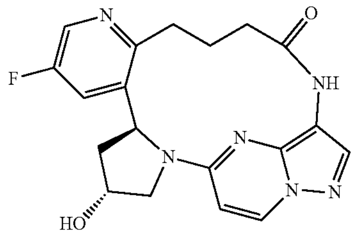

The following route was used for the synthesis:

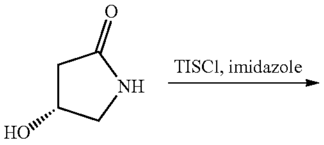

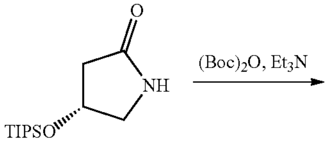

46a

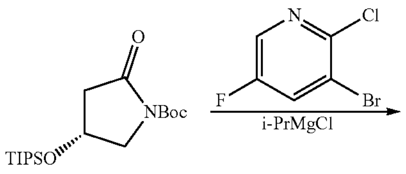

47a

-continued

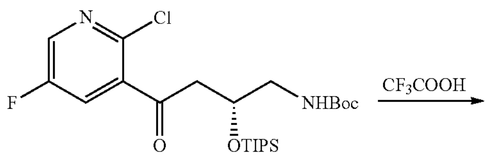

48a

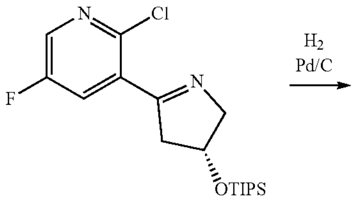

49a

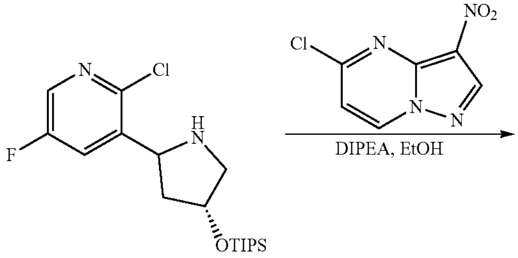

50a

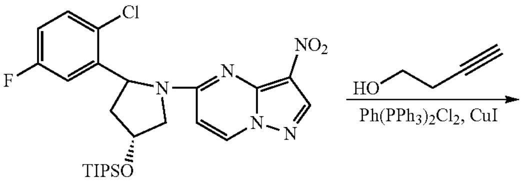

51a

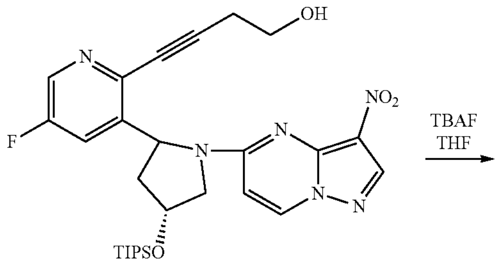

52a

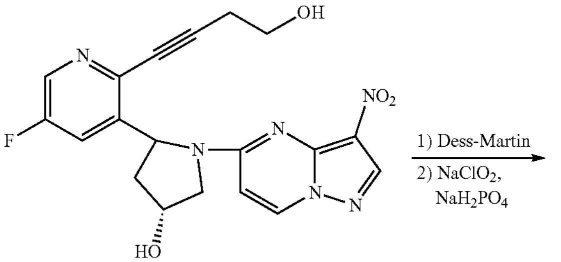

53a

-continued

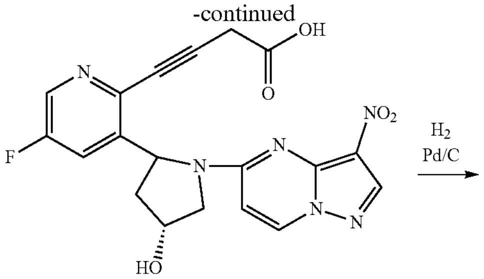

54a

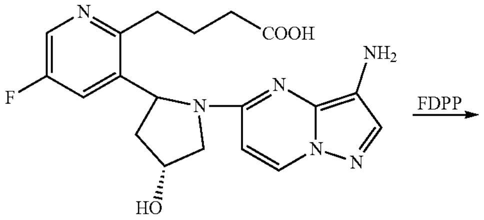

55a

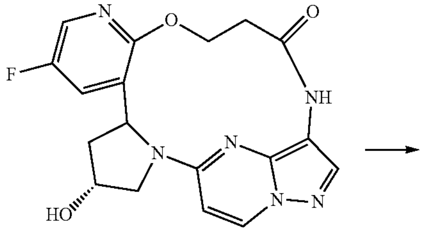

56a

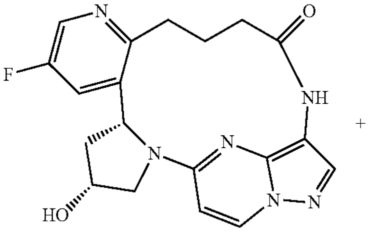

L-9-A

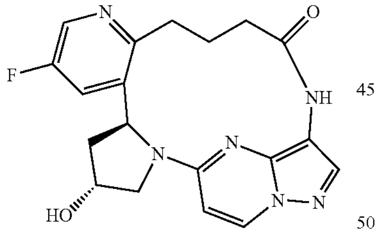

L-9-B

Step 1 Synthesis of Compound 46a (R)-4-hydroxypyrrolidin-2-one (5.0 g, 49.4 mmol) was dissolved in dichloromethane (60 ml), imidazole (4.04 g, 59.3 mmol) was added, and triisopropylchlorosilane (TISCl, 10.5 g, 54.3 mmol) was added under ice bath. After the addition, the reaction was stirred and reacted at room temperature for 1-2 hours. TLC was used to monitor the completion of the reaction. After completion, the reaction was diluted with dichloromethane, and washed 3 times with water. After concentration, the organic phase was purified by column chromatography to afford 10.3 g of compound 46a as colorless oily liquid. Yield: 81%. LC-MS (APCI): m/z=258.3 $(M+1)^+$.

Step 2 Synthesis of Compound 47a

Compound 46a (10.3 g, 40 mmol) was dissolved in dichloromethane (100 ml), triethylamine (6.07 g, 60 mmol) was added, and di-tert-butyl dicarbonate (10.5 g, 48 mmol) was added under ice bath. After the addition, the reaction was heated to room temperature and reacted for 3-4 hours. TLC was used to monitor the completion of the reaction. After completion, the reaction was concentrated to remove the solvent, purified by column chromatography to afford 12.73 g of compound 47a as colorless oily liquid. Yield: 89%. LC-MS (APCI): m/z=358.3 $(M+1)^+$.

Step 3 Synthesis of Compound 48a 2-chloro-3-bromo-5-fluoropyridine (19.53 g, 93 mmol) was dissolved in anhydrous THF (100 mL), isopropyl magnesium chloride solution (43.4 mL, 86.8 mmol) was slowly added dropwise at −40° C., and after the addition, the mixture was naturally warmed to 0° C. and stirred for 1 h. Then a solution of compound 47a (22.1 g, 62.0 mmol) in anhydrous tetrahydrofuran (30 mL) was slowly added dropwise at −40° C., and the mixture was stirred at room temperature for 30 min after the addition. The reaction solution was poured into 100 mL of saturated ammonium chloride solution and stirred for 10 min, then the reaction solution was separated by standing. The aqueous phase was extracted three times with 40 mL ethyl acetate. The organic phases were combined and washed with saturated brine, dried over anhydrous sodium sulfate. The residue was filtered and concentrated, purified by column chromatography to afford 18.5 g of compound 48a as light yellow liquid. Yield: 61.1%. LC-MS (APCI): m/z=490.2 $(M+1)^+$.

Step 4 Synthesis of Compound 49a

Compound 48a (1.88 g, 3.85 mmol) was dissolved in dichloromethane (10 mL), 2 mL trifluoroacetic acid was added, and the mixture was stirred at room temperature for 1 h. TLC was used to monitor the completion of the reaction. The reaction solution was washed with saturated sodium bicarbonate aqueous solution, the organic phase was separated, and the aqueous phase was extracted 3 times with dichloromethane. The organic phases were combined, washed with saturated brine, concentrated to afford crude product of compound 49a, which was directly used in the next reaction. LC-MS (APCI): m/z=372.3 $(M+1)^+$.

Step 5 Synthesis of Compound 50a

Compound 49a (1.43 g, 3.85 mmol) was dissolved in anhydrous methanol (20 mL), Pd/C (100 mg) was added, and hydrogenated at room temperature overnight. The reaction was filtered, the filter residue was washed with 20 mL ethyl acetate, and the filtrate was concentrated to afford 1.36 g of compound 50a as colorless oily liquid which was directly used in the next step. Yield: 95%. LC-MS (APCI): m/z=374.3 $(M+1)^+$.

Step 6 Synthesis of Compound 51a

Compound 50a (1.38 g, 3.7 mmol) and 5-chloro-3-nitro-pyrazolo[1,5-a]pyrimidine (733 mg, 3.7 mmol) were dissolved in absolute ethanol (10 mL), DIPEA (1.91 g, 14.8 mmol) was added at room temperature, and the mixture was heated to reflux for 30 min. The reaction solution was concentrated, purified by column chromatography (PE/EA, 30%-50%) to afford 1.74 g of compound 51a as light yellow solid powder. Yield: 88%. LC-MS (APCI): m/z=535.5 $(M+1)^+$.

Step 7 Synthesis of Compound 52a

Compound 51a (1.6 g, 3 mmol) and 3-hydroxybutyn-1-ol (893 mg, 4.5 mmol) were dissolved in dioxane (30 ml), bis(triphenylphosphine)palladium dichloride (21 mg, 0.03 mmol) and copper iodide (57 mg, 0.3 mmol) were added under nitrogen protection. The reaction was heated to 100° C. and stirred for 5 hours. TLC was used to monitor the completion of the reaction. After completion, the reaction was cooled to room temperature, diluted with water, and extracted with ethyl acetate for 3-4 times. The organic phases were combined, washed with saturated brine, concentrated and then purified by column chromatography to afford 938 mg of compound 52a as light yellow solid. Yield: 55%. LC-MS (APCI): m/z=569.8 $(M+1)^+$.

Step 8 Synthesis of Compound 53a

Compound 52a (1.01 g, 1.78 mmol) was dissolved in anhydrous tetrahydrofuran (20 ml), a solution of 1M tetrabutylammonium fluoride in tetrahydrofuran (3.6 ml, 3.6 mmol) was slowly added dropwise. After the addition, the reaction was stirred at room temperature for half an hour. TLC was used to monitor the completion of the reaction. After completion, the reaction was concentrated to remove the solvent, purified by silica gel column chromatography to afford 565 mg of compound 53a. Yield: 77%. LC-MS (APCI): m/z=4131 $(M+1)^+$.

Step 9 Synthesis of Compound 54a

Compound 53a (601 mg, 1.46 mmol) was dissolved in dichloromethane (20 ml), Dess-Martin oxidant (928 mg, 2.19 mmol) was added in batches under ice bath, the reaction was gradually warmed to room temperature and stirred for 1 hour. TLC was used to monitor the completion of the reaction. After completion, the reaction was diluted with dichloromethane, and washed 2-3 times with saturated sodium bicarbonate solution. After 0.5 concentration, the organic phase was directly used in the next reaction.

The intermediate obtained in the previous step was dissolved in acetonitrile (20 ml), sodium dihydrogen phosphate (876 mg, 7.3 mmol) was added, and a solution of sodium chlorite (264 mg, 2.92 mmol) in 5 ml water was added under ice bath, and the reaction was gradually warmed to room temperature and stirred for 1 hour. TLC was used to monitor the completion of the reaction. After completion, the reaction was added with an excess amount of water, and extracted with ethyl acetate for 3-4 times. The organic phases were combined, washed with saturated brine, concentrated and then purified by column chromatography to afford 553 mg of compound 54a. Yield: 89%. LC-MS (APCI): m/z=427.7 $(M+1)^+$.

Step 10 Synthesis of Compound 55a

Compound 54a (536 mg, 1.26 mmol) was dissolved in methanol (15 ml), a catalytic amount of Pd/C was added, and the reaction was put under a balloon filled with hydrogen gas. The reaction was stirred and reacted at room temperature overnight. TLC was used to monitor the completion of the reaction. After completion, the catalyst was removed by filtration, and the filtrate was concentrated to afford 449 mg crude product of compound 55a, which was directly used in the next reaction. Yield: 89%. LC-MS (APCI): m/z=401.7 $(M+1)^+$.

Step 11 Synthesis of Compound 56a

Compound 55a (448 mg, 1.12 mmol) was dissolved in anhydrous DMF (20 ml), and DIPEA (580 mg, 4.48 mmol) and FDPP (516.4 mg, 1.34 mmol) were added. The reaction was stirred at room temperature overnight under nitrogen protection, TLC was used to monitor the completion of the reaction. After completion, the reaction was diluted with an excess amount of water, and extracted with ethyl acetate for 3-4 times. The organic phases were combined, washed with saturated brine, concentrated and then purified by column chromatography to afford 248 mg of compound 56a as light yellow solid. Yield: 58%. LC-MS (APCI): m/z=383.4 $(M+1)^+$. $^1$H NMR (500 MHz. DMSO-$d_6$) δ 8.73 (d. J=7.7 Hz, 1H), 8.41 (d, J=2.4 Hz, 1H), 8.00 (s, 1H), 7.62 (d, J=6.6 Hz, 1H), 7.57 (dd, J=9.9, 2.4 Hz, 1H), 6.62 (d, J=7.7 Hz, 1H), 5.36 (t, J=6.5 Hz, 1H), 4.16 (m, 1H), 4.05 (dd, J=16.9, 7.0 Hz, 2H), 3.75 (dd, J=14.0, 8.6 Hz, 1H), 3.64-3.51 (m, 1H), 2.91 (d, J=16.9 Hz, 1H), 2.54 (dd, J=14.0, 10.9 Hz, 1H), 2.44 (dd, J=13.4, 6.5 Hz, 2H), 2.23 (dd, J=12.0, 6.2 Hz, 1H), 2.12-1.96 (m, 11H), 1.79-1.66 (m, 1H).

Step 12 Synthesis of Compounds L-9-A and L-9-B

Preparative chiral column: CHIRALPAK IC (brand name), 4.6 mm×250 mm (internal diameter×length), 5 μm (particle size of the filler)

Column temperature: 30° C.

Flow rate: 1.0 L/min

UV detection wavelength: 254 nm

Mobile phase: methyl tert-butyl ether:methanol=70:30

Under the above preparative chiral column and chiral resolution conditions, racemic compound 56a was separated to afford target compound L-9-A (retention time: 14.26 min, relative amount: 45.0%) and L-9-B (retention time: 5.38 min, relative amount: 42.9%).

Example 16: Preparation of 9-fluoro-13-oxa-2,11,18,21,22,25-hexaazapentacyclo[$17.5.2.0^{2,6}.0^{7,12}.0^{22,26}$]hexadecane-1(25),7,9,11,19(26),20,23-heptaene-17-one (Compound 64a), (6R)-9-fluoro-13-oxa-2,11,18,21,22,25-hexaazapentacyclo[$17.5.2.0^{2,6}.0^{7,12}.0^{22,26}$]hexadecane-1(2),7,9,11,19(26),20,23-heptaene-17-one (Compound L-10-A), and (6S)-9-fluoro-13-oxa-2,11,18,21,22,25-hexaazapentacyclo[$17.5.2.0^{2,6}.0^{7,12}.0^{22,26}$]hexadecane-1(25),7,9,11,19(26),20,23-heptaene-17-one (Compound L-10-B)

64a

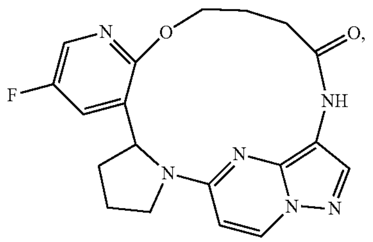

,

L-10-A

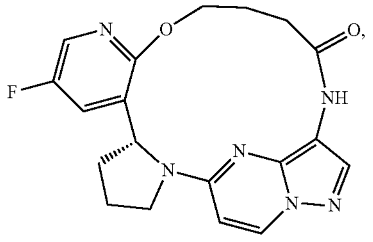

,

L-10-B

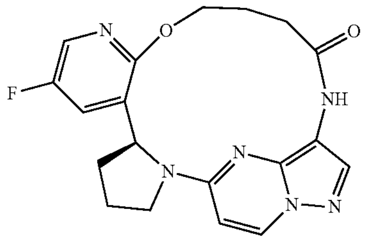

The following route was used for the synthesis:

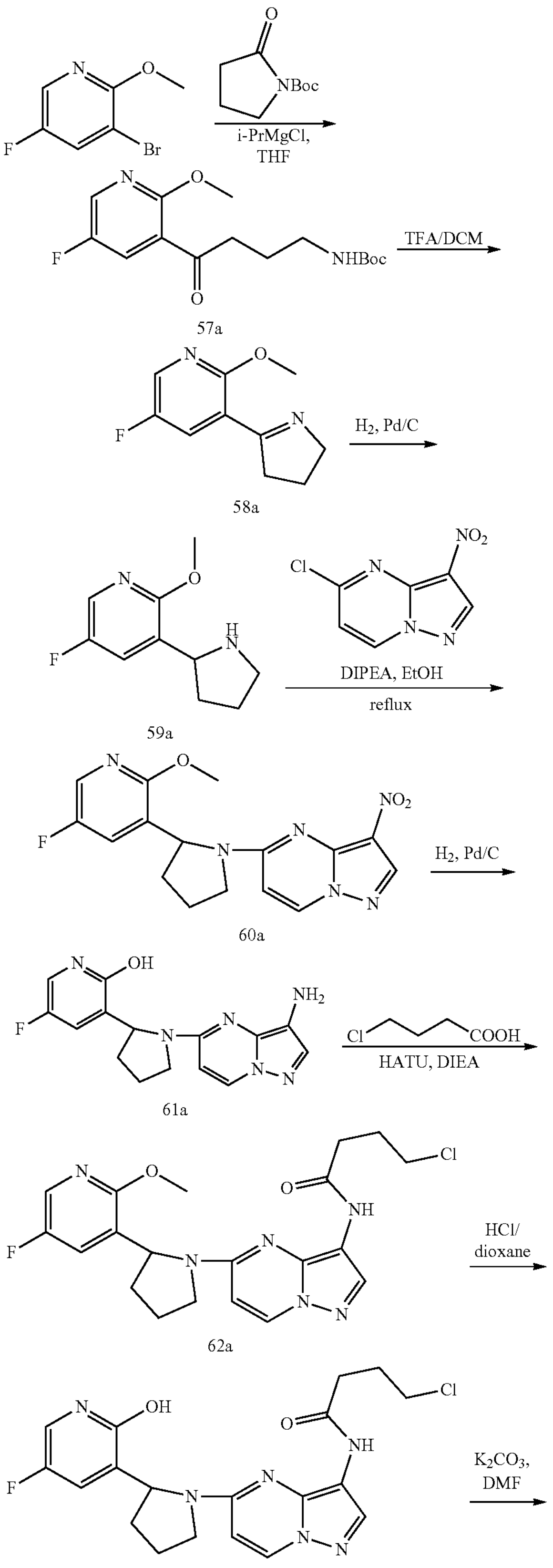

57a, 58a, 59a, 60a, 61a, 62a, 63a

-continued

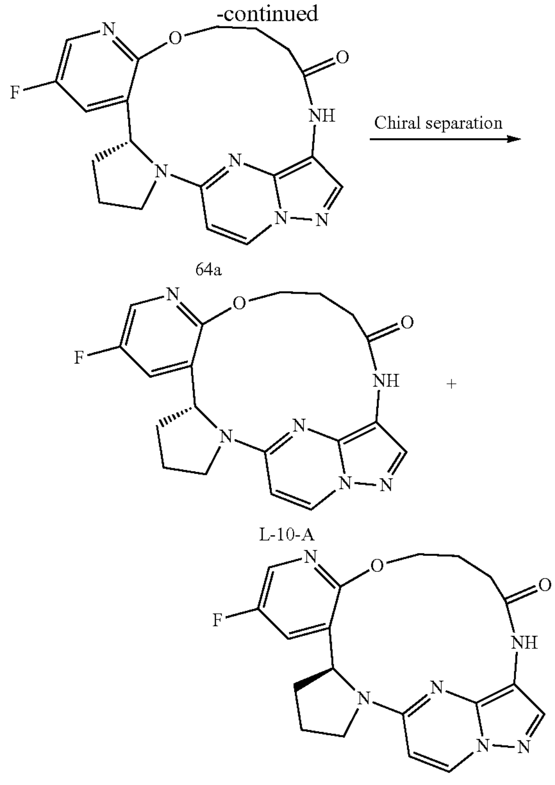

64a, L-10-A, L-10-B

Step 1 Synthesis of Compound 57a 2-methoxy-3-bromo-5-fluoropyridine (19.16 g, 93 mmol) was dissolved in anhydrous THF (100 mL), and isopropyl magnesium chloride solution (43.4 mL, 86.8 mmol) was slowly added dropwise at −40° C. After the addition, the mixture was naturally warmed to 0° C. and stirred for 1 h. A solution of N-tert-butoxycarbonyl-2-pyrrolidone (11.46 g, 62.0 mmol) in anhydrous tetrahydrofuran (30 mL) was then slowly added dropwise at −40° C. After the addition, the mixture was stirred at room temperature for 30 min. The reaction solution was poured into 100 mL of saturated ammonium chloride solution and stirred for 10 min, then the reaction solution was separated by standing. The aqueous phase was extracted three times with 40 mL ethyl acetate. The organic phases were combined and washed with saturated brine, dried over anhydrous sodium sulfate. The residue was filtered and concentrated, purified by column chromatography to afford 16.2 g of compound 57a as light yellow liquid. Yield: 56%. LC-MS (APCI): m/z=313.2 $(M+1)^+$.

Step 2 Synthesis of Compound 58a

Compound 57a (1.2 g, 3.85 mmol) was dissolved in dichloromethane (10 mL), 2 mL trifluoroacetic acid was added, and the mixture was stirred at room temperature for 1 h. TLC was used to monitor the completion of the reaction. The reaction solution was washed with saturated sodium bicarbonate aqueous solution, the organic phase was separated, and the aqueous phase was extracted 3 times with dichloromethane. The organic phases were combined, washed with saturated brine, concentrated to afford crude product of compound 58a, which was directly used in the next reaction. LC-MS (APCI): m/z=195.2 $(M+1)^+$.

Step 3 Synthesis of Compound 59a

Compound 58a (747 mg, 3.85 mmol) was dissolved in anhydrous methanol (10 mL), Pd/C (50 mg) was added, and hydrogenated at room temperature overnight. The reaction was filtered, the filter residue was washed with 20 mL ethyl acetate, and the filtrate was concentrated to afford 731 mg of compound 59a as colorless oily liquid which was directly used in the next step. Yield: 97%. LC-MS (APCI): m/z=197.3 $(M+1)^+$.

Step 4 Synthesis of Compound 60a

Compound 59a (725 mg, 3.7 mmol) and 5-chloro-3-nitropyrazolo[1,5-a]pyrimidine (733 mg, 3.7 mmol) were dissolved in absolute ethanol (10 mL), DIPEA (1.91 g, 14.8 mmol) was added at room temperature, and the mixture was heated to reflux for 30 min. The reaction solution was concentrated, purified by column chromatography (PE/EA, 30%-50%) to afford 1.01 g of compound 60a as light yellow solid powder. Yield: 76%. LC-MS (APCI): m/z=359.5 $(M+1)^+$.

Step 5 Synthesis of Compound 61a

Compound 60a (1.01 g, 2.80 mmol) was dissolved in methanol (20 ml), a catalytic amount of Pd/C was added, and the reaction was put under a balloon filled with hydrogen gas. The reaction was stirred and reacted at room temperature for 4-5 hours. TLC was used to monitor the completion of the reaction. After completion, the catalyst was removed by filtration, and the filtrate was concentrated to afford 920 mg crude product of the title product, which was directly used in the next reaction. LC-MS (APCI): m/z=329.6 $(M+1)^+$.

Step 6 Synthesis of Compound 62a

Compound 61a (920 mg, 2.8 mmol) was dissolved in anhydrous DMF (15 ml), 4-chlorobutyric acid (360 mg, 2.94 mmol) and HATU (1.28 g, 3.36 mmol) were added, and then DIPEA (1.08 g, 8.4 mmol) was added, and the reaction was stirred at room temperature and reacted for 5 hours. TLC was used to monitor the completion of the reaction. After completion, the reaction was diluted with an excess amount of water, and extracted with ethyl acetate. The organic phases were combined, washed with saturated brine, concentrated and then purified by column chromatography to afford 679 mg of compound 62a as light yellow solid. Yield: 56%. LC-MS (APCI): m/z=433.6 $(M+1)^+$.

Step 7 Synthesis of Compound 63a

Compound 62a (679 mg, 1.57 mmol) was added in a solution of 4N hydrogen chloride in dioxane (10 ml). The reaction was heated to reflux and stirred overnight. TLC was used to monitor the completion of the reaction. After completion, the reaction was concentrated to remove the solvent, which was directly used in the next reaction. LC-MS (APCI): m/z=−419.2 $(M+1)^+$.

Step 8 Synthesis of Compound 64a

Compound 63a (655 mg, 1.57 mmol) was dissolved in anhydrous DMF (20 ml), and potassium carbonate (434 mg, 3.14 mmol) was added. The reaction was heated to 80° C. and stirred to react overnight. TLC was used to monitor the completion of the reaction. After completion, the reaction was added with an excess amount of water, and extracted with ethyl acetate for 3-4 times. The organic phases were combined, washed with saturated saline, and then concentrated to remove the solvent, purified by silica gel column chromatography to afford 252 mg of compound 64a as white solid. Yield: 41%. LC-MS (APCI): m/z=383.3 $(M+1)^+$. $^1H$ NMR (500 MHz, DMSO-d) δ 8.76 (d, J=7.7 Hz, 1H), 8.42 (d, J=2.4 Hz, 1H), 8.01 (s, 11H), 7.62 (d, J=6.6 Hz, 11H), 7.57 (dd, J=9.9, 2.4 Hz, 1H), 6.60 (d, J=7.7 Hz, 1H), 5.36 (t, J=6.5 Hz, 1H), 4.05 (dd, J=16.9, 7.0 Hz, 2H), 3.75 (dd, J=14.0, 8.6 Hz, 1H), 3.67-3.51 (m, 1H), 2.91 (d, J=16.9 Hz, 1H), 2.54 (dd, J=14.0, 10.9 Hz, 1H), 2.44 (dd, J=13.4, 6.5 Hz, 2H), 2.23 (dd, J=12.0, 6.2 Hz, 2H), 2.12-1.96 (m, 1H), 1.79-1.66 (m, 1H).

Step 9 Synthesis of Compounds L-10-A and L-10-B

Preparative chiral column: CHIRALPAK IC (brand name), 4.6 mm×250 mm (internal diameter×length), 5 μm (particle size of the filler)

Column temperature: 30° C.

Flow rate: 1.0 mL/min

UV detection wavelength: 254 nm

Mobile phase: methyl tert-butyl ether:methanol=70:30

Under the above preparative chiral column and chiral resolution conditions, racemic compound 64a was separated to afford target compound L-10-A (retention time: 27.54 min, relative amount: 49.4%) and L-10-B (retention time: 38.22 min, relative amount: 49.3%).

Biological Activity Assay

Biological Example 1: Biochemical Kinase Analysis

Inhibition of TRKA, TRKB, TRKC kinases can be measured by HTRF (High Fluorescence Resonance Energy Transfer) method. The reaction was performed in a 384-well plate at 23° C. with a volume of 20 μL. TRKA TRKB or TRKC kinase were mixed with pre-formulated and diluted compounds of different concentrations for ten minutes in duplicate for each concentration, wherein 11 concentrations made with a 3-fold gradient dilution from the starting concentration of 300 nM were made and the final concentration of DMSO was 2%. The corresponding substrate and ATP were added thereto, and reacted at room temperature for 20 minutes (both a negative and a positive control were set: negative control is blank control, positive control is Entrectinib). After the reaction, detection reagent was added thereto (reagent in HTRF Kinase TK kit), and after incubation at room temperature for 30 minutes, detection was carried out by PerkinElmer Envision microplate reader for determining enzyme activity in the presence of the compounds of the present disclosure at various concentrations, and the inhibitory activity of different concentrations of compounds against enzyme activity was calculated. After that, in accordance with four-factors function and Graphpad 5.0 software, inhibitory activity on enzyme activity under different concentrations of compounds was fitted and $IC_{50}$ values were calculated. The data of the compounds tested in this analysis is shown in Table 1.

Biological Example 2: KM12 Cell Proliferation Analysis

The CGT method was used to detect the in vitro anti-proliferative activity of the compounds of the present disclosure on tumor cells cultured in vitro. The KM12 cell line was maintained in RPMI-1640 medium containing 10% fetal bovine serum and antibiotics, the cells in the logarithmic growth phase were harvested and planted in a 96-well plate. The plate was incubated in an incubator at 37° C., containing 5% carbon dioxide gas overnight. After the test compounds were dissolved in DMSO, a 3-fold concentration gradient dilution with 9 compound concentrations was made. Pre-prepared compounds of different concentrations were transferred to the cell plate in triplicate for each concentration, and continue culturing for 72 h. The final concentration of DMSO in the system was 0.1%, and the initial concentration of the test compound was 300 nM.

CellTiter-Glo reagent was added to the cell plate, and incubated at room temperature for 30 minutes to stabilize the optical signal. Detection was carried out by PerkinElmer Envision microplate reader for determining the inhibitory activity of the compound of the present disclosure at various concentrations on cell proliferation. The inhibitory activity of compounds at different concentrations on cell proliferation was fitted according to Graphpad 5.0 software, and $IC_{50}$ values were calculated. The data of the compounds tested in this analysis is shown in Table 1.

TABLE 1

| | Kinase $IC_{50}$ (nM) | | | Cell $IC_{50}$ (nM) |
|---|---|---|---|---|
| | TRK A | TRK B | TRK C | KM12 |
| TPX-005 | 0.11 | 0.09 | 0.12 | 1.97 |
| LOXO-195 | 0.19 | 0.09 | 0.09 | 2.73 |
| T-1 | <0.17 | <0.17 | <0.17 | 5.13 |
| T-2-A | 0.19 | 0.10 | 0.06 | 1.60 |
| T-2-B | 0.36 | 0.09 | 0.09 | 4.79 |
| T-3 | 0.34 | 0.57 | 0.52 | |
| T-4 | 4.91 | 5.31 | 5.41 | |
| T-5 | 93.88 | 225.32 | 257.93 | |
| L-1-A | 0.18 | 0.10 | 0.14 | 0.55 |
| L-1-B | 21.07 | 15.54 | 14.20 | 161.51 |
| Compound 9a | 0.17 | 0.10 | 0.10 | 1.78 |
| L-2-A | 0.17 | 0.10 | 0.10 | 0.25 |
| L-2-B | 0.41 | 0.13 | 0.18 | 0.65 |
| L-3-B | >100 | 70.75 | >100 | |

Biological Example 3: Ba/F3 Cell Proliferation Analysis

The CGT method was used to detect the in vitro anti-proliferative activity of the compounds of the present disclosure on three cell lines cultured in vitro.

The Ba/F3 parent cells, Ba/F3 LMNA-NTRK1 and Ba/F3 LMNA-NTRK1-G595R cells were maintained in RPMI-1640 medium containing 10% fetal bovine serum and antibiotics, respectively, and the cells in the logarithmic growth phase were harvested and planted in a 96-well plate. The plate was incubated in a incubator at 37° C., containing 5% carbon dioxide gas overnight, wherein 8 ng/ml IL-3 was added to the Ba/F3 parent cells. After dissolving the test compounds in DMSO, 9 compound concentrations were made with a 3.16-fold gradient dilution. The pre-prepared compounds of different concentrations were transferred to the cell plate in triplicate for each concentration, and continued for culturing for 72 h. The final concentration of DMSO in the system was 0.1%, and the initial concentration of the test compounds in the Ba/F3 parent cell was 10 M, and the initial concentration of the test compounds in Ba/F3 LMNA-NTRK1 and Ba/F3 LMNA-NTRK1-G595R cells was 1 μM. CellTiter-Glo reagent was added to the cell plate, and incubated at room temperature for 30 minutes to stabilize the optical signal. Detection was carried out by PerkinElmer Envision microplate reader for determining the inhibitory activity of the compound of the present disclosure at various concentrations on cell proliferation. The inhibitory activity of compounds at different concentrations on cell proliferation was fitted according to Graphpad 5.0 software, and $IC_{50}$ values were calculated. The results showed that the compound of the present disclosure has almost no inhibitory effect on Ba/F3 parent cells but has an inhibitory effect on Ba/F3 LMNA-NTRK1 and Ba/F3 LMNA-NTRK1-G595R cells.

Biological Example 4: Pharmacokinetic Experiment in Rats 6 male Sprague-Dawley rats (7-8 weeks old, and weighing approximately 210 g) were divided into 2 groups with 3 rats in each group. The rats were intravenously or orally administered a single dose of compounds (3 mg/kg intravenously, 10 mg/kg orally) to compare pharmacokinetic differences.

The rats were feeded on standard food and water. Fasting was started 16 hours before the test. The drug was dissolved in PEG400 and dimethyl sulfoxide. The blood samples were collected from eyelids at the time points of 0.083 hour, 0.25 hour, 0.5 hour, 1 hour, 2 hours, 4 hours, 6 hours, 8 hours, 12 hours, and 24 hours after administration.

Rats were briefly anesthetized after inhalation of diethyl ether and 300 μL of blood sample was collected from the eyelids into test tubes. There was 30 μL of 1% heparin salt solution in the test tube. Tubes were dried at 60° C. overnight before use. After the blood sample was collected at the last time point, the rats were sacrificed after ether anesthesia.

Immediately after the collection of the blood sample, the test tube was gently inverted at least 5 times to ensure sufficient mixing and then placed on ice. The blood sample was centrifuged at 5000 rpm at 4° C. for 5 minutes to separate the plasma from the red blood cells. 100 μL of plasma was aspirated into a clean plastic centrifuge tube with a pipette, marking with the name of the compound and time point. Plasma was stored at −80° C. prior to analysis. The concentration of the compound of the present disclosure in plasma was determined by LC-MS/MS. The pharmacokinetic parameters were calculated based on the blood concentration of the drug for each animal at different time points.

Experiments showed that the compounds of the present disclosure have better pharmacokinetic properties in vivo, and therefore have better pharmacodynamics and treatment effects. The pharmacokinetic experimental results of representative example compounds in rat are summarized in Table 2 and Table 3 below.

TABLE 2

| | TPX-0005 | | T-1 | | T-2-A | |
|---|---|---|---|---|---|---|
| Dosage | IV | PO | IV | PO | IV | PO |
| (mg/kg) | 3 | 10 | 3 | 10 | 3 | 10 |
| $T_{max}$ (h) | 0.08 | 1.67 | 0.08 | 1.67 | 0.08 | 2.17 |
| $C_{max}$ (h) | 2185.8 | 731.8 | 2120.7 | 1863.8 | 2101.3 | 994.4 |
| $AUC_{last}$ (h*ng/mL) | 3558.9 | 5474.1 | 6238.6 | 11543.3 | 6560.9 | 11522.3 |
| $AUC_{INF\_pred}$ (h*ng/mL) | 3577.6 | 5586.6 | 6348.3 | 13062.9 | 6617.6 | 12905.9 |
| $MRT_{INF\_pred}$ (h) | 1.76 | 5.42 | 4.04 | 6.23 | 3.44 | 7.37 |
| $Vz_{\_pred}$ (L/kg) | 4.46 | 15.81 | 3.28 | 10.05 | 2.67 | 6.70 |
| $Cl_{\_pred}$ (L/kg) | 0.90 | 1.90 | 0.47 | 0.77 | 0.45 | 0.83 |
| $T_{1/2}$ (h) | 5.77 | 0.76 | 9.05 | 0.36 | 5.59 | 4.84 |
| F (%) | 46.14 | | 55.51 | | 52.69 | |

TABLE 3

| | LOXO-195 | | L-1-A | | L-2-A | |
|---|---|---|---|---|---|---|
| Dosage | IV | PO | IV | PO | IV | PO |
| (mg/kg) | 3 | 10 | 3 | 10 | 3 | 10 |
| $T_{max}$ (h) | 0.08 | 0.33 | 0.08 | 1.58 | 0.08 | 0.50 |
| $C_{max}$ (h) | 5008.5 | 1663.8 | 2158.6 | 1492.0 | 1623.9 | 1405.3 |
| $AUC_{last}$ (h*ng/mL) | 4666.0 | 4071.1 | 5005.1 | 11320.7 | 2476.3 | 4470.5 |

TABLE 3-continued

| | LOXO-195 | | L-1-A | | L-2-A | |
|---|---|---|---|---|---|---|
| $AUC_{INF\_pred}$ (h*ng/mL) | 4669.6 | 4087.8 | 5028.5 | 11331.0 | 2477.8 | 4528.8 |
| $MRT_{INF\_pred}$ (h) | 0.54 | 2.31 | 2.18 | 4.90 | 1.20 | 2.80 |
| $Vz_{\_pred}$ (L/kg) | 0.75 | 5.13 | 1.75 | 2.92 | 1.85 | 8.50 |
| $Cl_{\_pred}$ (L/kg) | 0.71 | 2.45 | 0.60 | 0.92 | 1.23 | 2.44 |
| $T_{1/2}$ (h) | 1.45 | 4.11 | 2.20 | 5.77 | 2.41 | 2.02 |
| F (%) | 26.17 | | 67.86 | | 54.16 | |

The above is a further detailed description of the present disclosure in conjunction with specific embodiments, and it cannot be assumed that the specific implementation of the present disclosure is limited to these descriptions. For ordinary artisan in the technical field to which the present disclosure belongs, without deviating from the concept of the present disclosure, various simple deductions or replacements may be made, which should be regarded as falling within the protection scope of the present disclosure.

Should be:
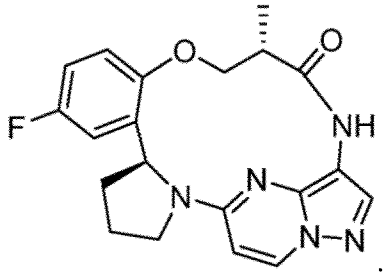
In the Claims
Claim 8, at Column 113, Lines 48-57, the Structure "L-4-D":
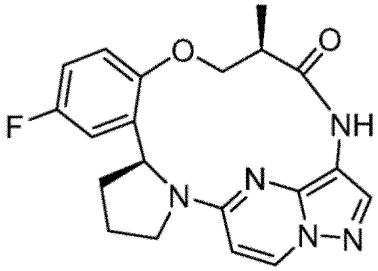
Should be:
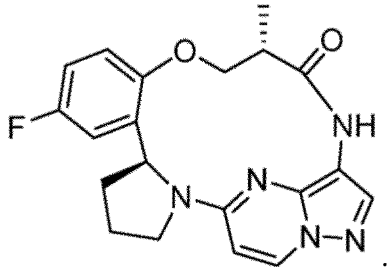

What is claimed is:

1. A compound of formula (I):

(I)

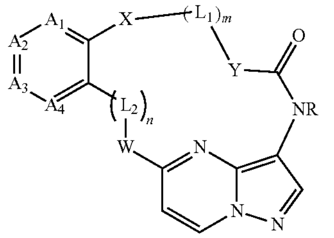

wherein, $A_1$ is $CR_1$;

$A_2$ is $CR_2$;

$A_3$ is $CR_3$;

$A_4$ is $CR_4$;

wherein $R_1$, $R_2$, $R_3$ and $R_4$ are independently selected from H, D, halogen, —CN, and —$NO_2$;

$L_1$ is $C(R_{1a})(R_{2a})$;

$L_2$ is $C(R_{1b})(R_{2b})$;

X is selected from O, S, and $N(R_{1c})$;

Y is selected from O, S, $N(R_{1d})$ and $C(R_{1d})(R_{2d})$;

W is selected from O, S, and $N(R_{1e})$;

R is selected from H, D, $C_{1-6}$ alkyl, and $C_{1-6}$ haloalkyl; wherein the above groups are optionally substituted by one or more D atoms until completely deuterated;

m is selected from 1, 2, 3, 4 and 5;

n is selected from 1, 2 and 3;

wherein, $R_{1a}$ and $R_{2a}$ are each independently selected from H, D, halogen, $C_{1-6}$ alkyl, $C_{1-6}$ haloalkyl, $C_{2-6}$ alkenyl, and $C_{2-6}$ alkynyl; or $R_{1a}$, $R_{2a}$ together with the atom to which they are attached form a $C_{3-7}$ cycloalkyl; wherein the above groups are optionally substituted by one or more D atoms until completely deuterated;

$R_{1b}$ and $R_{2b}$ are each independently selected from H, D, halogen, $C_{1-6}$ alkyl, $C_{1-6}$ haloalkyl, $C_{2-6}$ alkenyl, and $C_{2-6}$ alkynyl; wherein the above groups are optionally substituted by one or more D atoms until completely deuterated;

$R_{1c}$ is selected from H, D, $C_{1-6}$ alkyl, $C_{1-6}$ haloalkyl, $C_{2-6}$ alkenyl, and $C_{2-6}$ alkynyl; wherein the above groups are optionally substituted by one or more D atoms until completely deuterated;

$R_{1d}$ and $R_{2d}$ are each independently selected from H, D, halogen, $C_{1-6}$ alkyl, $C_{1-6}$ haloalkyl, $C_{2-6}$ alkenyl, and $C_{2-6}$ alkynyl; or $R_{1d}$, $R_{2d}$ together with the atom to which they are attached form a $C_{3-7}$ cycloalkyl; wherein the above groups are optionally substituted by one or more D atoms until completely deuterated;

$R_{1e}$ is selected from H, D, $C_{1-6}$ alkyl, $C_{1-6}$ haloalkyl, $C_{2-6}$ alkenyl, and $C_{2-6}$ alkynyl; wherein the above groups are optionally substituted by one or more D atoms until completely deuterated; and substituents on different atoms in $-(L_2)_n$-W— can be connected to form a-3- to 10-membered heterocyclyl; wherein the above groups are optionally substituted by one or more D atoms until completely deuterated;

or a pharmaceutically acceptable salt, enantiomer, diastereomer, or racemate thereof;

wherein,

"3- to 7-membered heterocyclyl" is a radical of a 3- to 7-membered non-aromatic ring system having ring carbon atoms and 1 to 3 ring heteroatoms;

"5- to 10-membered heteroaryl" refers to a radical of a 5-10 membered monocyclic or bicyclic 4n+2 aromatic ring system having ring carbon atoms and 1-4 ring heteroatoms, wherein each heteroatom is independently selected from nitrogen, oxygen and sulfur.

2. The compound according to claim 1, which is a compound of formula (III-1) or (III-2):

(III-1)

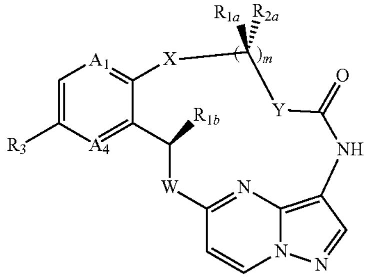

or (III-2)

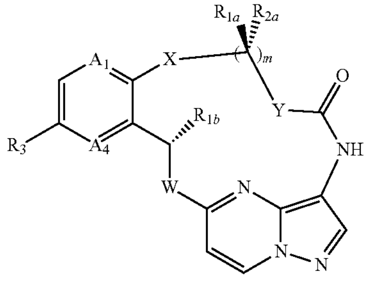

wherein, $A_1$ is $CR_1$;

$A_4$ is $CR_4$;

wherein $R_1$, $R_3$ and $R_4$ are independently selected from H, D, halogen, —CN, and —$NO_2$;

X is O;

Y is selected from $N(R_{1d})$ and $C(R_{1d})(R_{2d})$;

W is selected from O and NH;

m is selected from 1, 2 and 3;

$R_{1a}$ and $R_{2a}$ are each independently selected from H, D, halogen, $C_{1-6}$ alkyl, $C_{1-6}$ haloalkyl, $C_{2-6}$ alkenyl, and $C_{2-6}$ alkynyl; or $R_{1a}$, $R_{2a}$ together with the atom to which they are attached form a $C_{3-7}$ cycloalkyl;

wherein the above groups are optionally substituted by one or more D atoms until completely deuterated;

$R_{1b}$ is selected from H, D, halogen, $C_{1-6}$ alkyl, $C_{1-6}$ haloalkyl, $C_{2-6}$ alkenyl, and $C_{2-6}$ alkynyl; wherein the above groups are optionally substituted by one or more D atoms until completely deuterated;

and wherein, $R_{1d}$ and $R_{2d}$ are each independently selected from H, D, halogen, $C_{1-6}$ alkyl, $C_{1-6}$ haloalkyl, $C_{2-6}$ alkenyl, and $C_{2-6}$ alkynyl; or $R_{1d}$, $R_{2d}$ together with the atom to which they are attached form a $C_{3-7}$ cycloalkyl; wherein the above groups are optionally substituted by one or more D atoms until completely deuterated;

or a pharmaceutically acceptable salt, enantiomer, diastereomer, or racemate thereof.

3. The compound according to claim 1, which is a compound of formula (IV-1) or (IV-2):

(IV-1)

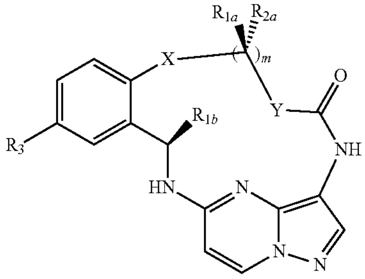

or (IV-2)

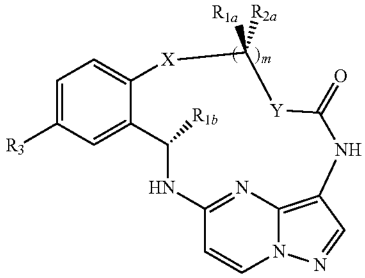

wherein, $R_3$ is selected from H, D, halogen, —CN, and —$NO_2$;

X is O;

Y is selected from NH, $CH_2$ and C(Me)(Me); wherein the above groups are optionally substituted by one or more D atoms until completely deuterated;

m is selected from 1, 2 and 3;

$R_{1a}$ and $R_{2a}$ are each independently selected from H, D, halogen, $C_{1-6}$ alkyl, $C_{1-6}$ haloalkyl, $C_{2-6}$ alkenyl, and $C_{2-6}$ alkynyl; or $R_{1a}$, $R_{2a}$ together with the atom to which they are attached form a $C_{3-7}$ cycloalkyl; wherein the above groups are optionally substituted by one or more D atoms until completely deuterated; and $R_{1b}$ is selected from H, D, halogen, $C_{1-6}$ alkyl, $C_{1-6}$ haloalkyl, $C_{2-6}$ alkenyl, and $C_{2-6}$ alkynyl; wherein the above groups are optionally substituted by one or more D atoms until completely deuterated;

or a pharmaceutically acceptable salt, enantiomer, diastereomer, or racemate thereof.

4. The compound according to claim 1, which is a compound of formula (VI-1) or (VI-2):

(VI-1)

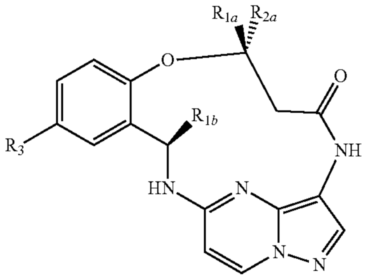

or (VI-2)

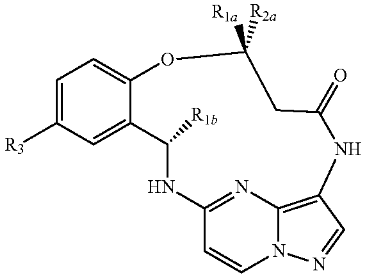

wherein, $R_3$ is selected from H, D, and halogen;

$R_{1a}$ and $R_{2a}$ are each independently selected from H, D, $C_{1-6}$ alkyl and $C_{1-6}$ haloalkyl; wherein the above groups are optionally substituted by one or more D atoms until completely deuterated; and $R_{1b}$ is selected from H, D, $C_{1-6}$ alkyl and $C_{1-6}$ haloalkyl; wherein the above groups are optionally substituted by one or more D atoms until completely deuterated;

or a pharmaceutically acceptable salt, enantiomer, diastereomer, or racemate thereof.

5. The compound according to claim 1, which is a compound of formula (I'):

(I')

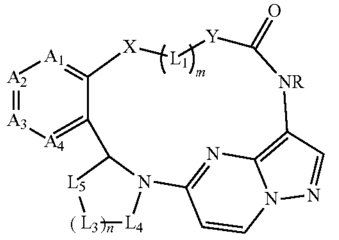

$A_1$ is $CR_1$;

$A_2$ is $CR_2$;

$A_3$ is $CR_3$;

$A_4$ is $CR_4$;

wherein $R_1$, $R_2$, $R_3$ and $R_4$ are independently selected from H, D, halogen, —CN, and —$NO_2$;

$L_1$ is $C(R_{1a})(R_{2a})$;

X is selected from O, S, and $N(R_{1c})$;

Y is selected from O, S, $N(R_{1d})$ and $C(R_{1d})(R_{2d})$;

$L_3$ is $C(R_{1f})(R_{2f})$;

$L_4$ is $C(R_{1g})(R_{2g})$;

$L_5$ is $C(R_{1h})(R_{2h})$;

R is selected from H, D, $C_{1-6}$ alkyl, and $C_{1-6}$ haloalkyl; wherein the above groups are optionally substituted by one or more D atoms until completely deuterated;

m is selected from 1, 2, 3, 4 and 5;

n is selected from 1, 2 and 3;

wherein, $R_{1a}$ and $R_{2a}$ are each independently selected from H, D, halogen, $C_{1-6}$ alkyl, $C_{1-6}$ haloalkyl, $C_{2-6}$ alkenyl, and $C_{2-6}$ alkynyl; or $R_{1a}$, $R_{2a}$ together with the atom to which they are attached form a $C_{3-7}$ cycloalkyl; wherein the above groups are optionally substituted by one or more D atoms until completely deuterated;

$R_{1d}$ and $R_{2d}$ are each independently selected from H, D, halogen, $C_{1-6}$ alkyl, $C_{1-6}$ haloalkyl, $C_{2-6}$ alkenyl, and $C_{2-6}$ alkynyl; or $R_{1d}$, $R_{2d}$ together with the atom to which they are attached form a $C_{3-7}$ cycloalkyl; wherein the above groups are optionally substituted by one or more D atoms until completely deuterated;

$R_{1f}$ and $R_{2f}$ are each independently selected from H, D, halogen, $C_{1-6}$ alkyl, and $C_{1-6}$ haloalkyl; wherein the above groups are optionally substituted by one or more D atoms until completely deuterated;

$R_{1g}$ and $R_{2g}$ are each independently selected from H, D, halogen, $C_{1-6}$ alkyl, and $C_{1-6}$ haloalkyl; wherein the above groups are optionally substituted by one or more D atoms until completely deuterated; and $R_{1h}$ and $R_{2h}$ are each independently selected from H, D, halogen, $C_{1-6}$ alkyl, and $C_{1-6}$ haloalkyl; wherein the above groups are optionally substituted by one or more D atoms until completely deuterated;

or a pharmaceutically acceptable salt, enantiomer, diastereomer, or racemate thereof.

6. The compound according to claim 5, which is a compound of formula (III'-1) or (III'-2):

(III'-1)

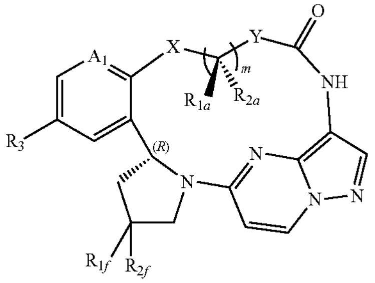

or (III'-2)

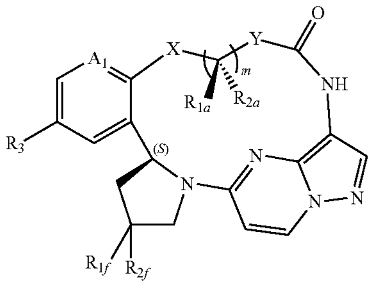

wherein, $A_1$ is $CR_1$;

wherein $R_1$ and $R_3$ are each independently selected from H, D, halogen, —CN, and —$NO_2$;

X is O;

Y is selected from $CH_2$, and $CH(R_{1d})$; wherein the above groups are optionally substituted by one or more D atoms until completely deuterated;

$R_{1a}$ and $R_{2a}$ are each independently selected from H, D, halogen, $C_{1-6}$ alkyl, $C_{1-6}$ haloalkyl, $C_{2-6}$ alkenyl, and $C_{2-6}$ alkynyl; or $R_{1a}$, $R_{2a}$ together with the atom to which they are attached form a $C_{3-7}$ cycloalkyl; wherein the above groups are optionally substituted by one or more D atoms until completely deuterated;

$R_{1d}$ is selected from halogen, $C_{1-6}$ alkyl, $C_{1-6}$ haloalkyl, $C_{2-6}$ alkenyl, and $C_{2-6}$ alkynyl; wherein the above groups are optionally substituted by one or more D atoms until completely deuterated;

$R_{1f}$ and $R_{2f}$ are each independently selected from H, D, halogen, $C_{1-6}$ alkyl, $C_{1-6}$ haloalkyl, $C_{2-6}$ alkenyl, and $C_{2-6}$ alkynyl; wherein the above groups are optionally substituted by one or more D atoms until completely deuterated;

m is selected from 1, 2 and 3;

or a pharmaceutically acceptable salt, enantiomer, diastereomer, or racemate thereof.

7. The compound according to claim 5, which is a compound of formula (V'-1) or (V'-2):

(V'-1)

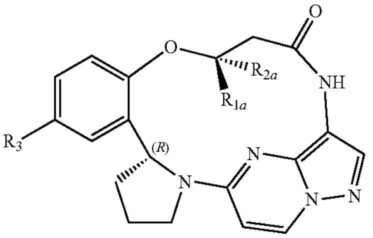

or (V'-2)

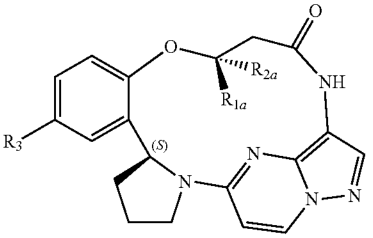

wherein, $R_3$ is selected from H, D, halogen, —CN and —$NO_2$;

$R_{1a}$ and $R_{2a}$ are each independently selected from H, D, $C_{1-6}$ alkyl and $C_{1-6}$ haloalkyl; wherein the above groups are optionally substituted by one or more D atoms until completely deuterated;

or a pharmaceutically acceptable salt, enantiomers, diastereomer, or racemate thereof.

8. The compound according to claim 1, which is selected from the group consisting of:

T-1

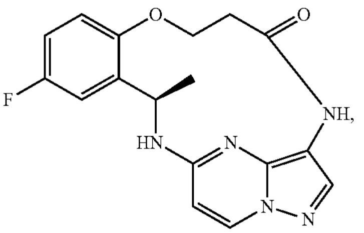

-continued
T-2-A
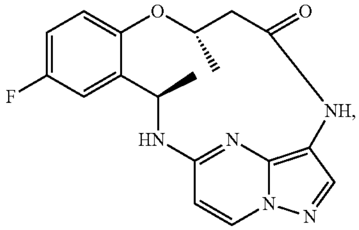
,
T-2-B
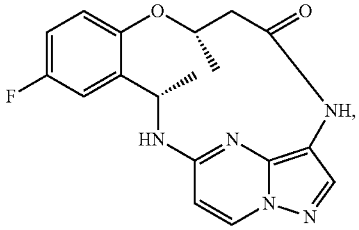
,
T-3
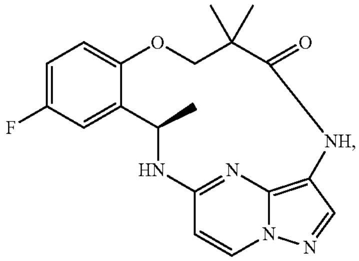
,
T-6
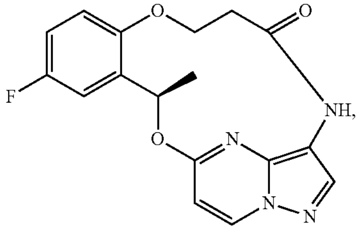
,
L-1-A
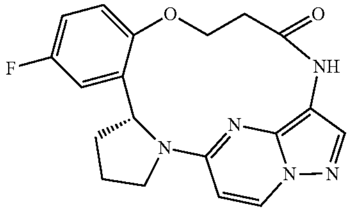
,
L-1-B
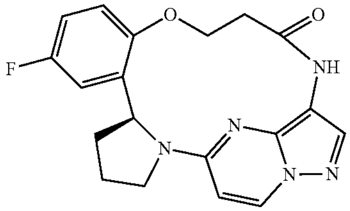
,
9a
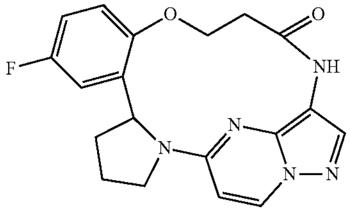
,
-continued
L-2-A
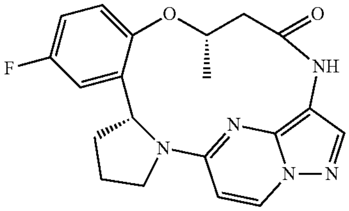
,
L-2-B
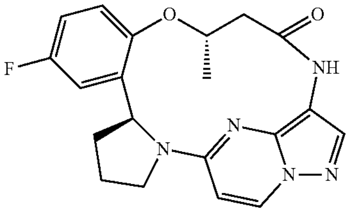
,
13a
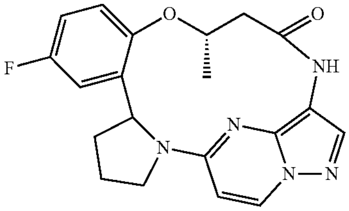
,
L-3-A
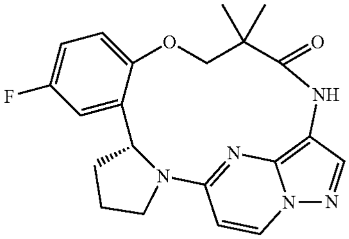
,
L-3-B
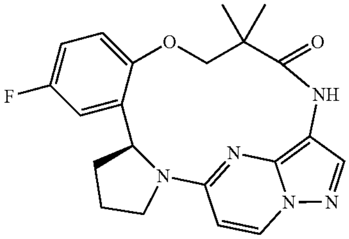
,
18a
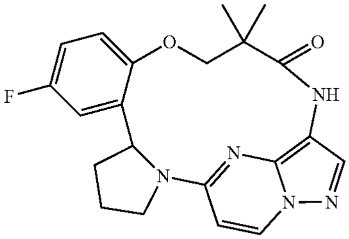
, -continued
23a
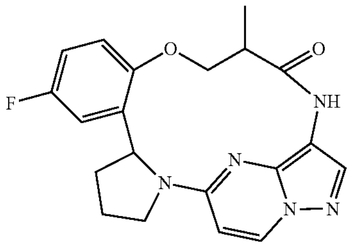
,
L-4-A
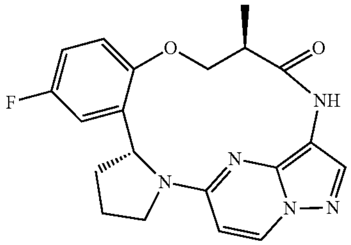
,
L-4-B
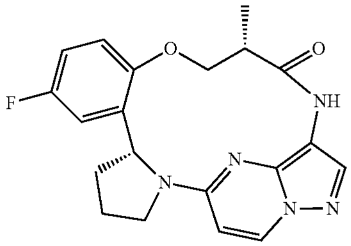
,
L-4-C
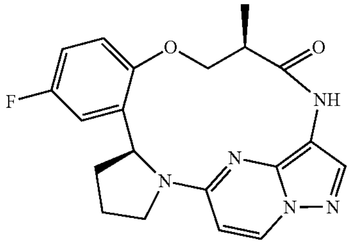
,
L-4-D
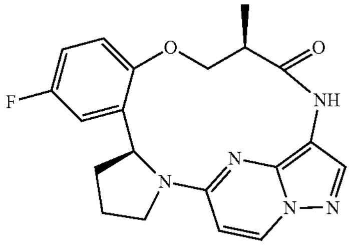
,
28a
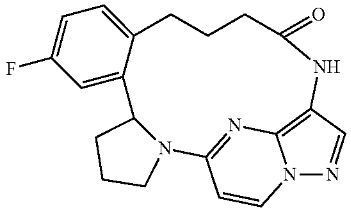
,
-continued
L-5-A
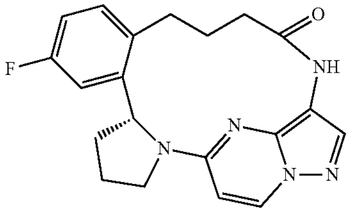
,
L-5-B
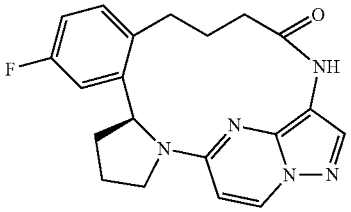
,
32a
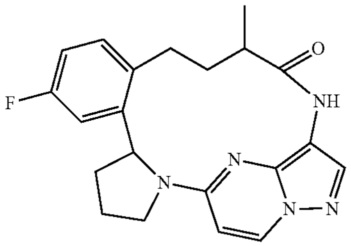
,
L-6-A
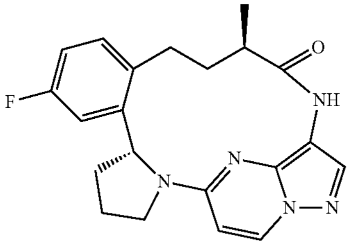
,
L-6-B
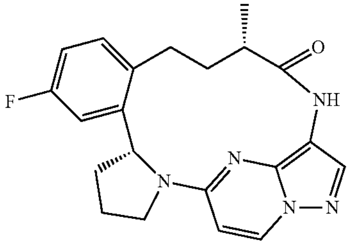
,
L-6-C
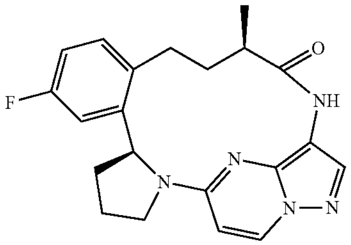
, and -continued

L-6-D

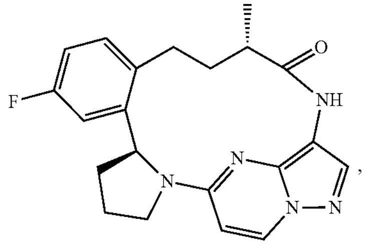

or a pharmaceutically acceptable salt, enantiomer, diastereomer, or racemates thereof.

9. A pharmaceutical composition, comprising a compound according to claim 1, or a pharmaceutically acceptable salt, enantiomer, diastereomer, or racemate thereof, and pharmaceutically acceptable excipient(s).

10. The compound according to claim 3, wherein, $R_3$ is selected from H, D, halogen, —CN and —$NO_2$;

X is O;

Y is selected from NH, $CH_2$ and C(Me)(Me); wherein the above groups are optionally substituted by one or more D atoms until completely deuterated;

m is selected from 1, 2 and 3;

$R_{1a}$ and $R_{2a}$ are each independently selected from H, D, $C_{1-6}$ alkyl and $C_{1-6}$ haloalkyl; wherein the above groups are optionally substituted by one or more D atoms until completely deuterated;

$R_{1b}$ is selected from $C_{1-6}$ alkyl and $C_{1-6}$ haloalkyl; wherein the above groups are optionally substituted by one or more D atoms until completely deuterated;

or a pharmaceutically acceptable salt, enantiomer, diastereomer, or racemate thereof.

11. The compound according to claim 3, wherein, $R_3$ is selected from H, D, and halogen;

X is O;

Y is selected from $CH_2$ and C(Me)(Me); wherein the above groups are optionally substituted by one or more D atoms until completely deuterated;

m is selected from 1, 2 and 3;

$R_{1a}$ and $R_{2a}$ are each independently selected from H, D, $C_{1-6}$ alkyl and $C_{1-6}$ haloalkyl; wherein the above groups are optionally substituted by one or more D atoms until completely deuterated;

$R_{1b}$ is selected from $C_{1-6}$ alkyl and $C_{1-6}$ haloalkyl; wherein the above groups are optionally substituted by one or more D atoms until completely deuterated;

or a pharmaceutically acceptable salt, enantiomer, diastereomer, or racemate thereof.

12. The compound according to claim 7, wherein, $R_3$ is selected from H, D, and halogen;

$R_{1a}$ and $R_{2a}$ are each independently selected from H, D, $C_{1-6}$ alkyl and $C_{1-6}$ haloalkyl; and $R_{1a}$ and $R_{2a}$ are not H or D at the same time; wherein the above groups are optionally substituted by one or more D atoms until completely deuterated;

or a pharmaceutically acceptable salt, enantiomer, diastereomer, or racemate thereof.

* * * * *

UNITED STATES PATENT AND TRADEMARK OFFICE
CERTIFICATE OF CORRECTION

PATENT NO. : 11,358,973 B2
APPLICATION NO. : 17/047877
DATED : June 14, 2022
INVENTOR(S) : Yihan Wang et al.

It is certified that error appears in the above-identified patent and that said Letters Patent is hereby corrected as shown below:

In the Specification

At Column 33, Lines 6-14, the Structure "L-4-D":

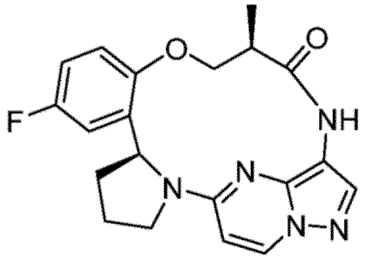

Should be:

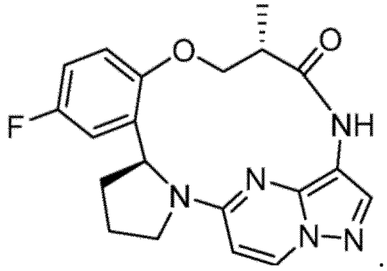

At Column 75, Lines 2-12, the Structure "L-4-D":

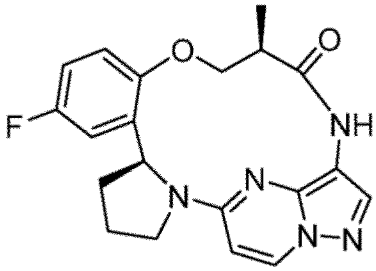

Signed and Sealed this
Thirty-first Day of January, 2023

Katherine Kelly Vidal

Katherine Kelly Vidal
*Director of the United States Patent and Trademark Office*